United States Patent
Ma et al.

(10) Patent No.: US 11,424,412 B2
(45) Date of Patent: Aug. 23, 2022

(54) ORGANIC ELECTROLUMINESCENT MATERIAL AND ORGANIC ELECTROLUMINESCENT DEVICE COMPRISING SAME

(71) Applicant: Shaanxi Lighte Optoelectronics Material Co., Ltd., Xi'an (CN)

(72) Inventors: Tiantian Ma, Xi'an (CN); Qiqi Nie, Xi'an (CN); Zhen Feng, Xi'an (CN); Hongyan Li, Xi'an (CN); Xunshan Sha, Xi'an (CN); Zhanyi Sun, Xianyang (CN); Yalong Wang, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/613,794

(22) PCT Filed: May 18, 2020

(86) PCT No.: PCT/CN2020/090876
§ 371 (c)(1),
(2) Date: Nov. 23, 2021

(87) PCT Pub. No.: WO2020/253445
PCT Pub. Date: Dec. 24, 2020

(65) Prior Publication Data
US 2022/0149278 A1    May 12, 2022

(30) Foreign Application Priority Data

Jun. 19, 2019 (CN) .......................... 201910532443.8

(51) Int. Cl.
| | |
|---|---|
| *C07C 211/54* | (2006.01) |
| *C07C 211/61* | (2006.01) |
| *H01L 51/00* | (2006.01) |
| *H01L 51/50* | (2006.01) |
| *C07D 307/91* | (2006.01) |
| *C07D 333/76* | (2006.01) |
| *C07D 209/86* | (2006.01) |
| *C07D 409/12* | (2006.01) |

(52) U.S. Cl.
CPC .......... *H01L 51/006* (2013.01); *C07C 211/54* (2013.01); *C07C 211/61* (2013.01); *C07D 209/86* (2013.01); *C07D 307/91* (2013.01); *C07D 333/76* (2013.01); *C07D 409/12* (2013.01); *H01L 51/0061* (2013.01); *H01L 51/0058* (2013.01); *H01L 51/0072* (2013.01); *H01L 51/0073* (2013.01); *H01L 51/0074* (2013.01); *H01L 51/5056* (2013.01); *H01L 51/5096* (2013.01)

(58) Field of Classification Search
CPC .... C07C 211/54; C07C 211/61; H01L 51/006
See application file for complete search history.

(56) References Cited

U.S. PATENT DOCUMENTS

| | | |
|---|---|---|
| 6,777,111 B1 | 8/2004 | Tanaka |
| 2016/0181535 A1 | 6/2016 | Tsuji |
| 2019/0165273 A1* | 5/2019 | Takada ................ H01L 51/0061 |

FOREIGN PATENT DOCUMENTS

| | | | |
|---|---|---|---|
| CN | 1674747 A | | 9/2005 |
| CN | 107148408 A | | 9/2017 |
| CN | 109535011 A | | 3/2019 |
| CN | 109836339 A | * | 6/2019 |
| CN | 109836339 A | | 6/2019 |
| CN | 109912431 A | | 6/2019 |
| CN | 109928911 A | | 6/2019 |
| CN | 109942439 A | | 6/2019 |
| CN | 109994640 A | | 7/2019 |
| CN | 110003019 A | | 7/2019 |
| CN | 110003091 A | | 7/2019 |
| CN | 110010783 A | | 7/2019 |
| CN | 110010784 A | | 7/2019 |
| CN | 110183333 A | | 8/2019 |
| KR | 20180078177 A | | 7/2018 |
| WO | 2018216990 A1 | | 11/2018 |

OTHER PUBLICATIONS

International Search Report from corresponding International Application No. PCT/CN2020/090876, dated Aug. 12, 2020, 6 pages.
Mir Hedayatullah et al., "Synthesis of reactive s-triazines bearing a cage system derived from adamantane as precursors of hexamethylmelamine analogues," Heterocycles, vol. 51, No. 8, 1999, pp. 1891-1896.

* cited by examiner

*Primary Examiner* — Vu A Nguyen
(74) *Attorney, Agent, or Firm* — Tucker Ellis LLP

(57) ABSTRACT

The present invention related to an organic electroluminescent material and organic electroluminescent device thereof. The organic electroluminescent material has the structural formula as shown in formula 1. Compared with a monoamine structure containing an adamantyl group, the diamine structure disclosed in the present invention has higher HOMO energy level and hole mobility, and can exhibit higher efficiency and service life than a monoamine material device. The organic electroluminescent device comprising the organic electroluminescent material has lower driving voltage, and higher luminous efficiency and service life.

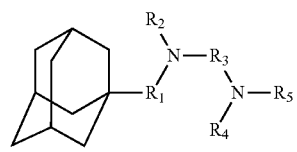

(1)

11 Claims, No Drawings

ORGANIC ELECTROLUMINESCENT MATERIAL AND ORGANIC ELECTROLUMINESCENT DEVICE COMPRISING SAME

TECHNICAL FIELD

The present disclosure relates to the technical field of organic electroluminescence, and in particular to, an organic electroluminescent material and an organic electroluminescent device including the material.

BACKGROUND

In recent years, as a new generation of display technology, an organic electroluminescent device (OLED) has been popular with people gradually. A common organic electroluminescent device includes an anode, a cathode, and one or more organic layers arranged between the cathode and the anode. When a voltage is applied between the cathode and the anode, an electric field will be generated between the two electrodes. Under the action of the electric field, electrons on the cathode side move to an emitting layer, and holes on the anode side also move to the emitting layer. The electrons are combined with the holes to form excitons in the emitting layer. The excitons are in an excited state, release energy to the outside, and emit light to the outside in a process of changing from releasing energy in the excited state to releasing energy in a ground state. Therefore, it is very important to improve the recombination of electrons and holes in the OLED.

In order to improve the luminance, efficiency, and service life of the organic electroluminescent device, multilayer structures are generally used in the device. The multilayer structures include: a hole injection layer, a hole transport layer, an electron-blocking layer, an emitting layer, an electron transport layer, and the like. The organic layers have capacities of improving the injection efficiency of carriers (holes and electrons) at interfaces of the layers, and balancing transport of the carriers between the layers, thereby improving the luminance and efficiency of the device.

At present, a common hole transport material is NPD. Although NPD has excellent hole transport performance, its glass transition temperature (Tg) is only 96° C., such that the organic electroluminescent device tends to crystallize at a high temperature under a high temperature condition, thereby reducing the performance.

Adamantane derivatives have been disclosed in many documents. For example: Patent document CN107148408A relates to an adamantane derivative and an organic electroluminescent device including the same. The device includes a substrate, a cathode and an anode evaporated on the substrate, and an organic layer evaporated between the cathode and the anode, where the organic layer includes a hole transport layer, and the hole transport layer includes an adamantane derivative having the following structure

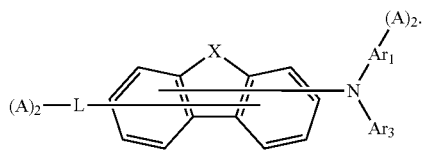

Although these organic electroluminescent materials with fine performance have been developed successively, each of the materials has a monoamine structure. The monoamine structure has a low hole transport rate. Therefore, the efficiency and service life of a device made of the materials still remain to be improved. How to design a novel material with better performance to make adjustment, thereby achieving, for all devices, the effects of reducing the voltage, improving the efficiency and prolonging the service life, has always been a problem to be urgently solved by those skilled in the art.

SUMMARY

An object of the present disclosure is to provide an organic electroluminescent material with excellent performance, which may be used for a hole transport layer, an electron-blocking layer, and the like in an organic electroluminescent device. Another object of the present disclosure is to provide an organic electroluminescent device including the organic electroluminescent material and having lower drive voltage, higher light emitting efficiency, and longer service life.

The present disclosure is implemented using the following technical solution:

An organic electroluminescent material having a structure of chemical formula 1:

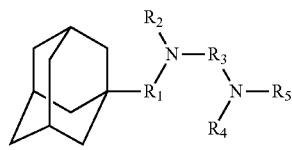

Chemical formula 1 where $R_2$, $R_4$, and $R_5$ are identical or different, and are each independently selected from substituted or unsubstituted alkyl with 1-20 carbon atoms, substituted or unsubstituted alkenyl with 2-20 carbon atoms, substituted or unsubstituted alkynyl with 2-24 carbon atoms, substituted or unsubstituted cycloalkyl with 3-20 carbon atoms, substituted or unsubstituted heterocycloalkyl with 2-20 carbon atoms, substituted or unsubstituted aralkyl with 7-30 carbon atoms, substituted or unsubstituted heteroaralkyl with 2-30 carbon atoms, substituted or unsubstituted aryl with 6-30 carbon atoms, substituted or unsubstituted heteroaryl with 1-30 carbon atoms;

$R_1$ and $R_3$ are identical or different, and are each independently selected from single bond, substituted or unsubstituted arylene with 1-30 carbon atoms, substituted or unsubstituted heteroarylene with 1-30 carbon atoms, substituted or unsubstituted aralkylene with 7-30 carbon atoms, substituted or unsubstituted heteroaralkylene with 2-30 carbon atoms; and the substituents of $R_1$, $R_2$, $R_3$, $R_4$, and $R_5$ are identical or different, and are each independently selected from deuterium, cyano, nitro, halogen, hydroxyl, alkyl group with 1-40 carbon atoms, cycloalkyl group with 3-40 carbon atoms, alkenyl group with 2-40 carbon atoms, alkynyl group with 2-40 carbon atoms, heterocycloalkyl group with 2-40 carbon atoms, aralkyl group with 7-40 carbon atoms, heteroaralkyl group with 2-40 carbon atoms, aryl group with 6-40 carbon atoms, heteroaryl group with 1-40 carbon atoms, alkoxyl group with 1-40 carbon atoms, alkylamino group with 1-40 carbon atoms, arylamino group with 6-40 carbon atoms, alkylthio group with 1-40 carbon atoms, aralkylamino group with 7-40 carbon atoms, heteroarylamino group with 1-24 carbon atoms, alkylsilyl group with 1-45 carbon atoms, arylsilyl group with 6-50 carbon atoms, aryloxyl group with 6-30 carbon atoms, arylthio group with 6-30 carbon atoms.

The present disclosure further provides an organic electroluminescent device, including a cathode, an anode, and one or more organic layers arranged between the cathode and the anode, at least one of the organic layers including the electroluminescent material.

Preferably, the organic layer includes a hole injection layer, a hole transport layer, an electron-blocking layer, an emitting layer, a hole blocking layer, an electron transport layer, and an electron injection layer.

Preferably, the hole transport layer includes the electroluminescent material according to the present disclosure.

Preferably, the electron-blocking layer includes the electroluminescent material according to the present disclosure.

The present disclosure further provides use of the organic electroluminescent material in an organic electroluminescent device.

Compared with the prior art, the present disclosure has the following beneficial technical effects:

Compared with an adamantyl-containing monoamine structure, the diamine structure in the present disclosure has a high HOMO energy level and hole mobility, and may show a higher efficiency and a longer service life than a device made of a monoamine material. Due to many substitution sites of a diamine material, substitution with adamantyl at different sites may also play a role in finer regulation of the spatial structure and molecular stacking of the material. In particular, the material of the present disclosure, when used as an electron-blocking layer, can play a role in better regulating the hole transport rate, thereby further enhancing the efficiency and service life of the device by balancing the hole transport efficiency and the electron transport efficiency. In addition, the diamine structure has a high hole transport efficiency, but tends to crystallize at a low temperature due to its small molecular weight and high symmetry. The combination of the diamine structure and adamantyl introduces highly sterically hindered adamantyl, which can greatly alleviate the crystallization phenomenon, and increase the glass transition temperature and crystallization temperature by 30-50° C., thereby effectively inhibiting the material crystallization and the subsequent problem of short service life of an electroluminescent device.

The organic electroluminescent device including the organic electroluminescent material has lower drive voltage, higher light emitting efficiency, and longer service life.

DETAILED DESCRIPTION

The present disclosure will be further described in detail below in conjunction with specific examples, which are explanations, instead of limitations, of the present disclosure.

In the present disclosure,

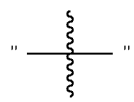

refers to a site for combination with other substituent or a binding site.

In the present disclosure, the quantity of carbon atoms of a substituted or unsubstituted aryl refers to a total quantity of all carbon atoms of the aryl moiety and substituents thereon, and the quantity of carbon atoms of a substituted or unsubstituted heteroaryl refers to the quantity of all carbon atoms of the heteroaryl moiety and substituents thereon. For example, if a substituted or unsubstituted aryl is selected from substituted aryl with 30 carbon atoms, the quantity of all carbon atoms of the aryl moiety and substituents thereon is 30; for example, 9, 9-dimethylfluorenyl belongs to an aryl with 15 carbon atoms. If a substituted or unsubstituted heteroaryl is selected from substituted heteroaryl with 12 carbon atoms, the quantity of all carbon atoms of the heteroaryl moiety and substituents thereon is 12.

In the present disclosure, the term "substituted or unsubstituted" means that a functional group described after the term may have or may not have a substituent.

In the present disclosure, when a specific definition is not otherwise provided, the "hetero" means that at least one heteroatom such as B, N, O, S, Se, Si, or P is included in a functional group, and the remaining atoms of the functional group are selected from carbon and hydrogen. The unsubstituted alkyl may be a "saturated alkyl group" without any double bond or triple bond.

The descriptions "each . . . is independently", " . . . are each independently", and " . . . are independently selected from" used in the present disclosure are interchangeable, should be understood in a broad sense, and may mean that in different groups, specific options expressed by a same symbol do not affect each other, or may mean that in a same group, specific options expressed by a same symbol do not affect each other.

In the present disclosure, the "optional" or "optionally" means that the subsequently described event or circumstance may, but need not, occur, and that the description includes instances where the event or circumstance occurs, and instances where the event or circumstance does not occur. For example, the "heterocyclyl optionally substituted by an alkyl" means that the "alkyl" may, but need not, be present, and that the description includes instances where the heterocyclyl is substituted by the alkyl, and instances where the heterocyclyl is not substituted by the alkyl. "Optionally, two substituents linked to a same atom are linked to each other to form a saturated or unsaturated 5- to 18-membered aliphatic ring or a 5- to 18-membered aromatic ring with the atom to which they are jointly linked," which means that the two substituents linked to the same atom may, but need not, form a ring, including instances where the two substituents are linked to form a saturated or unsaturated 5- to 18-membered aliphatic ring or a 5- to 18-membered aromatic ring, and instances where the two substituents are present independently of each other.

The non-positioned linking bond in the present disclosure refers to a single bond

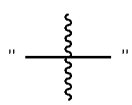

or

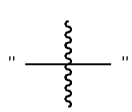

extending from a ring system, and means that one terminal of the linking bond may be linked to any position in the ring system through which the bond runs, while the other terminal is linked to the remaining moiety of the molecule of the compound. For example, as shown in the following formula (X), naphthyl represented by the formula (X) is linked to other position of the molecule via two non-positioned linking bonds running through a dicyclic ring, which means including any possible linking approach as shown in formula (X-1) to formula (X-10).

Formula (X)

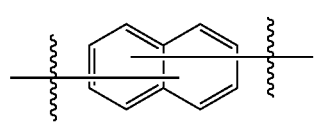

Formula (X-1)

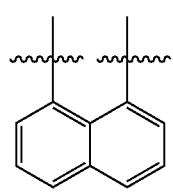

Formula (X-2)

Formula (X-3)

Formula (X-4)

Formula (X-5)

Formula (X-6)

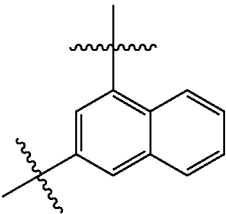

Formula (X-7)

Formula (X-8)

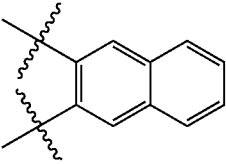

Formula (X-9)

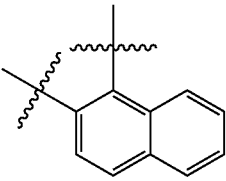

Formula (X-10)

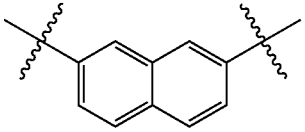

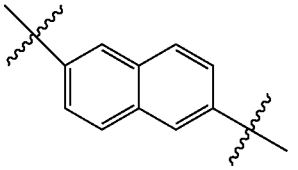

For example, as shown in the following formula (X'), phenanthryl represented by the formula (X') is linked to other position of the molecule via a non-positioned linking bond extending from the middle of a benzene ring on one side, which means including any possible linking approach as shown in formula (X'-1) to formula (X'-4).

(X')

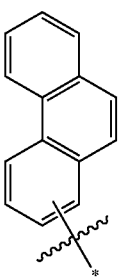

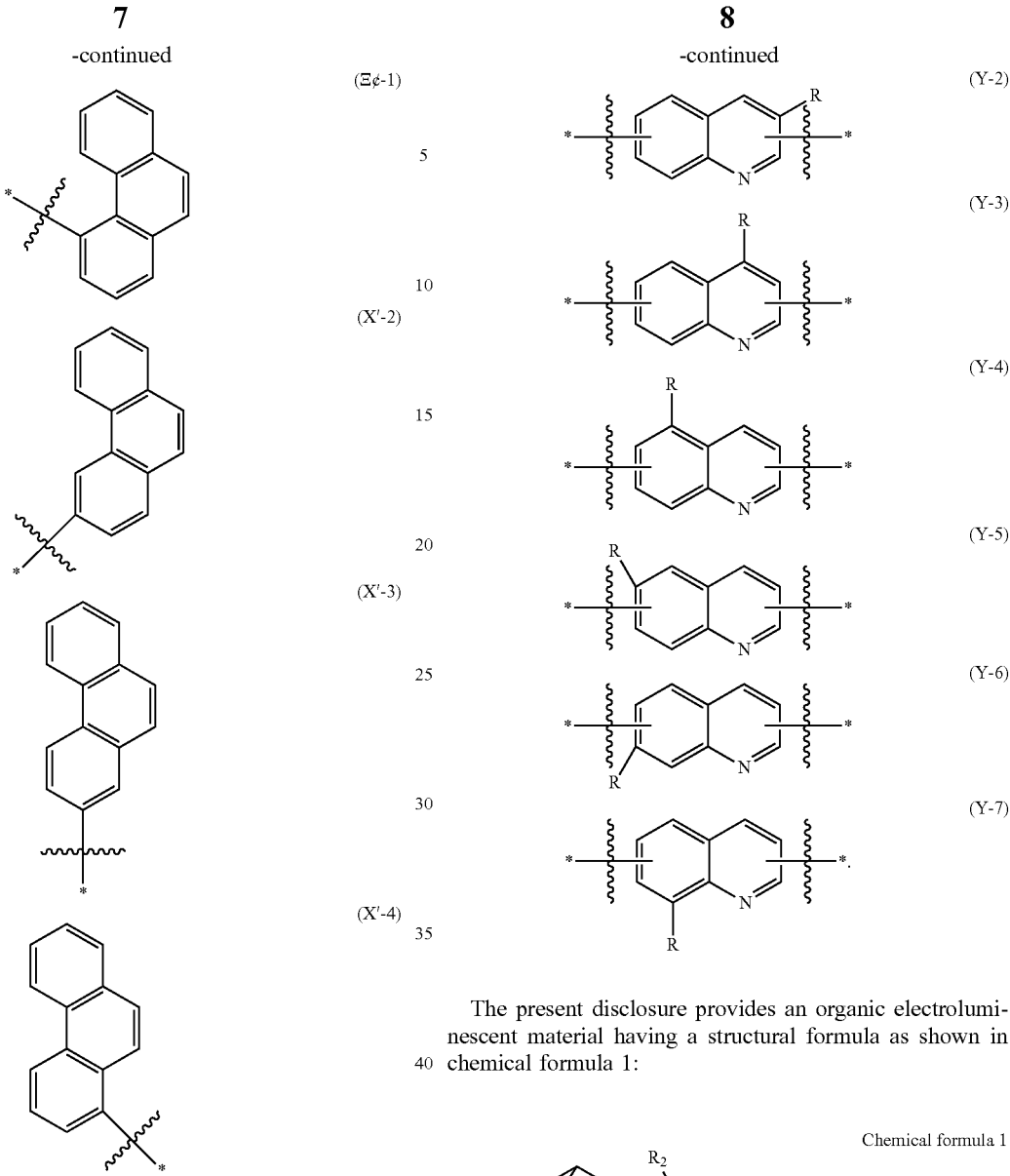

The non-positioned substituent in the present disclosure refers to a substituent linked via a single bond extending from the center of a ring system, and means that the substituent may be linked to any possible position in the ring system. For example, as shown in the following formula (Y), substituent R represented by the formula (Y) is linked to a quinoline ring via a non-positioned linking bond, which means including any possible linking approach as shown in formula (Y-1) to formula (Y-7).

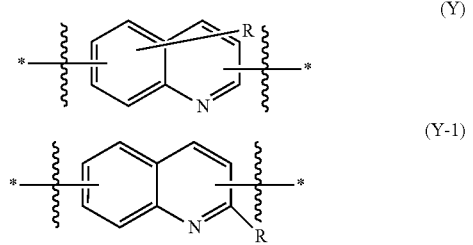

The present disclosure provides an organic electroluminescent material having a structural formula as shown in chemical formula 1:

Chemical formula 1

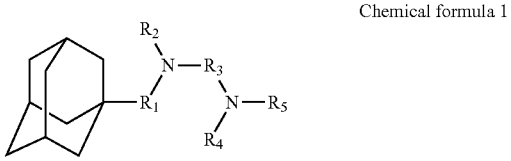

where $R_2$, $R_4$, and $R_5$ are identical or different, and are each independently selected from substituted or unsubstituted alkyl with 1-20 carbon atoms, substituted or unsubstituted alkenyl with 2-20 carbon atoms, substituted or unsubstituted alkynyl with 2-24 carbon atoms, substituted or unsubstituted cycloalkyl with 3-20 carbon atoms, substituted or unsubstituted heterocycloalkyl with 2-20 carbon atoms, substituted or unsubstituted aralkyl with 7-30 carbon atoms, substituted or unsubstituted heteroaralkyl with 2-30 carbon atoms, substituted or unsubstituted aryl with 6-30 carbon atoms, substituted or unsubstituted heteroaryl with 1-30 carbon atoms;

$R_1$ and $R_3$ are identical or different, and are each independently selected from single bond, substituted or unsubstituted arylene with 1-30 carbon atoms, substituted or unsubstituted heteroarylene with 1-30 carbon atoms, substituted or unsubstituted aralkylene with 7-30 carbon atoms, substituted or unsubstituted heteroaralkylene with 2-30 carbon atoms; and the substituents of $R_1$, $R_2$, $R_3$, $R_4$, and $R_5$ are identical or different, and are each independently selected from deuterium, cyano, nitro, halogen, hydroxyl, alkyl group with 1-40 carbon atoms, cycloalkyl group with 3-40 carbon atoms, alkenyl group with 2-40 carbon atoms, alkynyl group with 2-40 carbon atoms, heterocycloalkyl group with 2-40 carbon atoms, aralkyl group with 7-40 carbon atoms, heteroaralkyl group with 2-40 carbon atoms, aryl group with 6-40 carbon atoms, heteroaryl group with 1-40 carbon atoms, alkoxyl group with 1-40 carbon atoms, alkylamino group with 1-40 carbon atoms, arylamino group with 6-40 carbon atoms, alkylthio group with 1-40 carbon atoms, aralkylamino group with 7-40 carbon atoms, heteroarylamino group with 1-24 carbon atoms, alkylsilyl group with 1-45 carbon atoms, arylsilyl group with 6-50 carbon atoms, aryloxyl group with 6-30 carbon atoms, arylthio group with 6-30 carbon atoms.

The unsubstituted alkyl in the present disclosure refers to a linear alkyl with 1-20 carbon atoms or a branched alkyl with 1-13 carbon atoms. In some other embodiments, an alkyl group includes 1-4 carbon atoms; and in still some other embodiments, an alkyl group includes 1-3 carbon atoms. The alkyl group may be optionally substituted by one or more of the substituents described in the present disclosure, e.g., methyl, ethyl, propyl, isobutyl, sec-butyl, pentyl, isopentyl, hexyl, or the like. The substituted alkyl with 1-20 carbon atoms means that at least one hydrogen atom is substituted by a deuterium atom, F, Cl, I, CN, hydroxyl, nitro, amino, phenyl, biphenyl, terphenyl, naphthyl, dibenzofuryl, dibenzothienyl, or the like.

The unsubstituted alkenyl in the present disclosure refers to an alkenyl with 2-20 carbon atoms, a linear alkenyl including a C=C double bond and 2-20 carbon atoms, or a branched alkenyl including 1-13 carbon atoms, e.g., ethenyl, propenyl, allyl, isopropenyl, 2-butenyl, or the like. The substituted alkenyl with 2-20 carbon atoms means that at least one hydrogen atom is substituted by a deuterium atom, F, Cl, I, CN, hydroxyl, nitro, amino, or the like.

The unsubstituted alkynyl in the present disclosure refers to an alkynyl with 2-24 carbon atoms, a linear alkynyl including a C≡C triple bond and 2-35 carbon atoms, or a branched alkynyl including 1-10 carbon atoms, e.g., ethynyl, 2-propynyl, or the like. The substituted alkynyl with 2-24 carbon atoms means that at least one hydrogen atom is substituted by a deuterium atom, F, Cl, I, CN, hydroxyl, nitro, amino, or the like.

The unsubstituted aryl in the present disclosure refers to an aryl with 6-30 carbon atoms. The aryl refers to any functional group or substituent derived from an aromatic carbocycle. The aryl may be a monocyclic aryl or a polycyclic aryl. In other words, the aryl may be a monocyclic aryl, a fused-ring aryl, two or more monocyclic aryls conjugated through a carbon-carbon bond, a monocyclic aryl and a fused-ring aryl conjugated through a carbon-carbon bond, or two or more fused-ring aryls conjugated through a carbon-carbon bond. That is, two or more aryl groups conjugated through a carbon-carbon bond may also be regarded as an aryl of the present disclosure, e.g., phenyl, naphthyl, pyrenyl, dimethylfluorenyl, anthracenyl, phenanthryl, chrysenyl, azulenyl, acenaphthenyl, biphenyl, benzanthracenyl, spirobifluorenyl, perylenyl, indenyl, and the like. The aryl may also be terphenyl, tetraphenyl, pentaphenyl, benzo[9,10]phenanthryl, benzofluoranthenyl, or the like.

The substituted alkyl with 6-30 carbon atoms means that at least one hydrogen atom is substituted by a deuterium atom, F, Cl, I, CN, hydroxyl, nitro, amino, alkyl, phenyl, biphenyl, terphenyl, naphthyl, dibenzofuryl, dibenzothienyl, or the like, where a total quantity of carbon atoms of the aryl moiety and substituents thereon is 6-30, and the quantity of carbon atoms of the substituted aryl may also be 7, 8, 9, 10, 11, 12, 13, 14, 15, 18, or 20. For example, both naphthyl-substituted phenyl and phenyl-substituted naphthyl are substituted aryl with 16 carbon atoms.

The unsubstituted aralkyl in the present disclosure refers to an aralkyl with 7-30 carbon atoms, e.g., methylphenyl, dimethylfluorenyl, or the like. The substituted aralkyl with 7-30 carbon atoms means that at least one hydrogen atom is substituted by a deuterium atom, F, Cl, I, CN, hydroxyl, nitro, amino, or the like.

The unsubstituted heteroaryl in the present disclosure refers to a heteroaryl with 1-30 carbon atoms. The heteroaryl refers to a monovalent aromatic ring including at least one heteroatom in the ring or a derivative thereof. The heteroatom may be at least one of B, O, N, P, Si, or S. The heteroaryl may be a monocyclic heteroaryl or a polycyclic heteroaryl. That is, the heteroaryl may be a single aromatic ring system or a plurality of aromatic ring systems conjugated through a carbon-carbon bond, and any one of the aromatic ring systems is an aromatic monocyclic ring or an aromatic fused ring. The "heteroaryl" in the present disclosure may include 1, 2, 3, 4, 5, 6, 7, 8, 9, or 10 heteroatoms optionally selected from the group consisting of B, O, N, P, Si, Se, and S, and may include 1-30 carbon atoms, e.g., pyridyl, pyrazinyl, pyrimidinyl, pyridazinyl, triazinyl, quinolinyl, indolyl, carbazolyl, dibenzofuryl, dibenzothienyl, dibenzoselenophenyl, or the like. The heteroaryl may also be N-phenylcarbazolyl.

The substituted heteroaryl with 1-30 carbon atoms means that at least one hydrogen atom is substituted by a deuterium atom, F, Cl, I, CN, hydroxyl, nitro, amino, alkyl, phenyl, biphenyl, terphenyl, naphthyl, dibenzofuryl, dibenzothienyl, or the like.

In the present disclosure, the explanation of the aryl may be applied to the arylene, the explanation of the heteroaryl may also be applied to the heteroarylene, the explanation of the alkyl may be applied to the alkylene, and the explanation of the cycloalkyl may be applied to cycloalkylene. The unsubstituted cycloalkyl in the present disclosure refers to a cycloalkyl with 3-20 carbon atoms, e.g., cyclopropyl, cyclobutyl, cyclopentyl, cyclohexyl, norbornyl, adamantyl, or the like. The substituted cycloalkyl with 3-20 carbon atoms means that at least one hydrogen atom is substituted by a deuterium atom, F, Cl, I, CN, hydroxyl, nitro, amino, or the like.

In an alternative embodiment of the present disclosure, $R_1$ and $R_3$ are identical or different, and are each independently selected from single bond, substituted or unsubstituted arylene with 6-25 carbon atoms, or substituted or unsubstituted heteroarylene with 5-18 carbon atoms; $R_2$, $R_4$, and $R_5$ are identical or different, and are each independently selected from the group consisting of single bond, substituted or unsubstituted aryl with 6-18 carbon atoms, substituted or unsubstituted heteroaryl with 5-18 carbon atoms; the substituents of $R_1$, $R_2$, $R_3$, $R_4$, and $R_5$ are identical or different, and are each independently selected from deuterium, cyano, nitro, halogen, hydroxyl, alkyl group with 1-10 carbon atoms, cycloalkyl group with 3-10 carbon atoms, aryl group with 6-15 carbon atoms, heteroaryl group with 3-12 carbon atoms; and when there is more than one substituent, the substituents are identical or different.

In an alternative embodiment of the present disclosure, $R_1$ and $R_3$ are identical to or different from each other, and are each independently selected from the group consisting of groups as shown in chemical formula j-1 to chemical formula j-9:

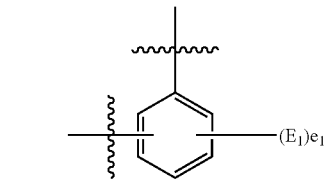
Chemical formula (j-1)

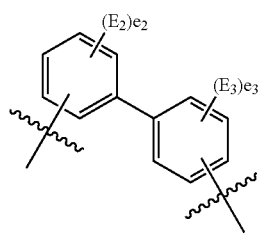
Chemical formula (j-2)

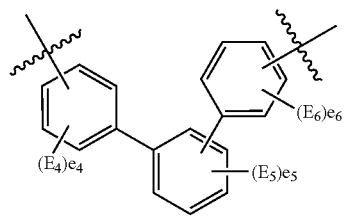
Chemical formula (j-3)

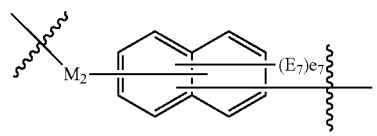
Chemical formula (j-4)

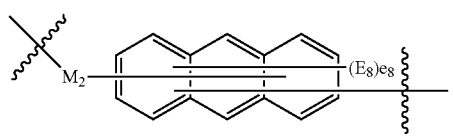
Chemical formula (j-5)

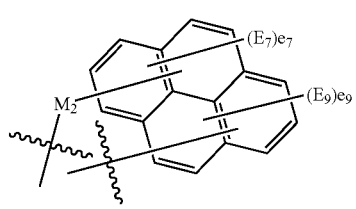
Chemical formula (j-6)

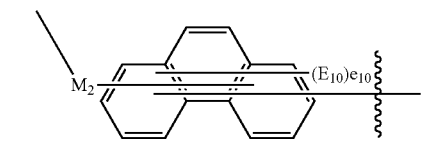
Chemical formula (j-7)

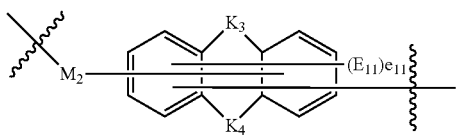
Chemical formula (j-8)

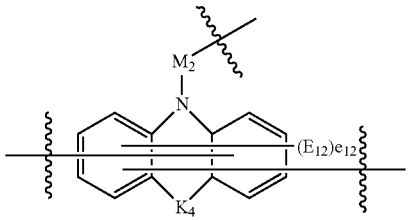
Chemical formula (j-9)

where $M_2$ is selected from single bond or

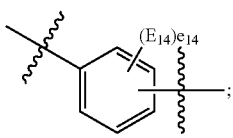

$E_1$ to $E_{14}$ are each independently selected from: hydrogen, deuterium, halogen, cyano, heteroaryl with 3-12 carbon atoms, aryl with 6-15 carbon atoms, trialkylsilyl with 3-9 carbon atoms, alkyl with 1-10 carbon atoms, haloalkyl with 1-10 carbon atoms, cycloalkyl with 3-10 carbon atoms, alkoxyl with 1-10 carbon atoms;

$e_1$ to $e_{14}$ are represented by $e_r$, $E_1$ to $E_{14}$ are represented by $E_r$, r is a variable representing any integer from 1 to 14, and $e_r$ represents the quantity of substituents $E_r$; when r is selected from 1, 2, 3, 4, 5, 6, 9, 13, or 14, $e_r$ is selected from 1, 2, 3, or 4; when r is selected from 7 or 11, $e_r$ is selected from 1, 2, 3, 4, 5, or 6; when r is 12, $e_r$ is selected from 1, 2, 3, 4, 5, 6, or 7; when r is selected from 8 or 10, $e_r$ is selected from 1, 2, 3, 4, 5, 6, 7, or 8; and when $e_r$ is greater than 1, any two $E_r$ are identical or different;

$K_3$ is selected from O, S, Se, $N(E_{15})$, $C(E_{16}E_{17})$, $Si(E_{18}E_{19})$; where $E_{15}$, $E_{16}$, $E_{17}$, $E_{18}$, and $E_{19}$ are each independently selected from: hydrogen, aryl with 6-15 carbon atoms, heteroaryl with 3-12 carbon atoms, alkyl with 1-10 carbon atoms, cycloalkyl with 3-10 carbon atoms, heterocycloalkyl with 2-10 carbon atoms;

each $K_4$ is independently selected from single bond, O, S, Se, $N(E_{20})$, $C(E_{21}E_{22})$, $Si(E_{23}E_{24})$; where $E_{20}$, $E_{21}$, $E_{22}$, $E_{23}$, and $E_{24}$ are each independently selected from: hydrogen, aryl with 6-15 carbon atoms, heteroaryl with 3-12 carbon atoms, alkyl with 1-10 carbon atoms, cycloalkyl with 3-10 carbon atoms.

In an alternative embodiment of the present disclosure, $R_1$ and $R_3$ are each independently selected from substituted or unsubstituted group $W_1$, and the unsubstituted group $W_1$ is selected from the following groups:

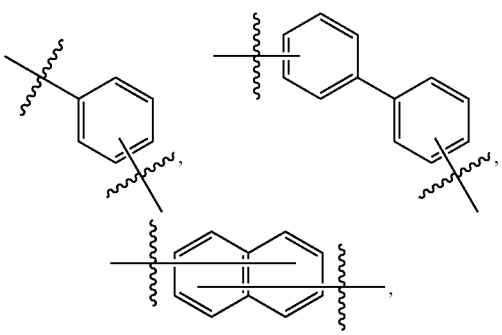

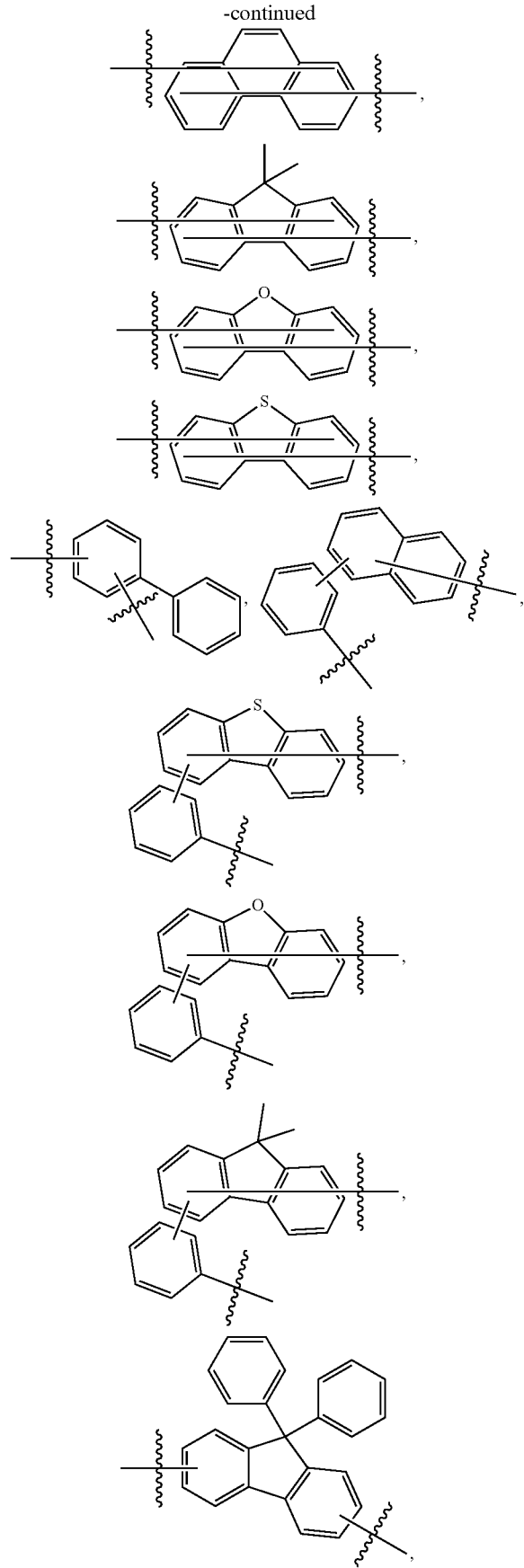
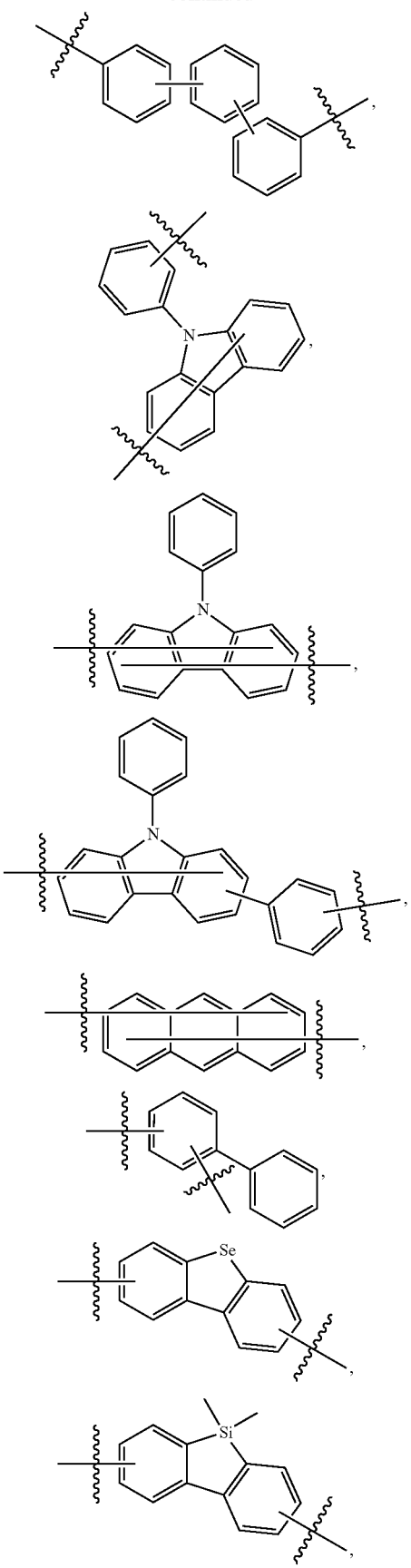

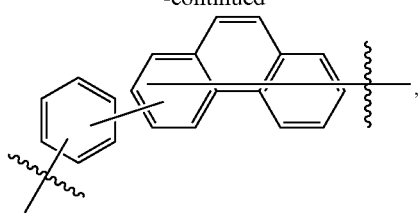

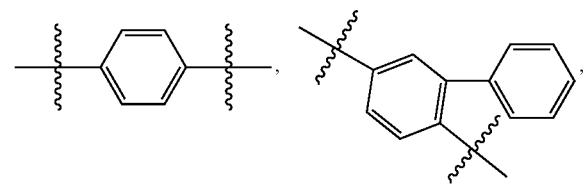

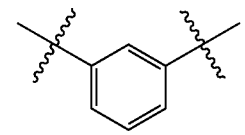

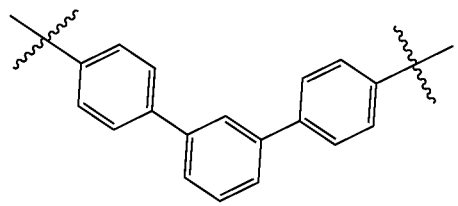

when the group $W_1$ is substituted by one or more substituents, the substituents of $W_1$ are each independently selected from the group consisting of deuterium, fluoro, chloro, cyano, methyl, ethyl, propyl, tert-butyl, trimethylsilyl, phenyl, naphthyl, dibenzofuryl, dibenzothienyl, carbazolyl; and when there is more than one substituent of the $W_1$, the substituents are identical or different.

In an alternative embodiment of the present disclosure, $R_2$, $R_4$, and $R_5$ are identical or different, and are each independently selected from substituted or unsubstituted aralkyl with 7-30 carbon atoms, substituted or unsubstituted heteroaralkyl with 2-30 carbon atoms, substituted or unsubstituted aryl with 6-30 carbon atoms, substituted or unsubstituted heteroaryl with 1-30 carbon atoms.

In an alternative embodiment of the present disclosure, $R_1$ and $R_3$ are identical or different, and are each independently selected from single bond, substituted or unsubstituted phenylene, substituted or unsubstituted biphenylene, substituted or unsubstituted terphenylene, substituted or unsubstituted chrysenylene, substituted or unsubstituted phenanthrylene, substituted or unsubstituted naphthylene, substituted or unsubstituted azulenylene, substituted or unsubstituted indenylene, substituted or unsubstituted pyridylene, substituted or unsubstituted pyrimidylene, substituted or unsubstituted triazinylene, substituted or unsubstituted imidazolylidene.

In an alternative embodiment of the present disclosure, $R_1$ and $R_3$ are identical or different, and are each independently selected from: substituted or unsubstituted phenylene, substituted or unsubstituted biphenylene, substituted or unsubstituted terphenylene, substituted or unsubstituted anthrylene, substituted or unsubstituted phenanthrylene, substituted or unsubstituted naphthylene, substituted or unsubstituted 9,9-dimethylfluorenylidene, substituted or unsubstituted dibenzofurylene, substituted or unsubstituted dibenzothienylene, substituted or unsubstituted carbazolylidene, or a subunit group formed by linking two or three of the subunits through a single bond;

the "substituted" means to be independently substituted by substituent(s) selected from the following groups: deuterium, cyano, fluoro, chloro, methyl, ethyl, propyl, tert-butyl, phenyl, naphthyl, carbazolyl, dibenzofuryl, or dibenzothienyl; and when there are a plurality of substituents, the substituents are identical or different.

In an alternative embodiment of the present disclosure, $R_1$ and $R_3$ are each independently selected from any one of the following groups:

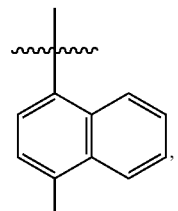

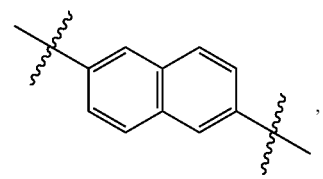

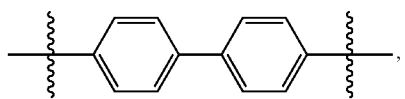

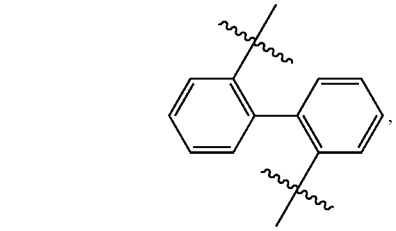

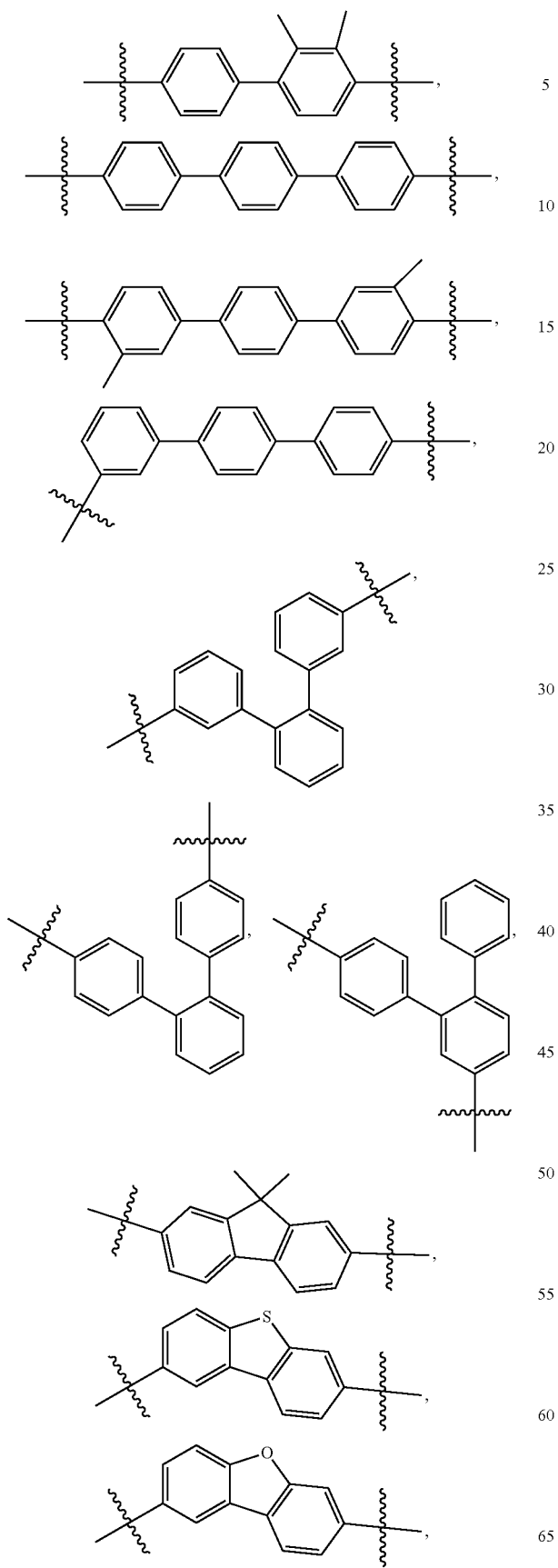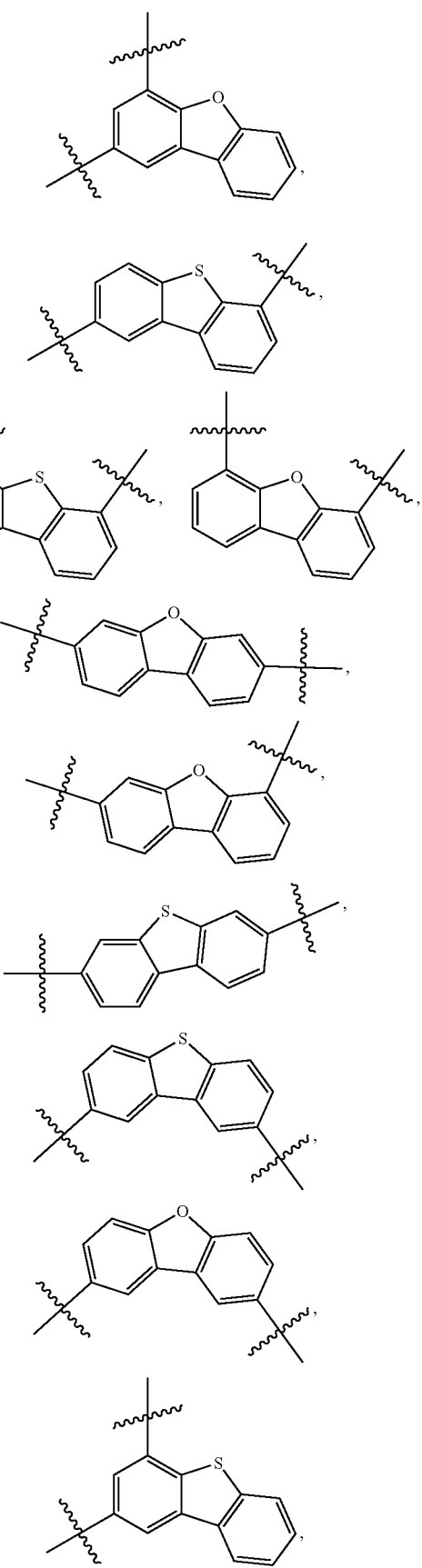

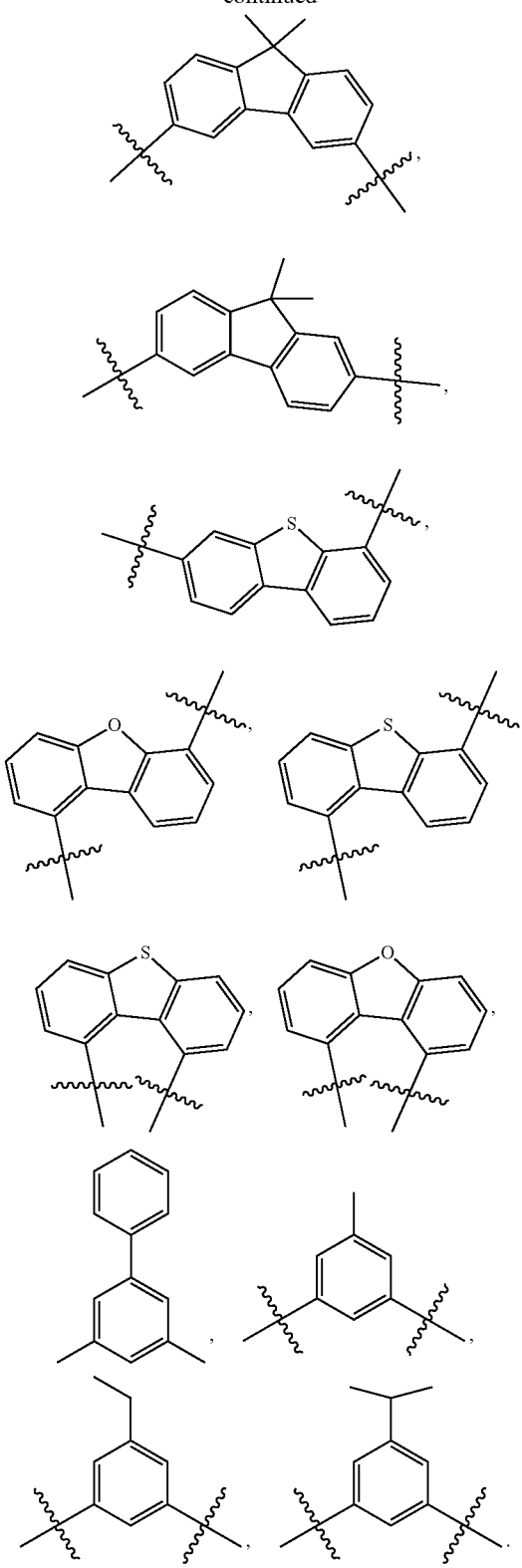

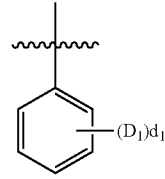

Chemical formula (i-1)

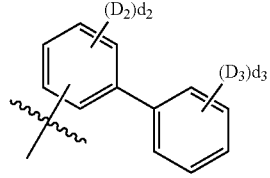

Chemical formula (i-2)

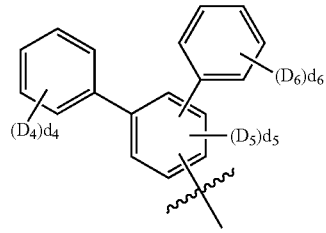

Chemical formula (i-3)

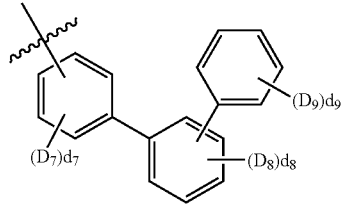

Chemical formula (i-4)

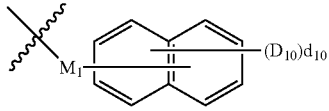

Chemical formula (i-5)

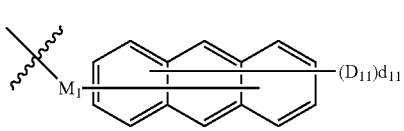

Chemical formula (i-6)

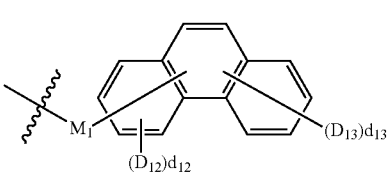

Chemical formula (i-7)

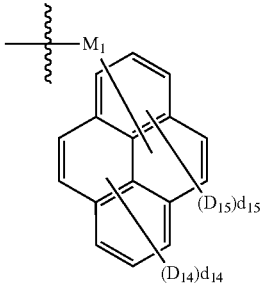

Chemical formula (i-8)

In an alternative embodiment of the present disclosure, $R_2$, $R_4$, and $R_5$ are identical to or different from each other, and are each independently selected from the group consisting of groups represented by chemical formula i-1 to chemical formula i-11:

-continued

Chemical formula (i-9)

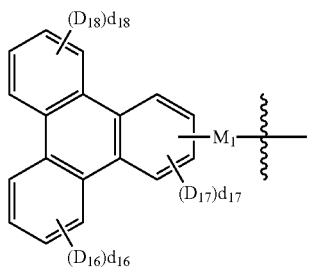

Chemical formula (i-10)

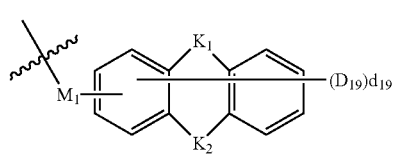

Chemical formula (i-11)

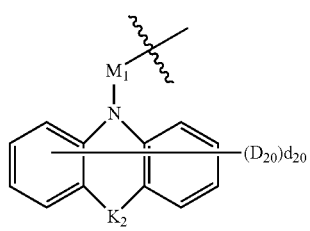

where M₁ is selected from single bond or

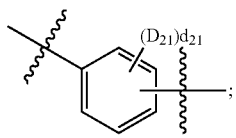

D₁ is selected from: hydrogen, deuterium, fluoro, chloro, bromo, cyano, trialkylsilyl with 3-12 carbon atoms, alkyl with 1-10 carbon atoms, haloalkyl with 1-10 carbon atoms, cycloalkyl with 3-10 carbon atoms, alkoxyl with 1-10 carbon atoms, alkylthio with 1-10 carbon atoms;

D₂ to D₉, and D₂₁ are each independently selected from: hydrogen, deuterium, fluoro, chloro, bromo, cyano, trialkylsilyl with 3-12 carbon atoms, alkyl with 1-10 carbon atoms, haloalkyl with 1-10 carbon atoms, cycloalkyl with 3-10 carbon atoms, alkoxyl with 1-10 carbon atoms, heteroaryl with 3-12 carbon atoms;

D₁₀ to D₂₀ are each independently selected from: hydrogen, deuterium, fluoro, chloro, bromo, cyano, trialkylsilyl with 3-12 carbon atoms, alkyl with 1-10 carbon atoms, haloalkyl with 1-10 carbon atoms, cycloalkyl with 3-10 carbon atoms, alkoxyl with 1-10 carbon atoms, aryl with 6-15 carbon atoms, heteroaryl with 3-12 carbon atoms;

$d_1$ to $d_{21}$ are represented by $d_k$, $D_1$ to $D_{21}$ are represented by $D_k$, k is a variable representing any integer from 1 to 21, and $d_k$ represents the quantity of substituents $D_k$; where when k is selected from 5 or 17, $d_k$ is selected from 1, 2, or 3; when k is selected from 2, 7, 8, 12, 15, 16, 18, or 21, $d_k$ is selected from 1, 2, 3, or 4; when k is selected from 1, 3, 4, 6, 9, or 14, $d_k$ is selected from 1, 2, 3, 4, or 5; when k is 13, $d_k$ is selected from 1, 2, 3, 4, 5, or 6; when k is selected from 10 or 19, $d_k$ is selected from 1, 2, 3, 4, 5, 6, or 7; when k is 20, $d_k$ is selected from 1, 2, 3, 4, 5, 6, 7, or 8; when k is 11, $d_k$ is selected from 1, 2, 3, 4, 5, 6, 7, 8, or 9; and when $d_k$ is greater than 1, any two $D_k$ are identical or different;

K₁ is independently selected from O, S, N(D₂₂), C(D₂₃D₂₄), Si(D₂₅D₂₆); where D₂₂, D₂₃, D₂₄, D₂₅, and D₂₆ are each independently selected from: aryl with 6-15 carbon atoms, heteroaryl with 3-12 carbon atoms, alkyl with 1-10 carbon atoms, cycloalkyl with 3-10 carbon atoms;

K₂ is selected from single bond, O, S, N(D₂₇), C(D₂₈D₂₉), Si(D₃₀D₃₁); where D₂₇, D₂₈, D₂₉, D₃₀, and D₃₁ are each independently selected from aryl with 6-15 carbon atoms, heteroaryl with 3-12 carbon atoms, alkyl with 1-10 carbon atoms, cycloalkyl with 3-10 carbon atoms.

In an alternative embodiment of the present disclosure, R₂, R₄, and R₅ are identical to or different from each other, and are each independently selected from substituted or unsubstituted group Y₁, the unsubstituted group Y₁ is selected from the group consisting of the following groups:

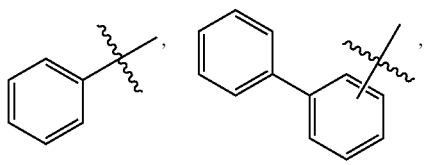

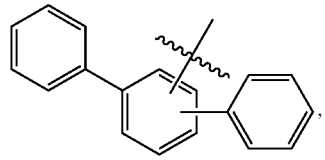

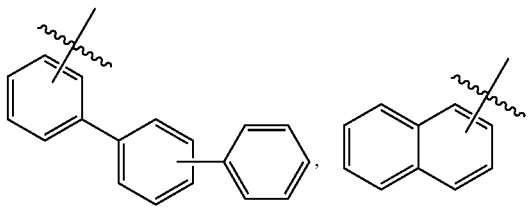

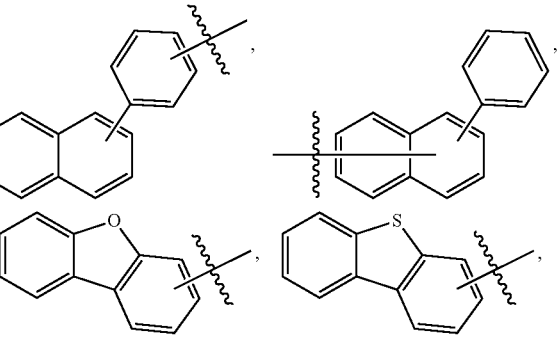

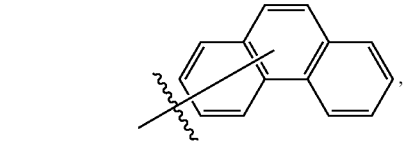

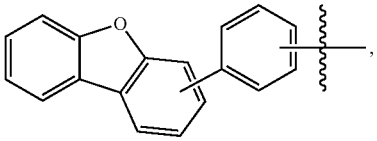

-continued

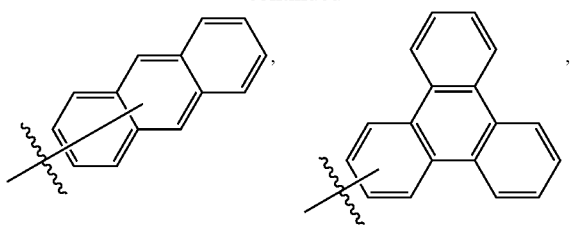

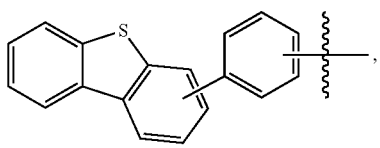

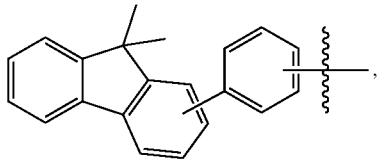

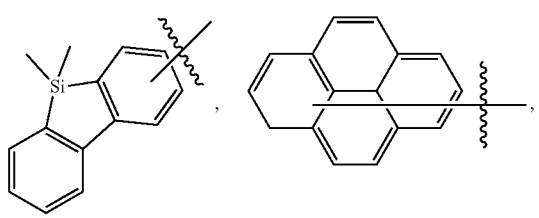

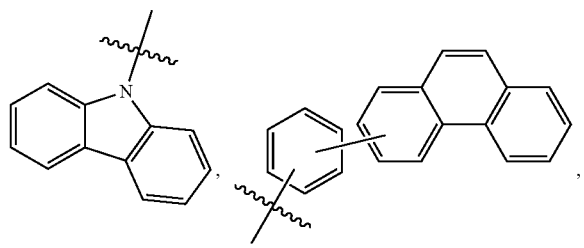

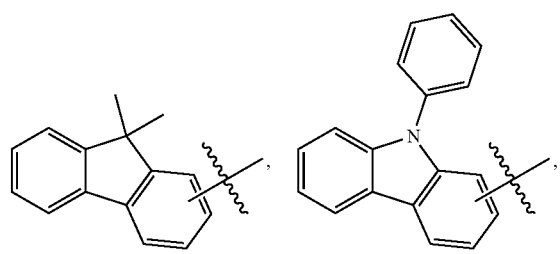

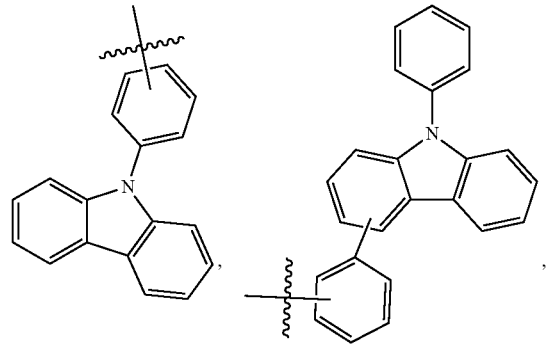

-continued

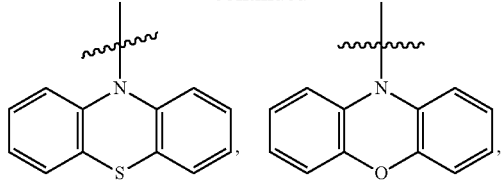

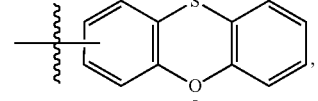

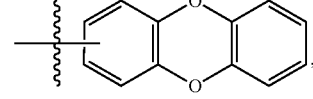

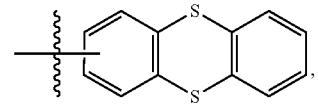

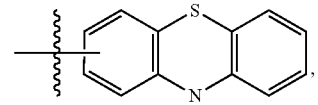

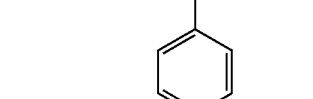

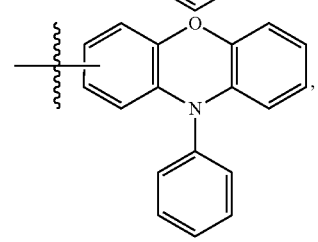

when the group $Y_1$ is substituted by one or more substituents, the substituents of $Y_1$ are each independently selected from the group consisting of deuterium, fluoro, chloro, cyano, methyl, ethyl, propyl, isopropyl, tert-butyl, trimethylsilyl, phenyl, naphthyl, dibenzothienyl and dibenzofuryl; and when there is more than one substituent of the $Y_1$, the substituents are identical or different.

In an alternative embodiment of the present disclosure, $R_2$, $R_4$, and $R_5$ are identical or different, and are each independently selected from: substituted or unsubstituted phenyl, substituted or unsubstituted biphenyl, substituted or unsubstituted terphenyl, substituted or unsubstituted anthryl, substituted or unsubstituted phenanthryl, substituted or unsubstituted naphthyl, substituted or unsubstituted 9,9-dimethylfluorenyl, substituted or unsubstituted dibenzofuryl, substituted or unsubstituted dibenzothienyl, substituted or unsubstituted carbazolyl, or a group formed by linking two or three of the aforementioned groups through a single bond;

the "substituted" means to be independently substituted by substituent(s) selected from the following groups: deuterium, cyano, fluoro, chloro, methyl, ethyl, propyl, tert-butyl, phenyl, naphthyl, carbazolyl, dibenzofuryl, or dibenzothienyl;

when there are a plurality of substituents, the substituents are identical or different.

In an alternative embodiment of the present disclosure, $R_2$, $R_4$ and $R_5$ are each independently selected from any one of the following groups:

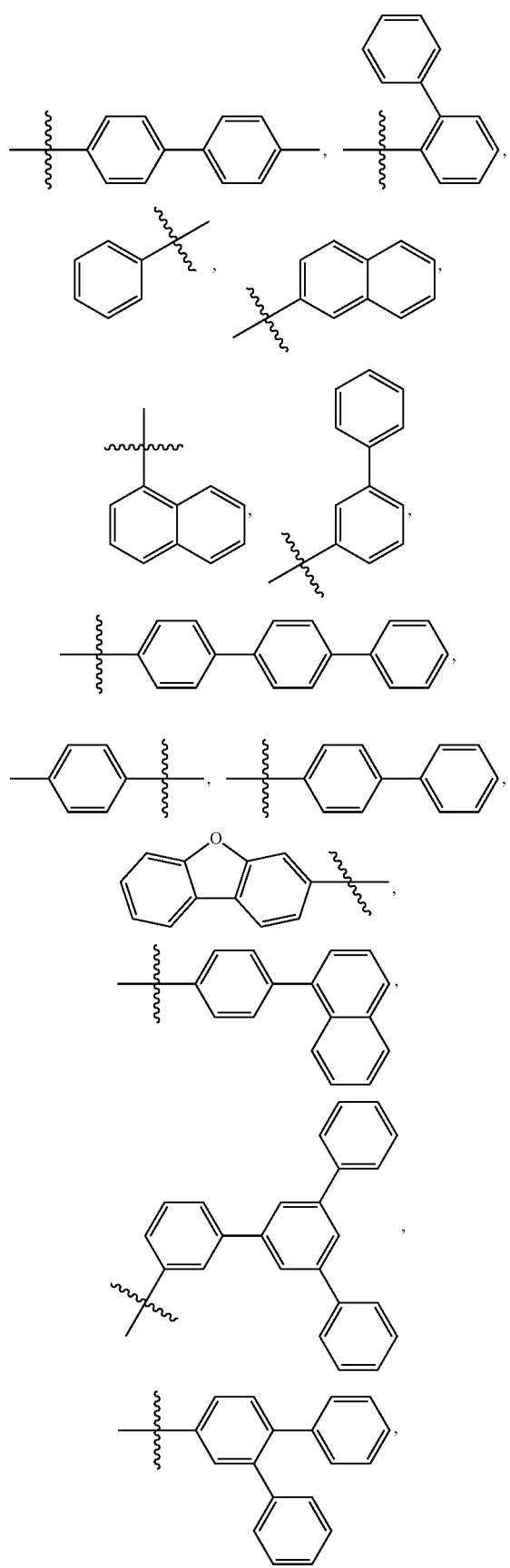
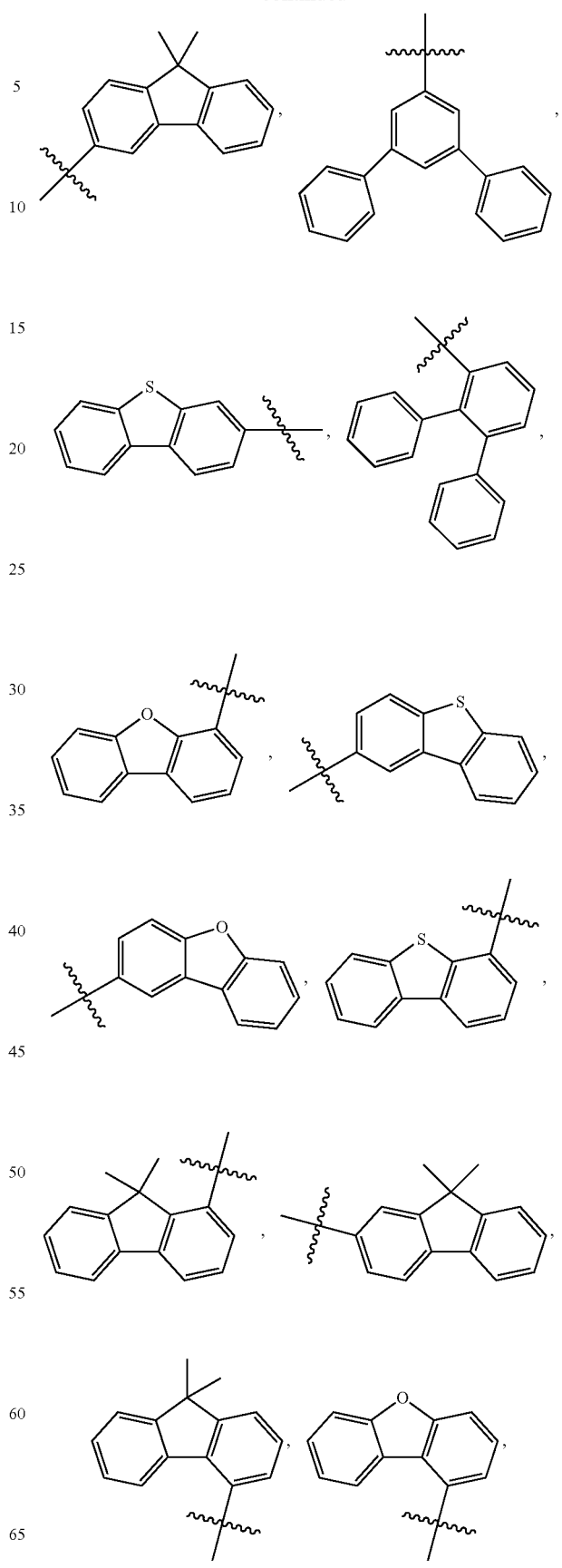

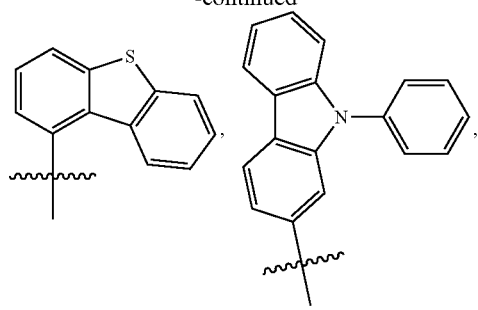
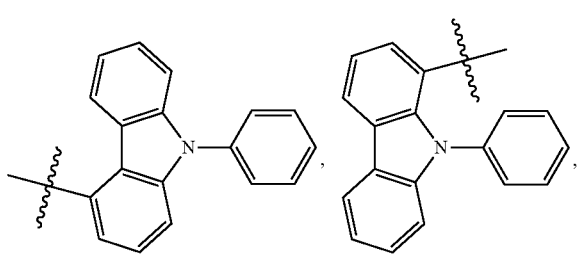
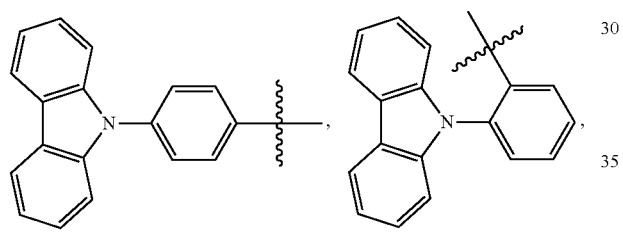
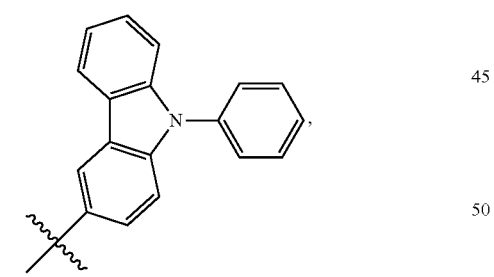
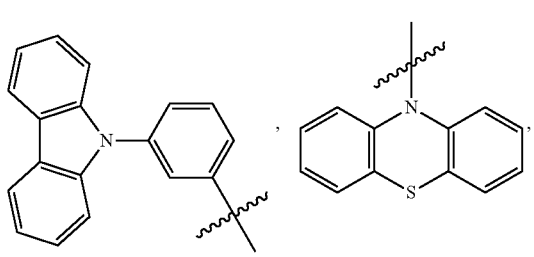
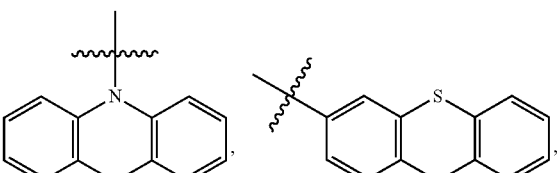
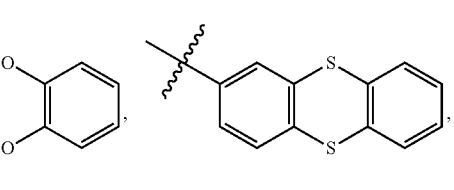
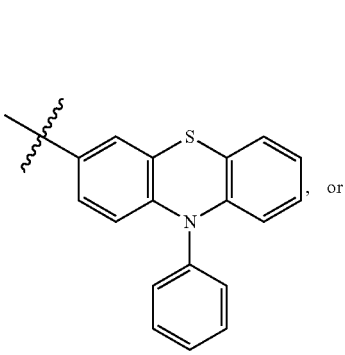, or
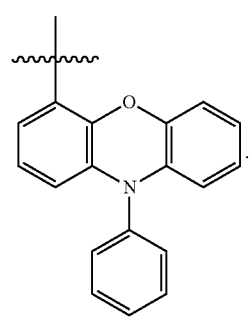
In an alternative embodiment of the present disclosure, the chemical formula 1 is, but is not limited to, one of the following structures:

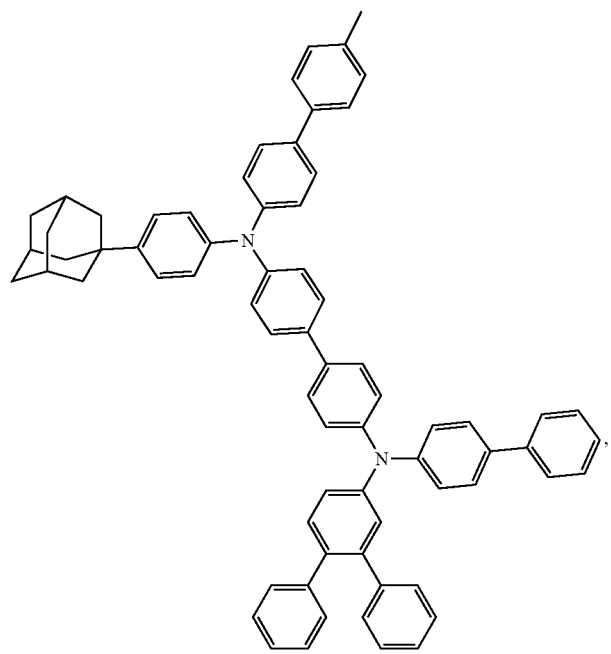
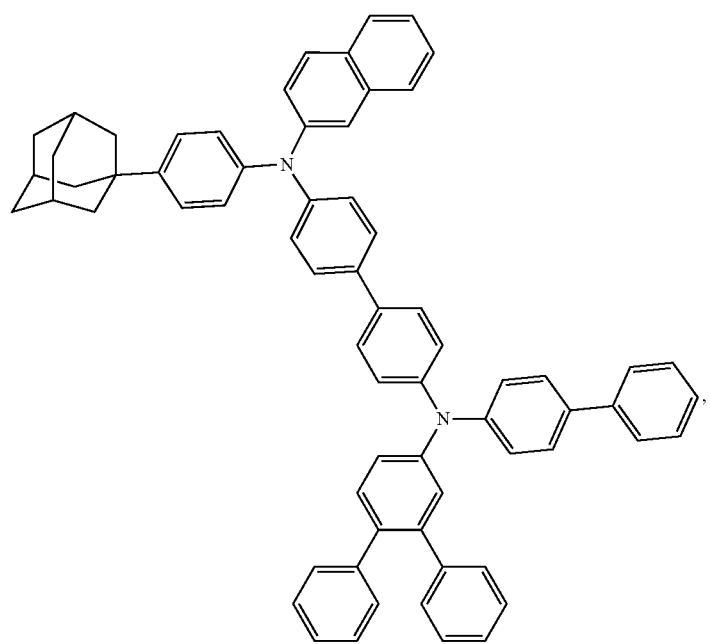

-continued
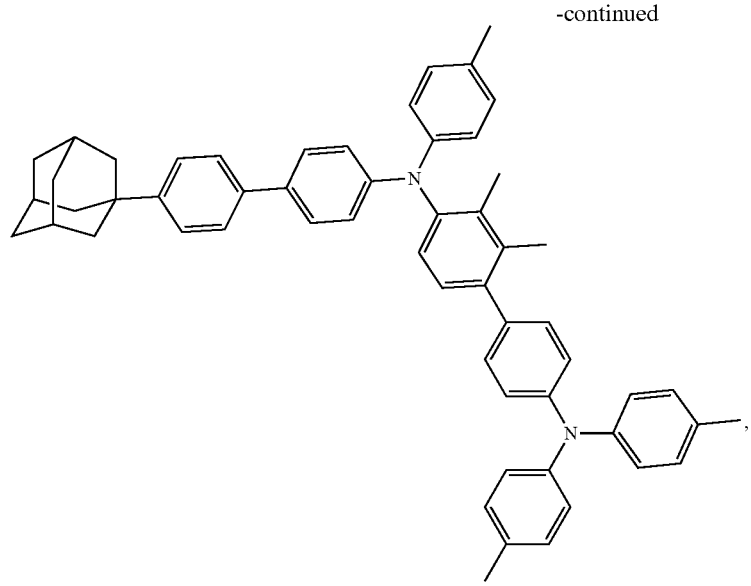
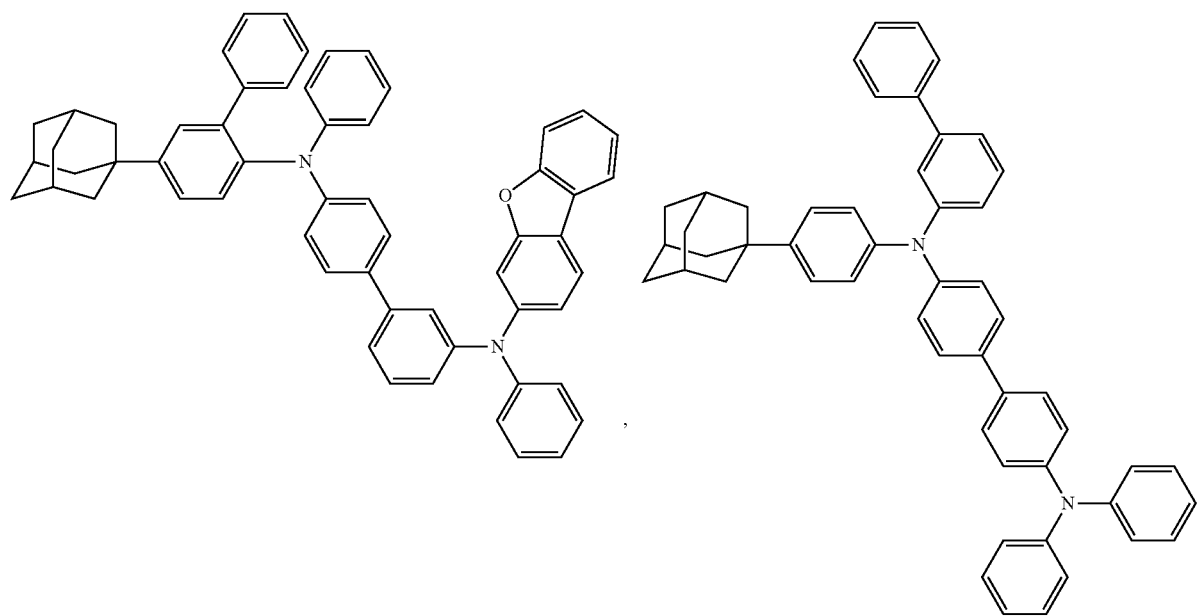
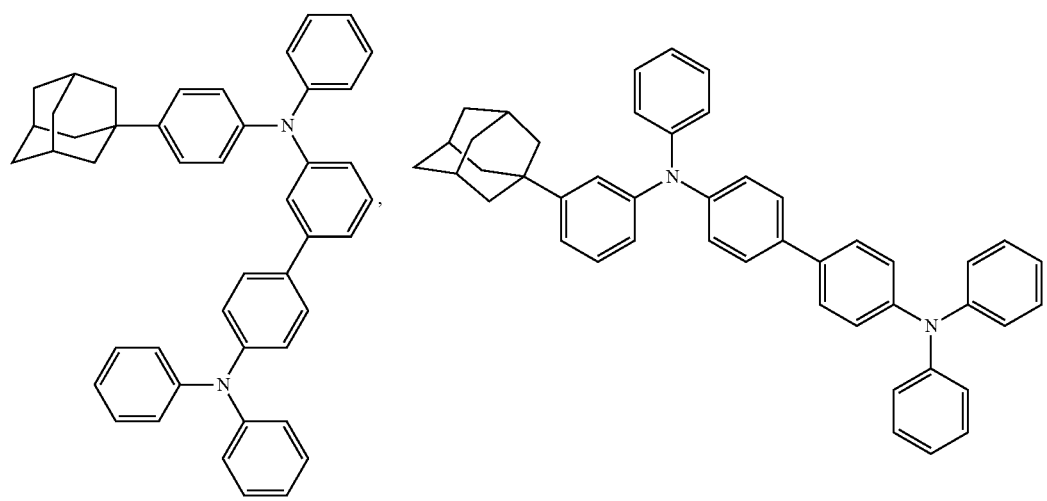

-continued
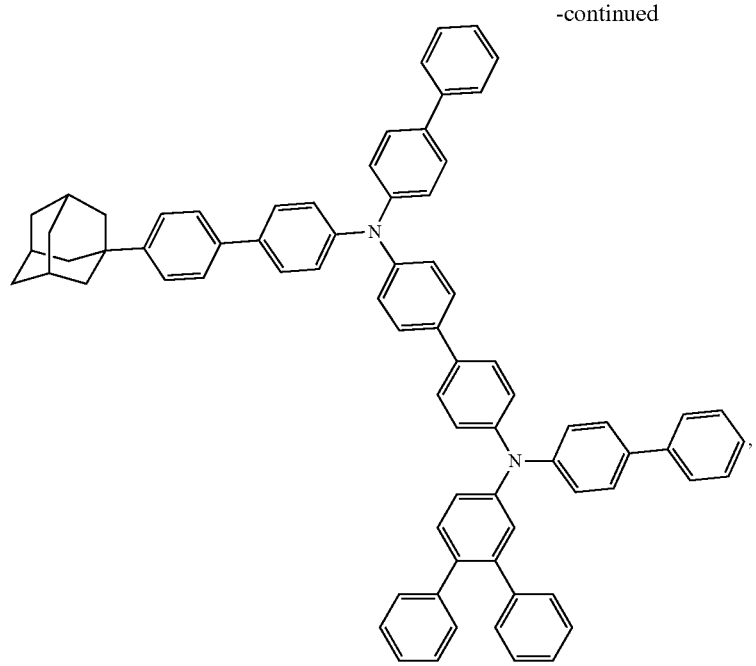
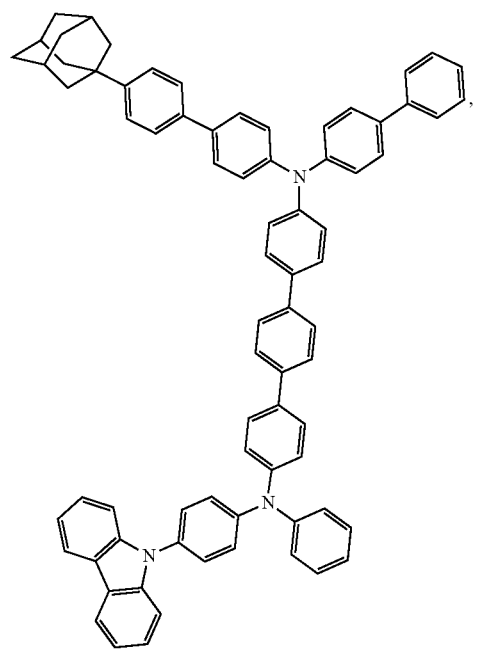

-continued
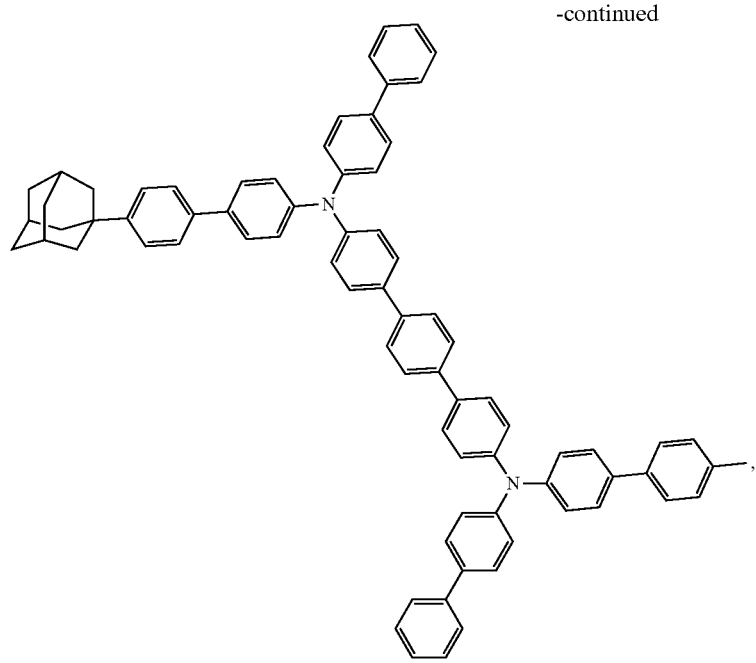
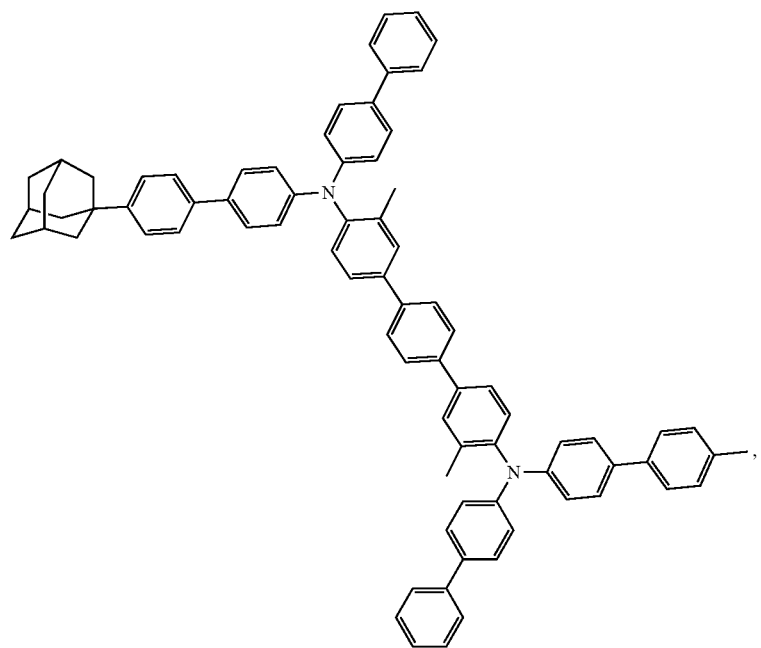

-continued
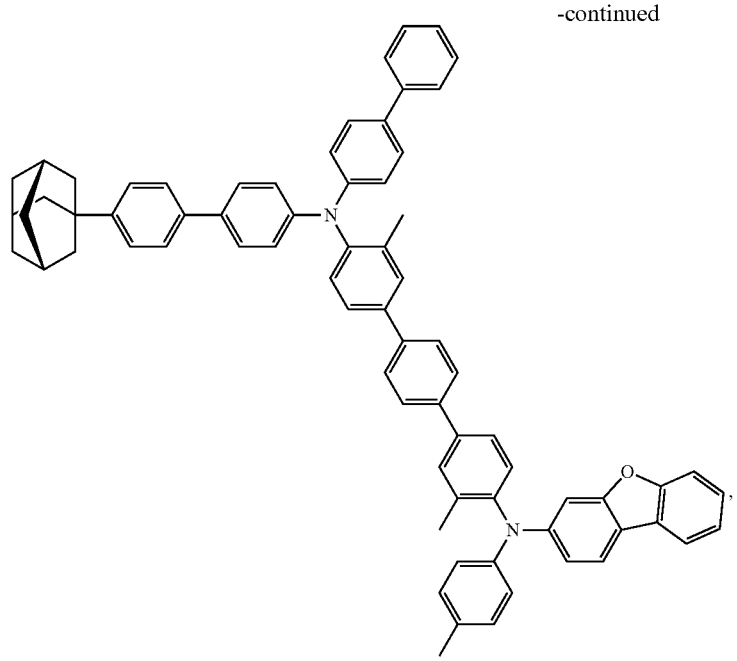
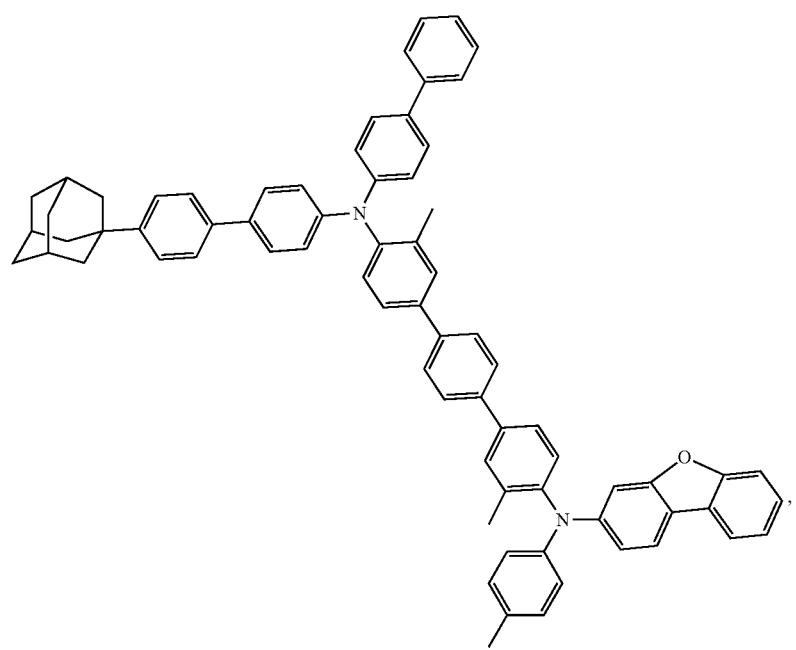

-continued
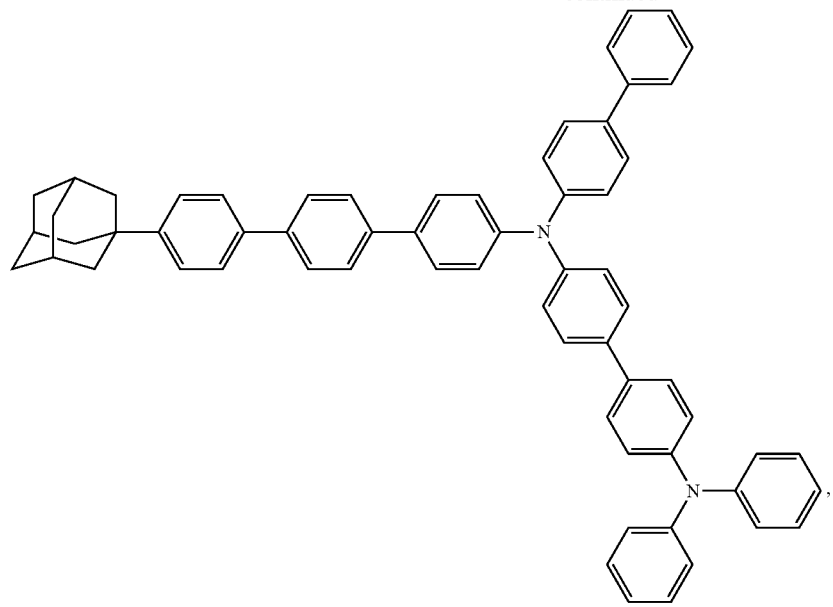
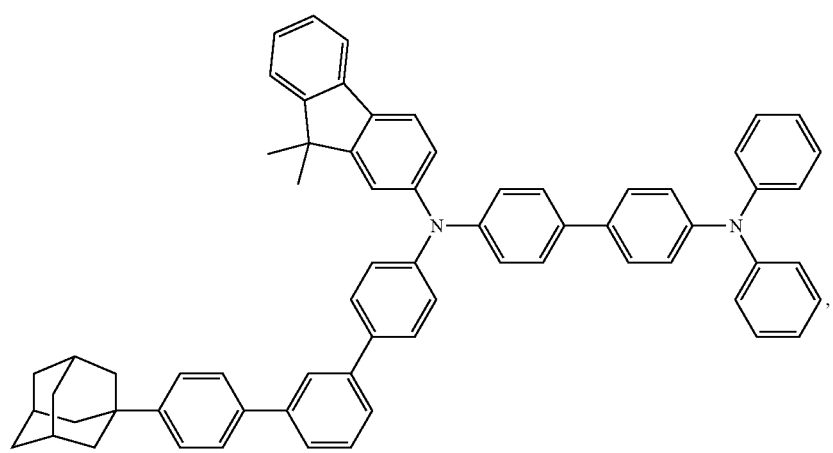
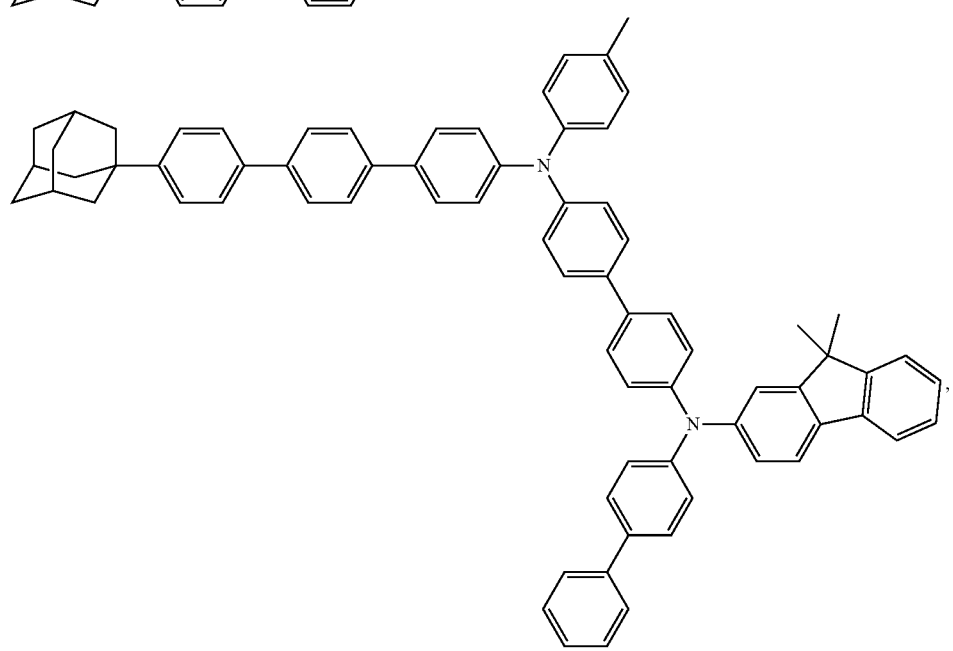

-continued
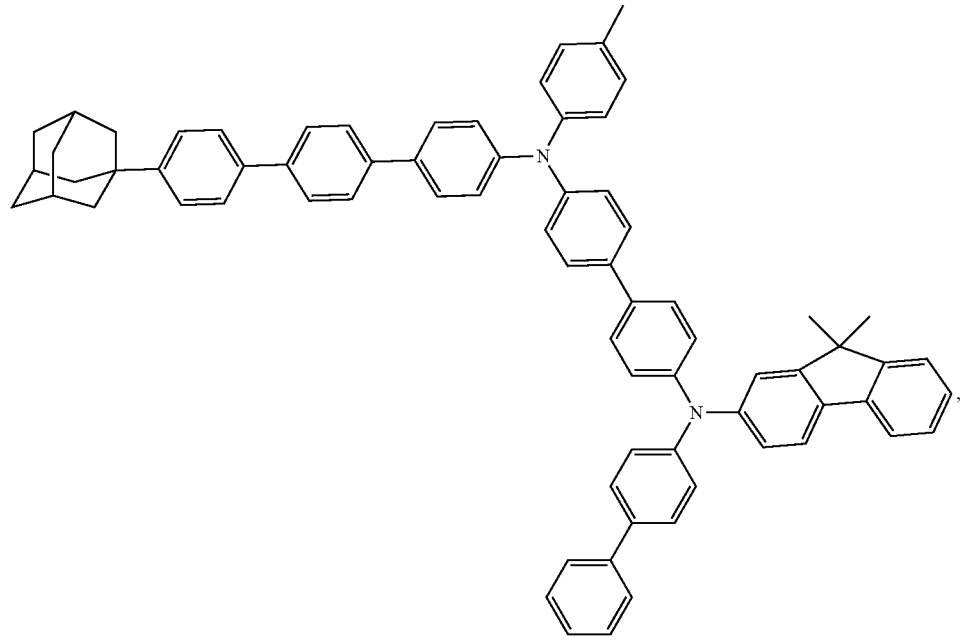
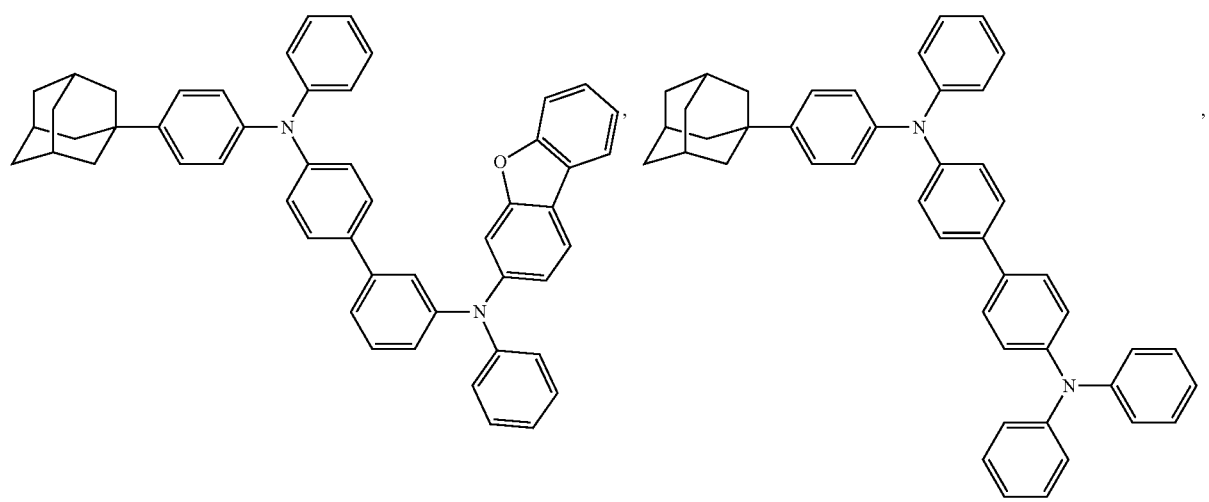
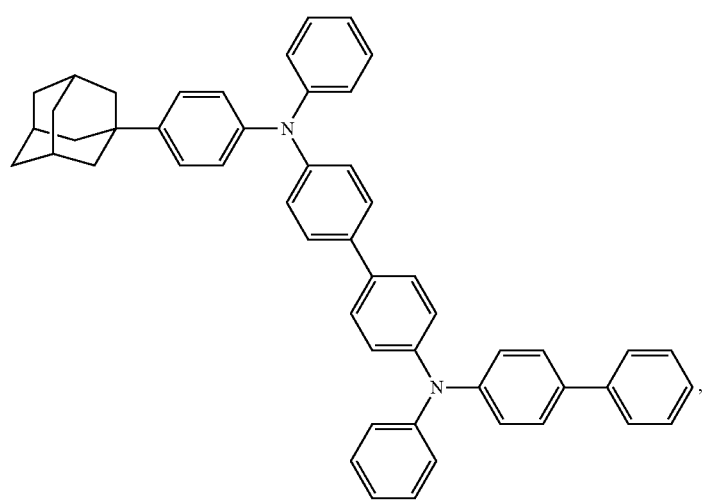

-continued
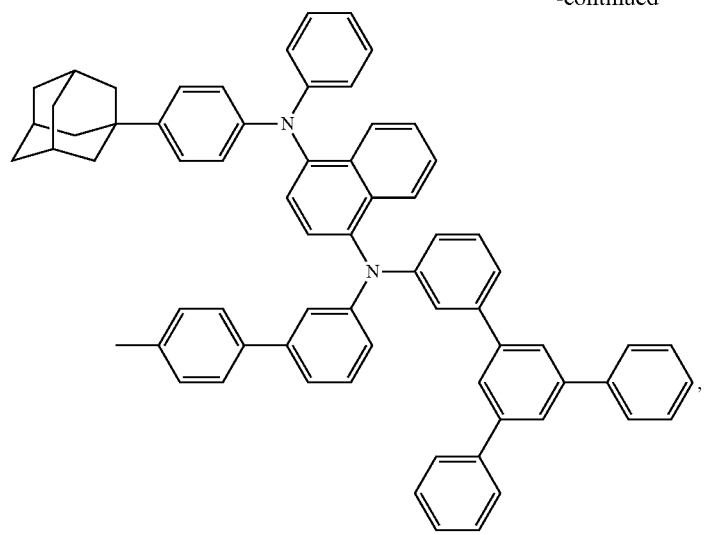
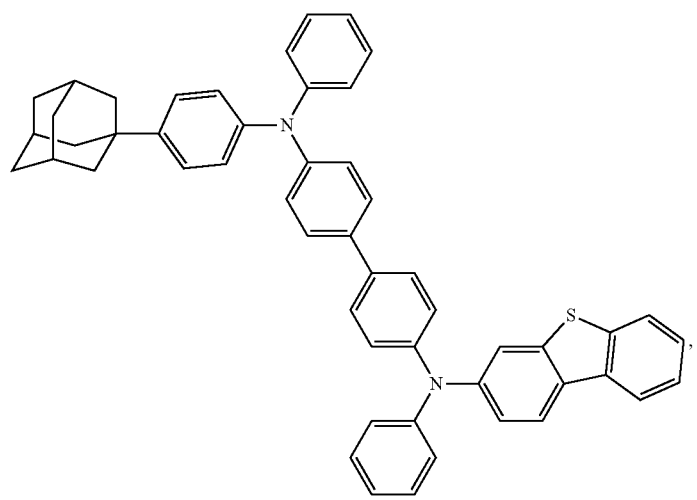
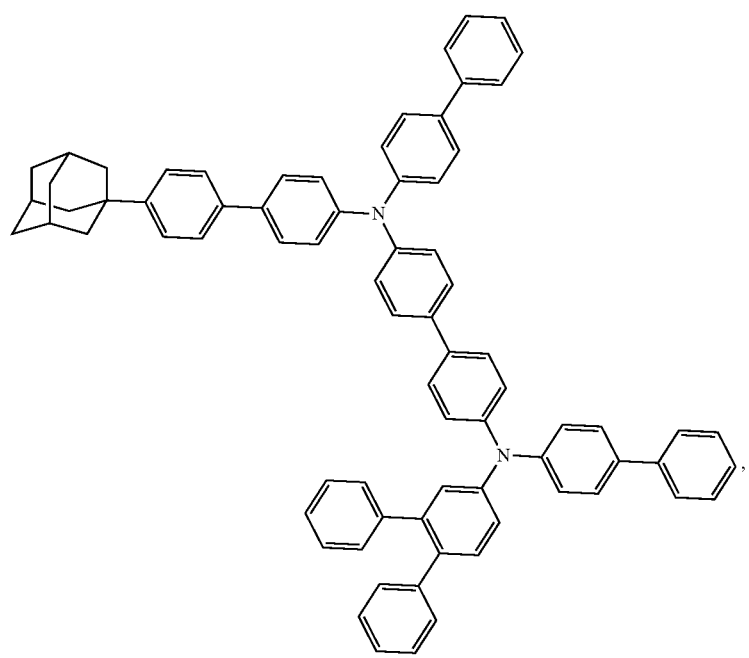

-continued
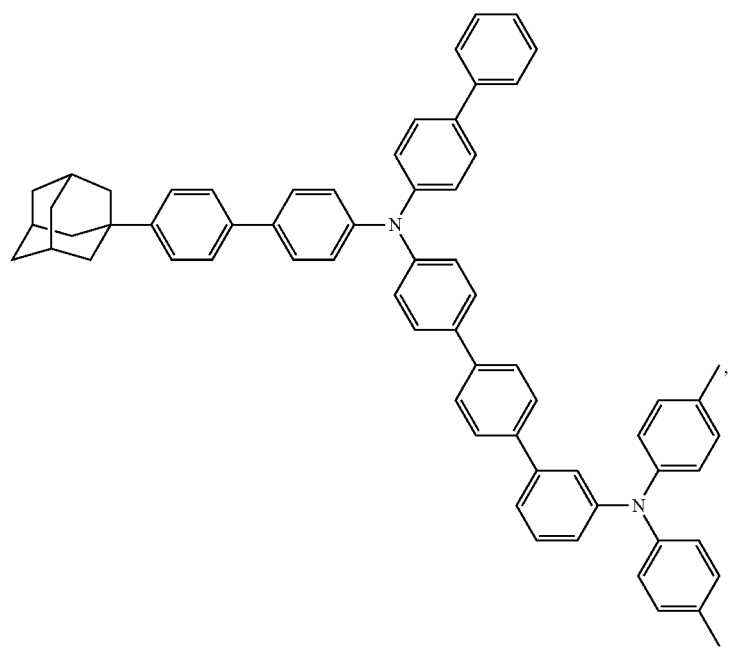
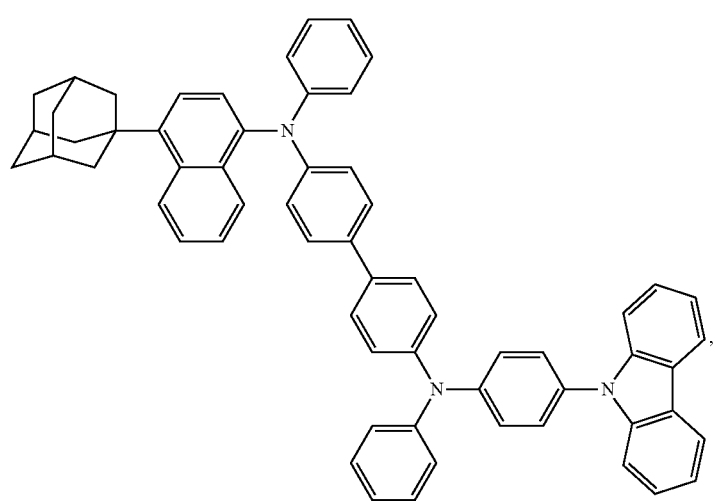

-continued
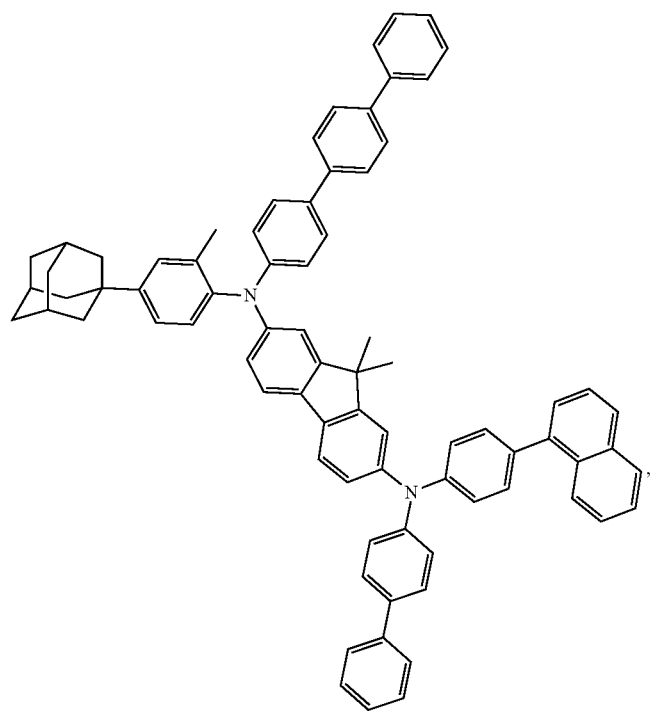
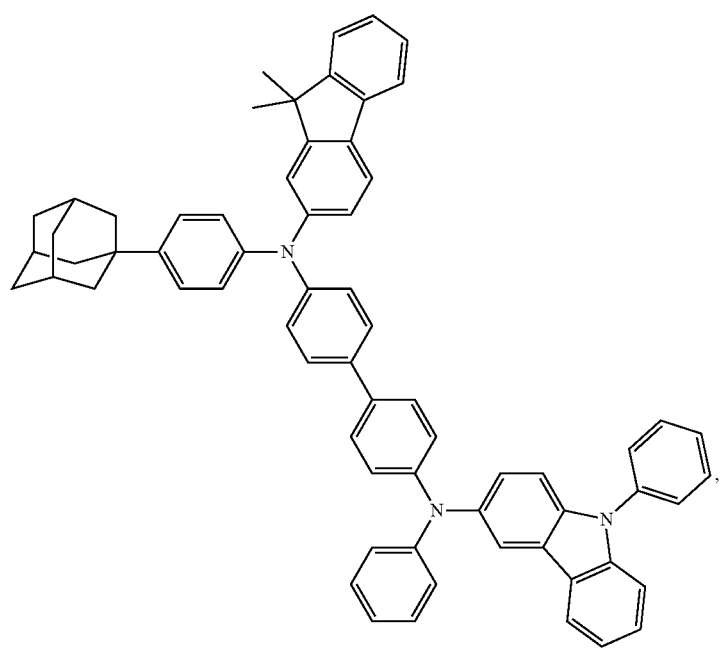
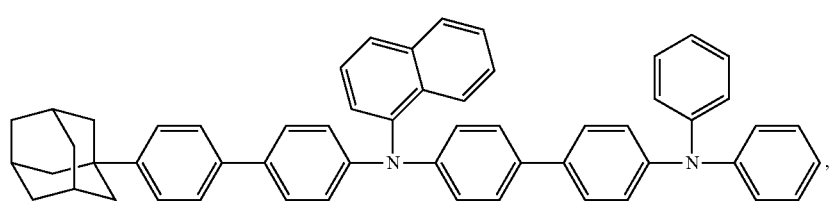

-continued
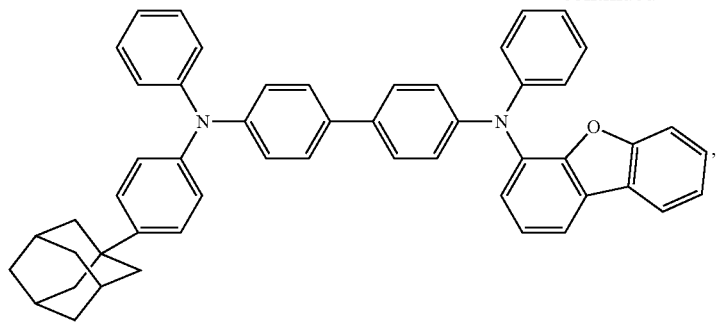
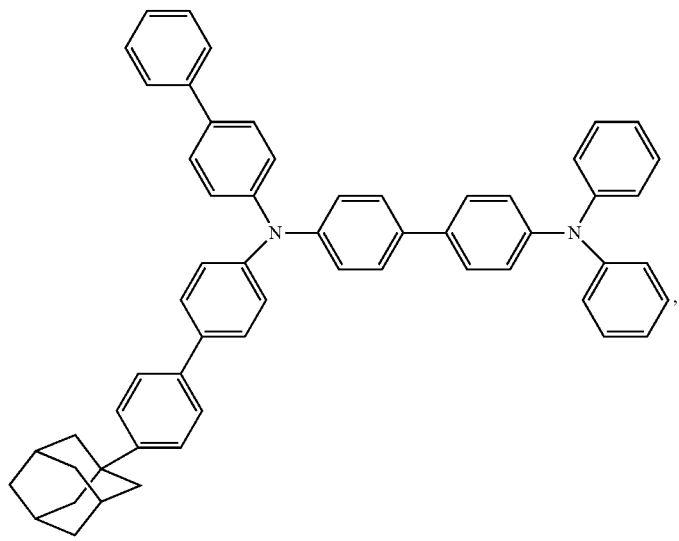
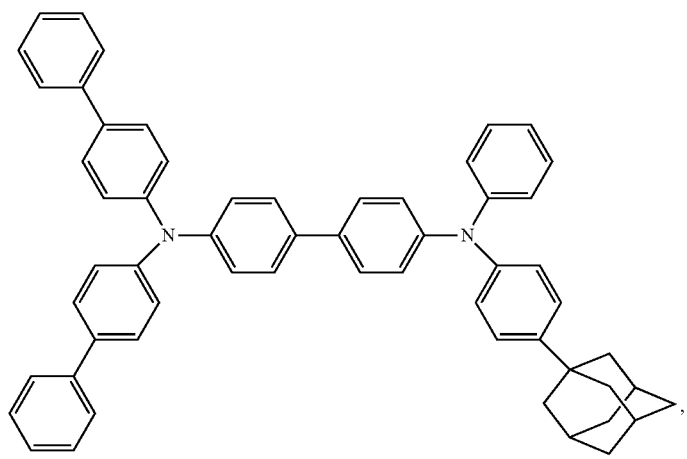

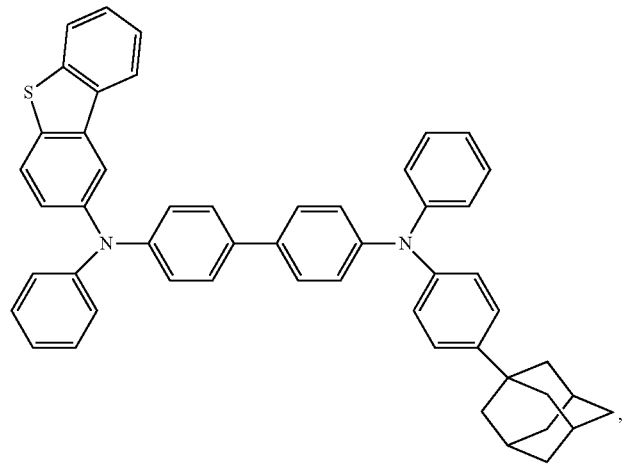
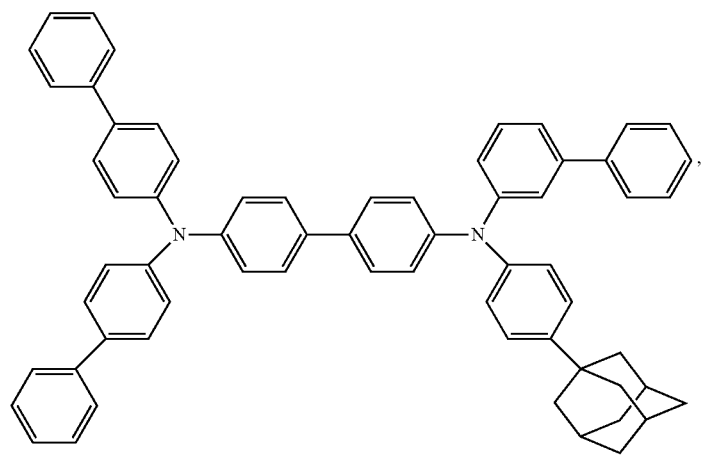
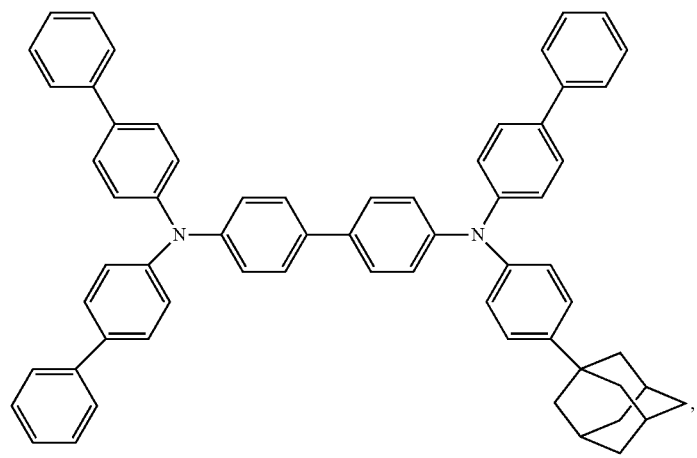

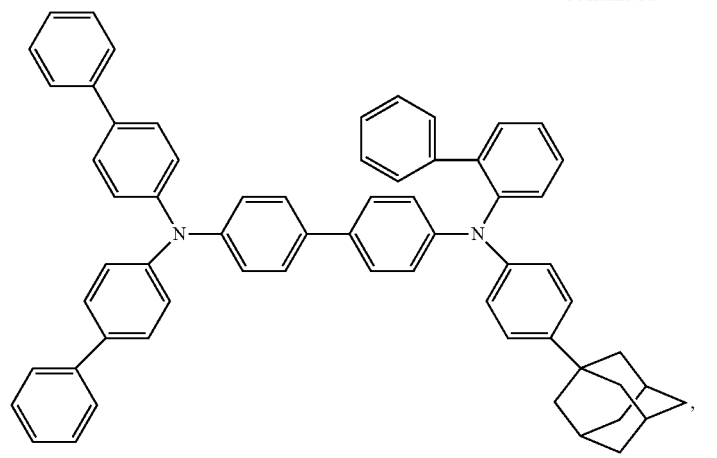
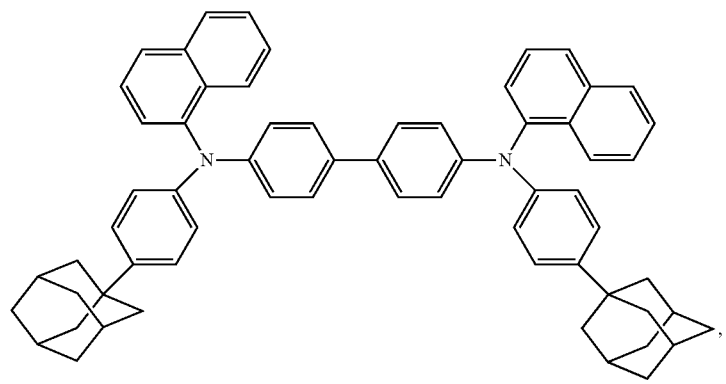
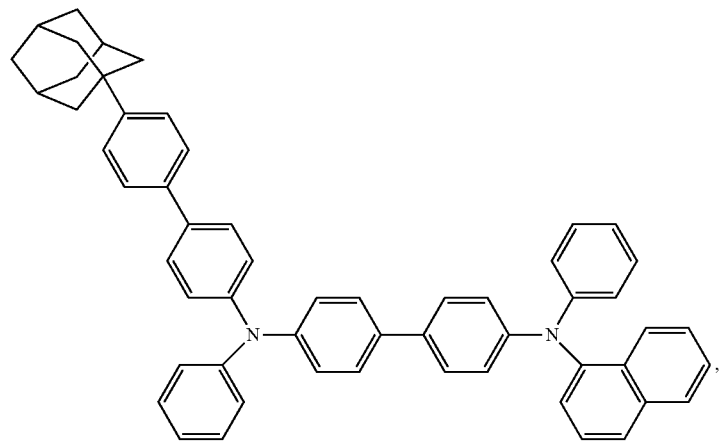
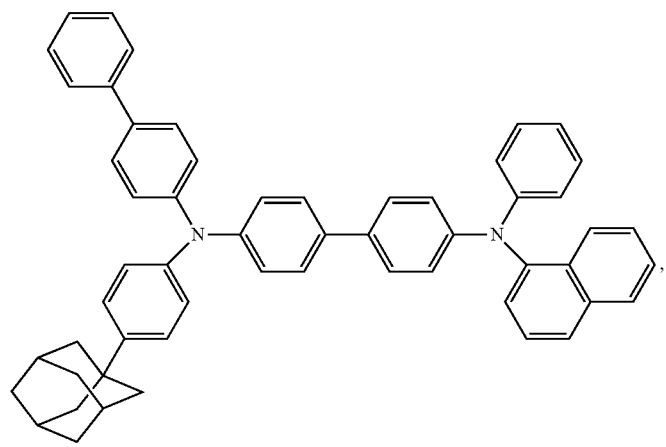

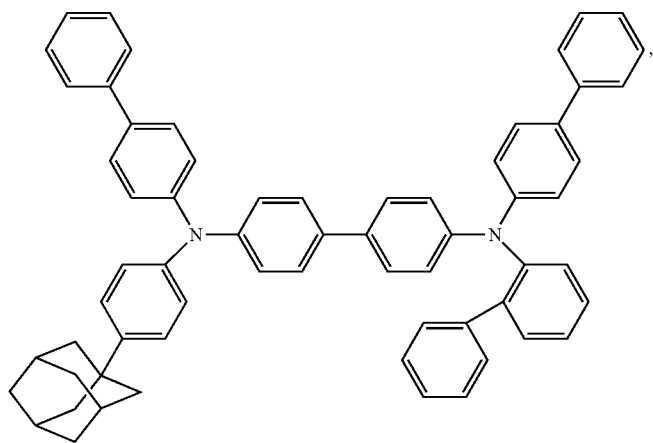
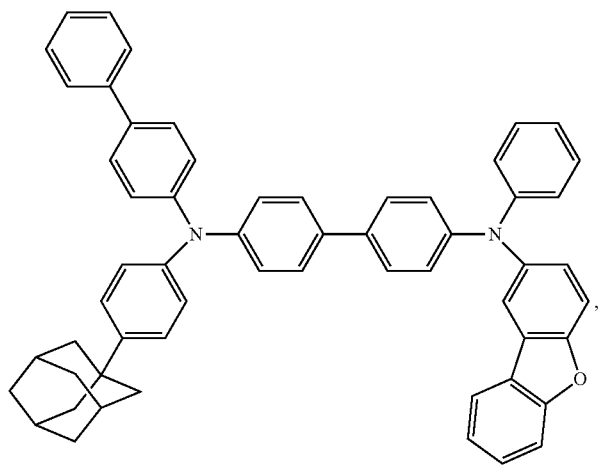
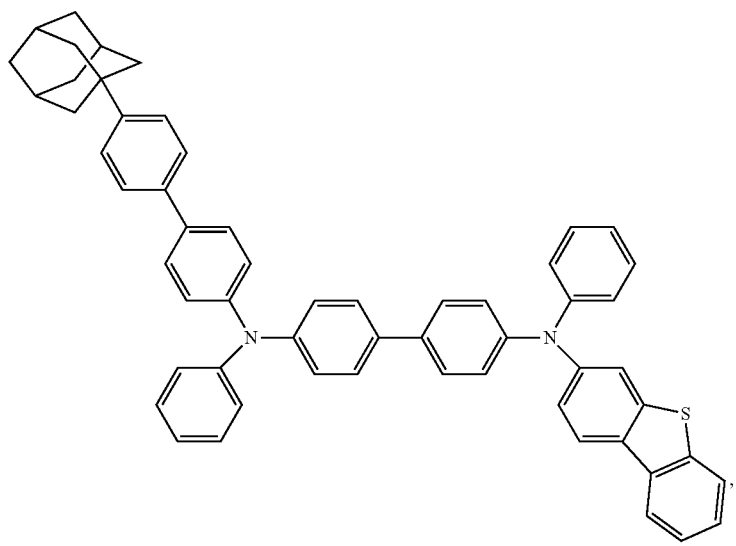

-continued
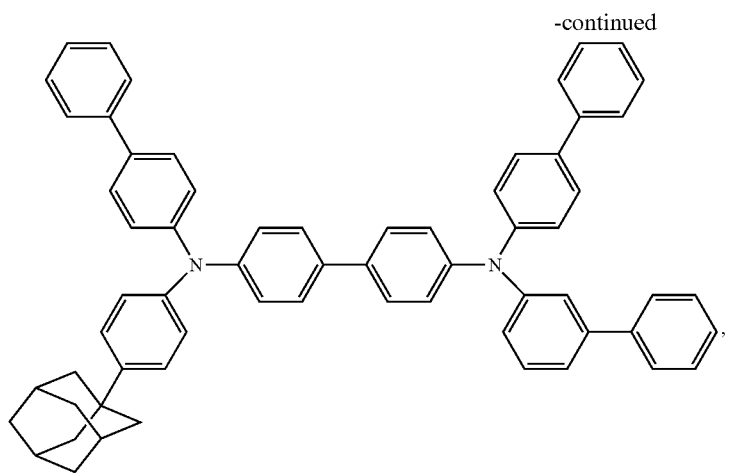
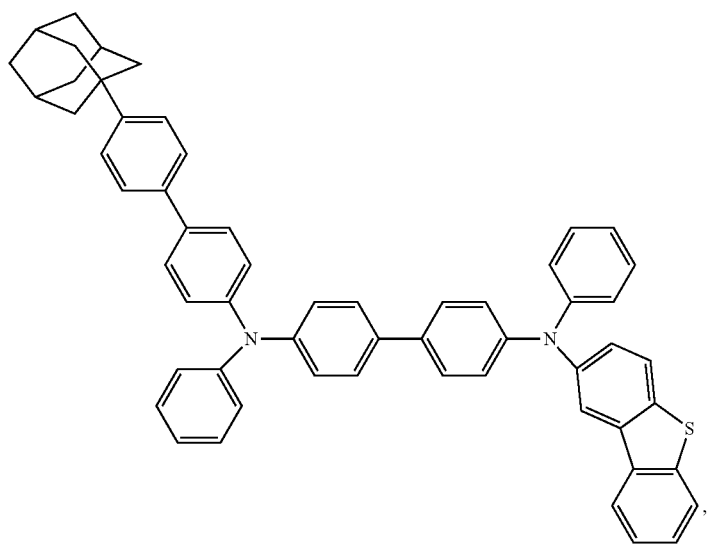
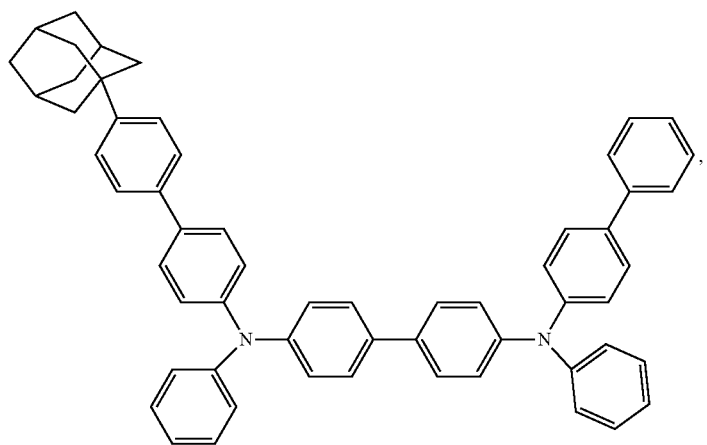

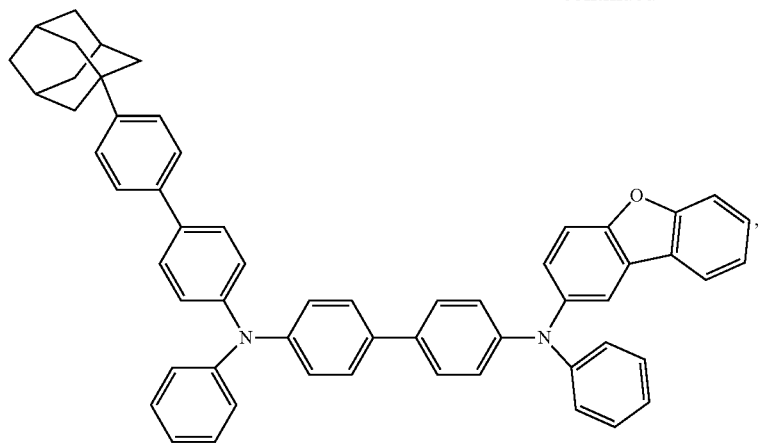
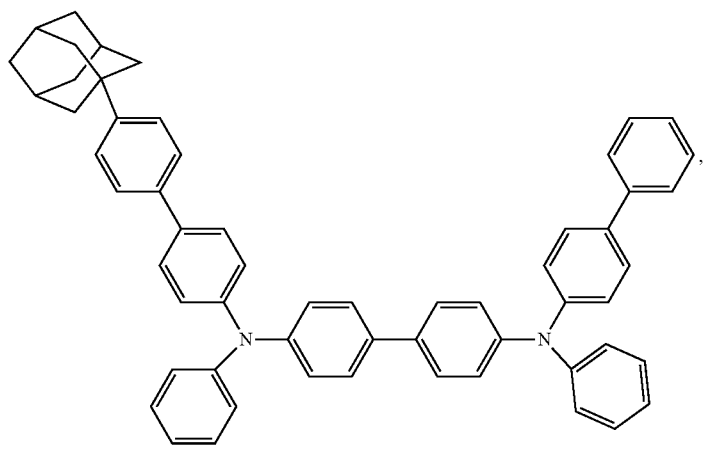
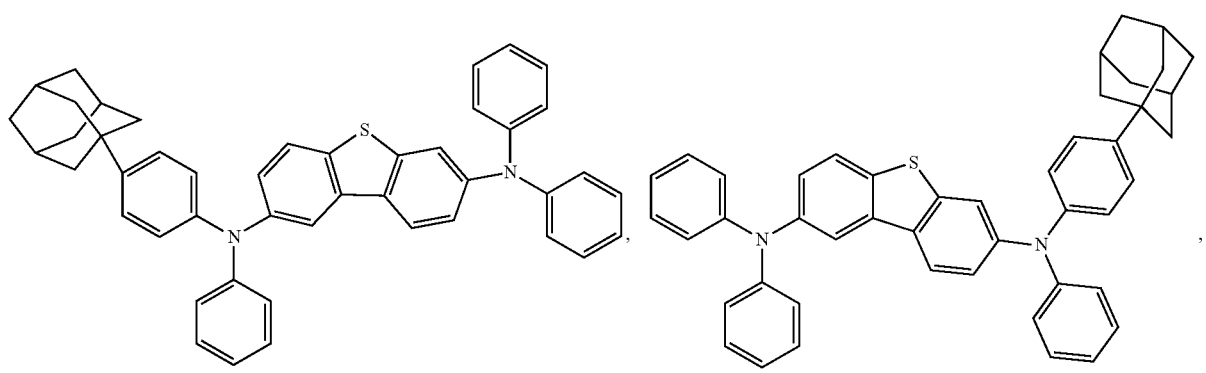
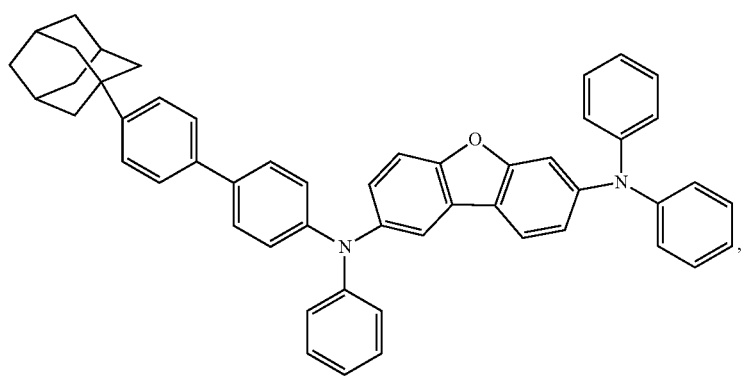

-continued
61 62
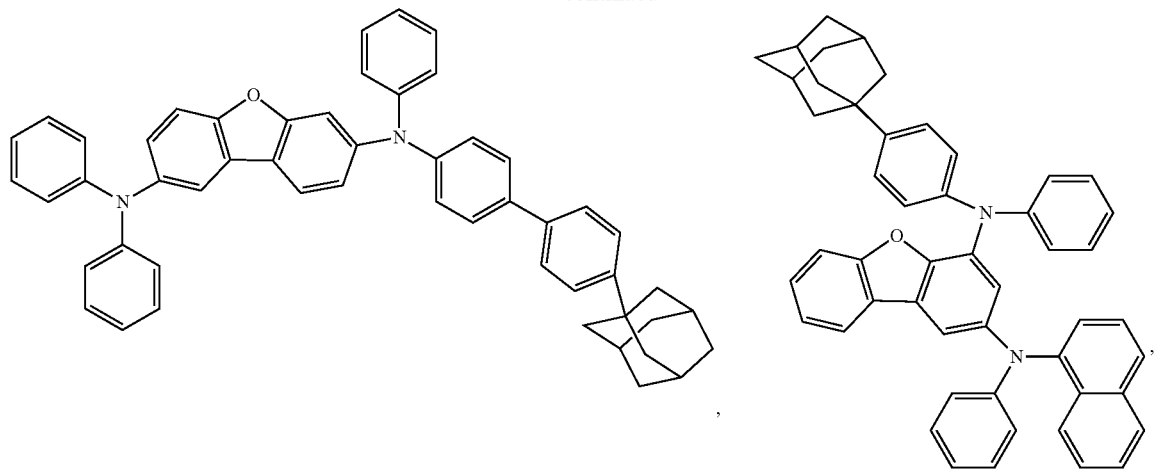
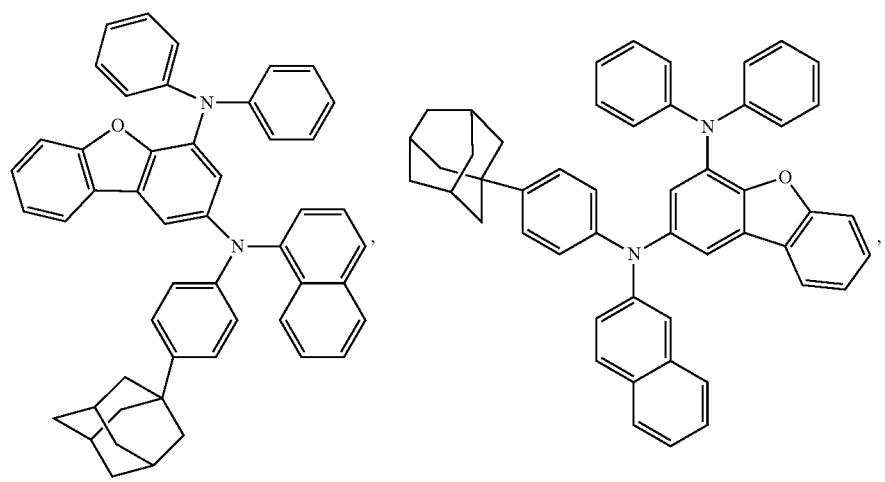
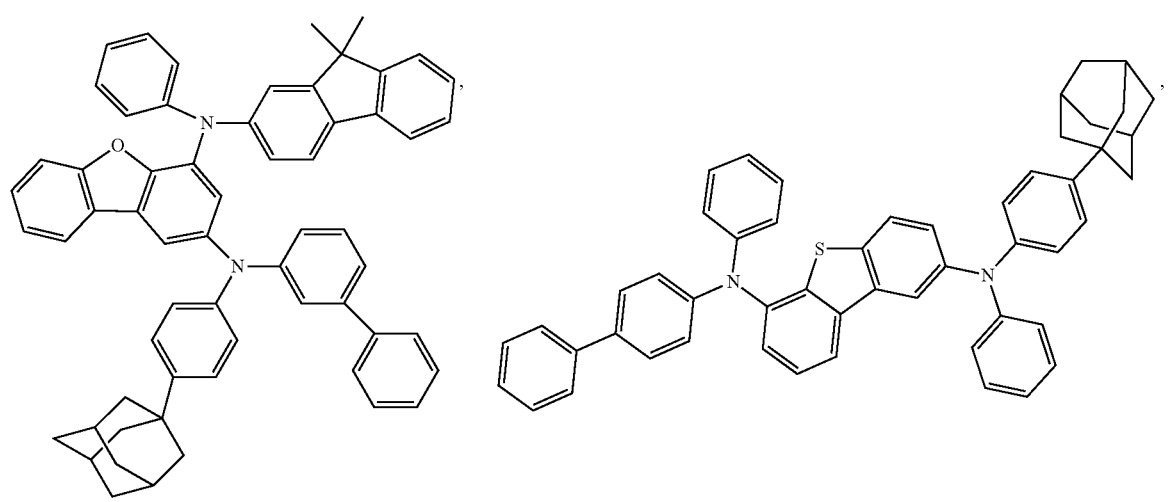

-continued
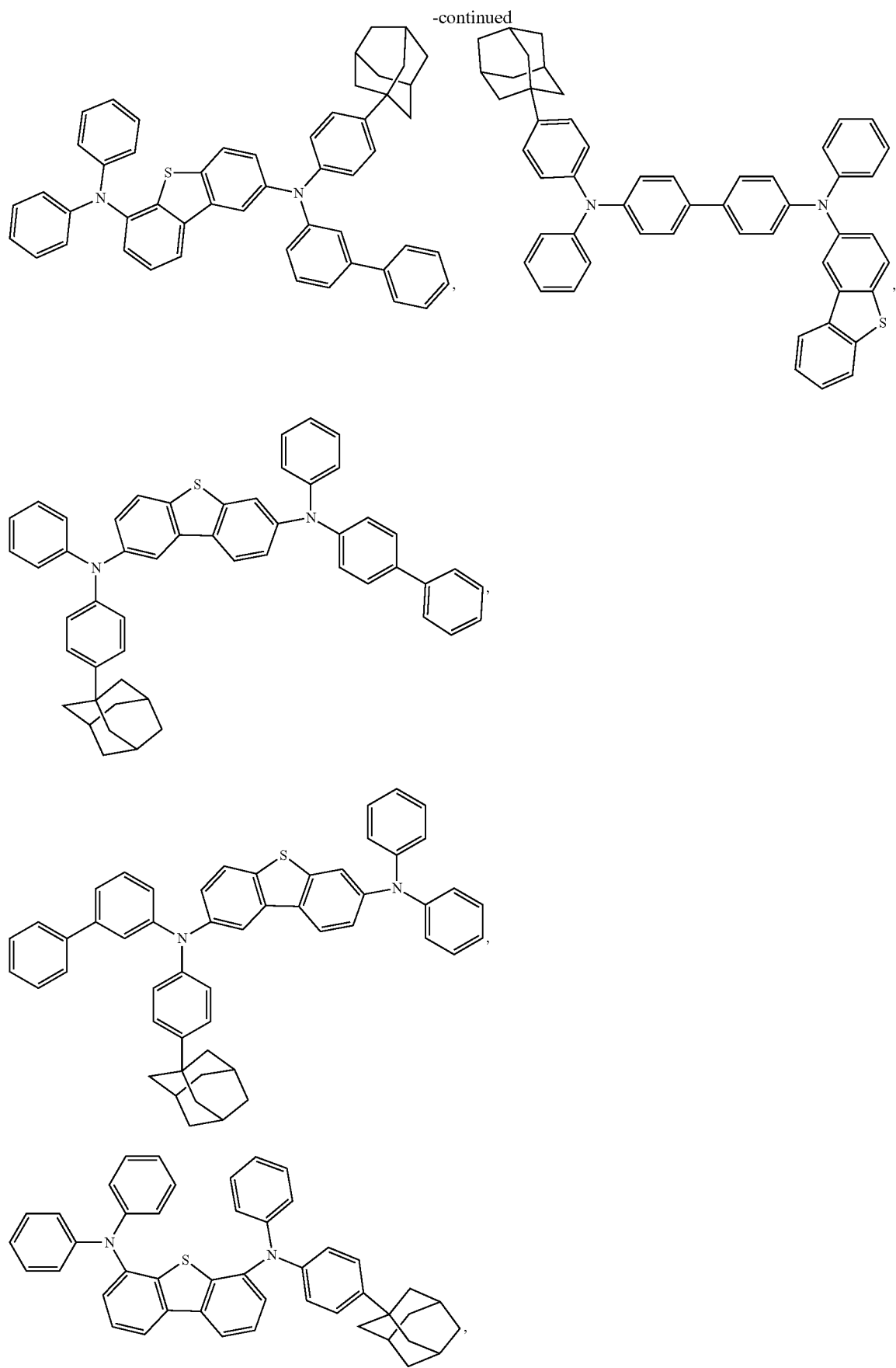

-continued
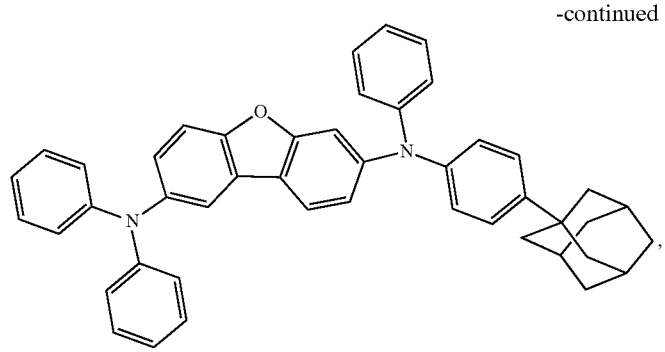
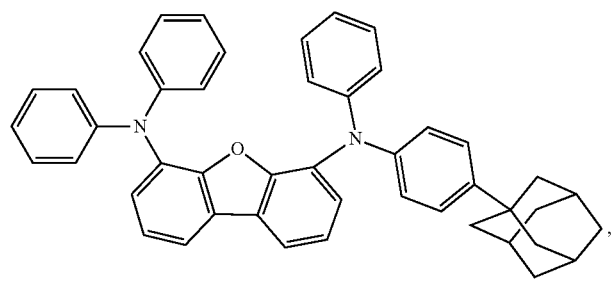
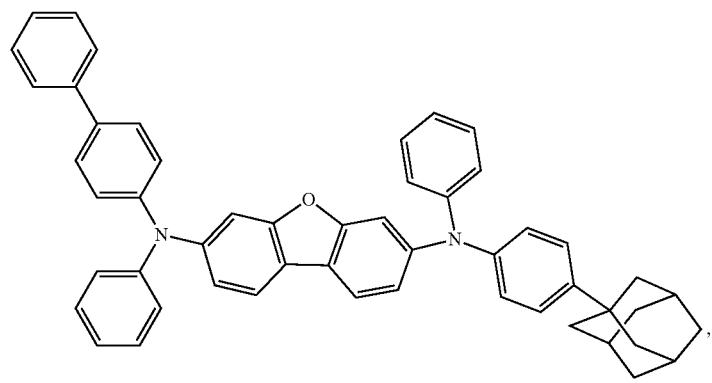
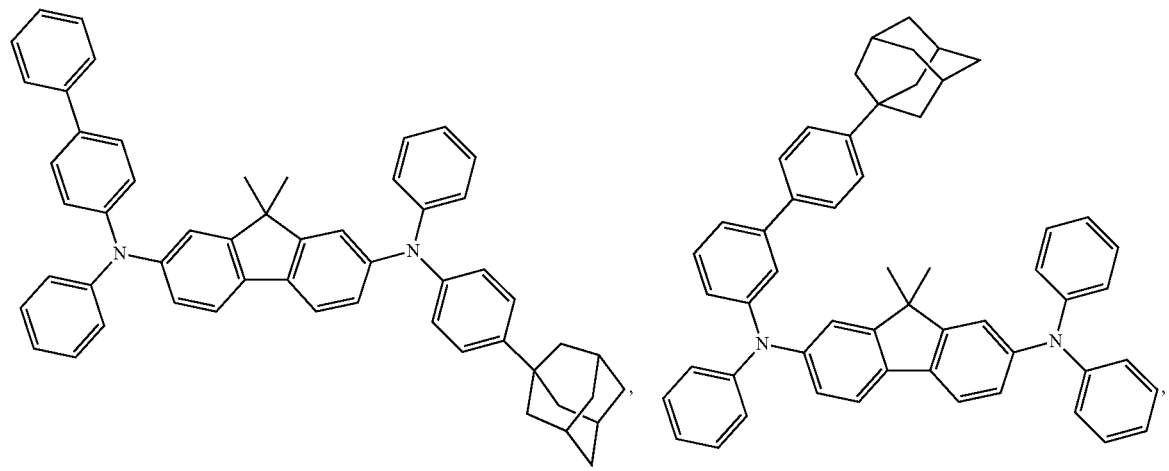

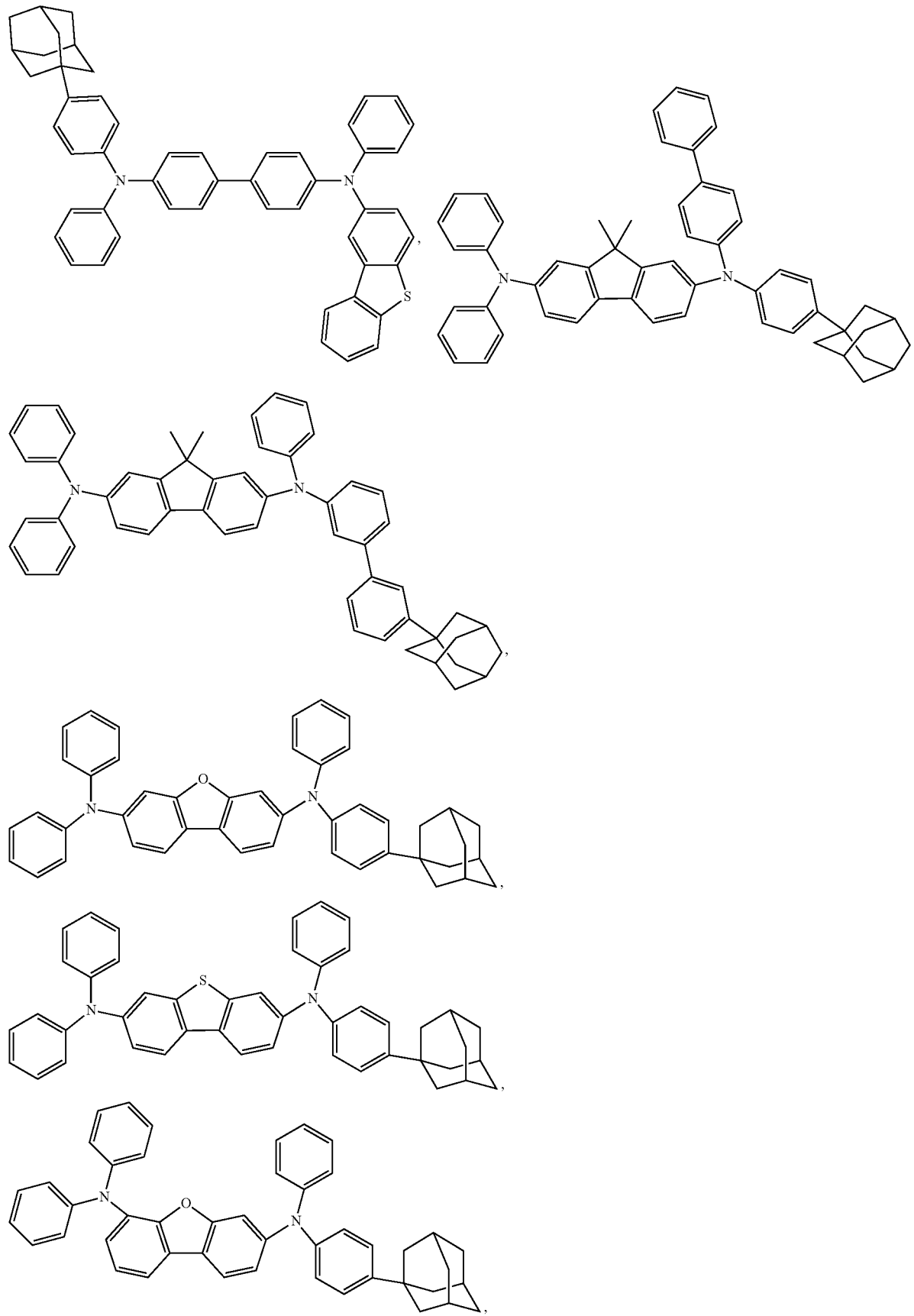

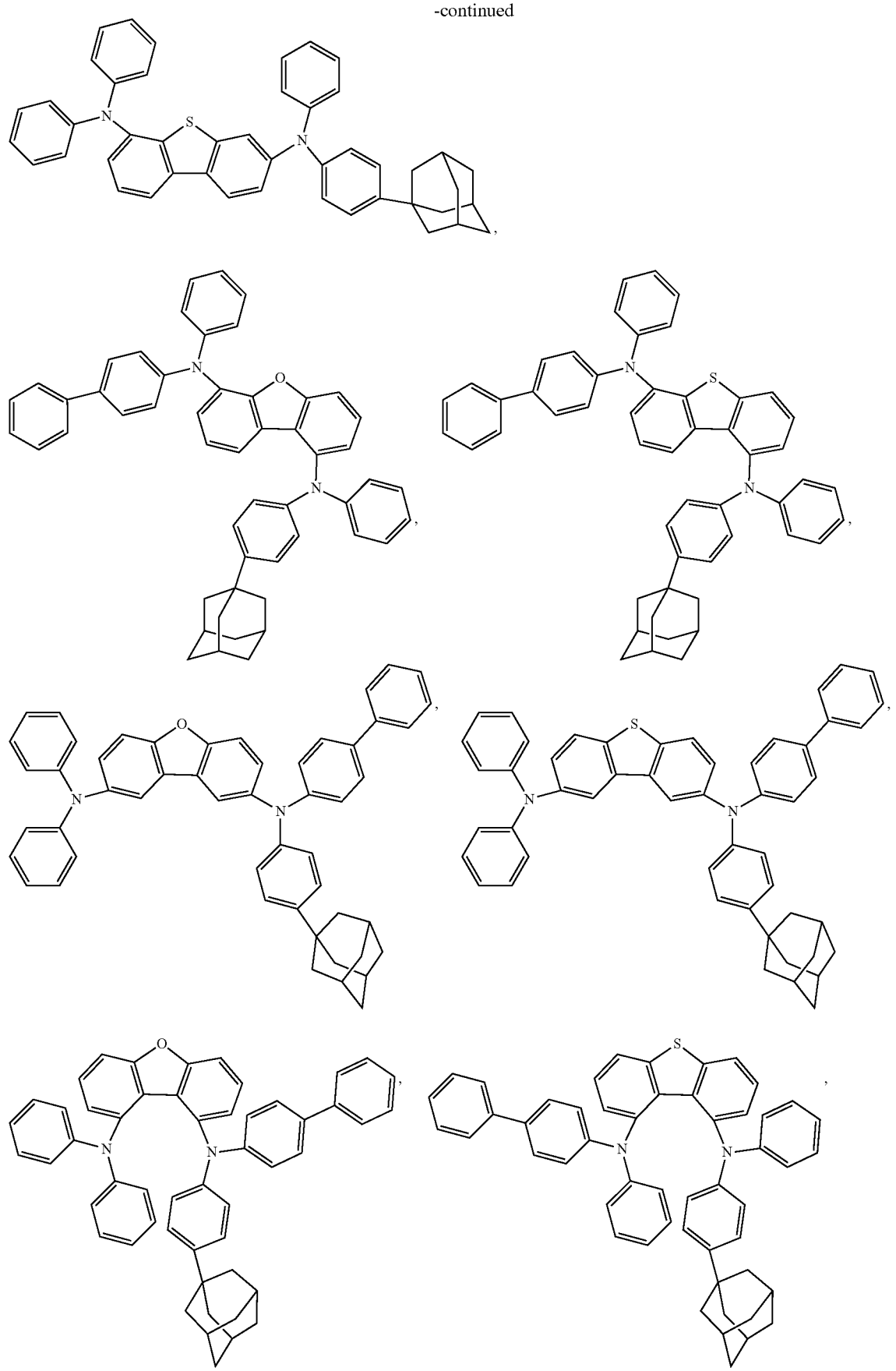

-continued
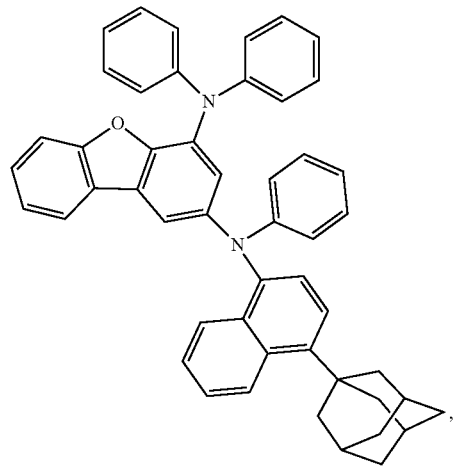
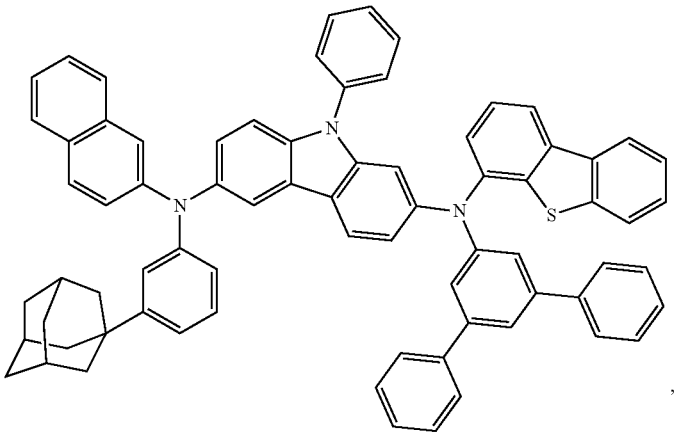
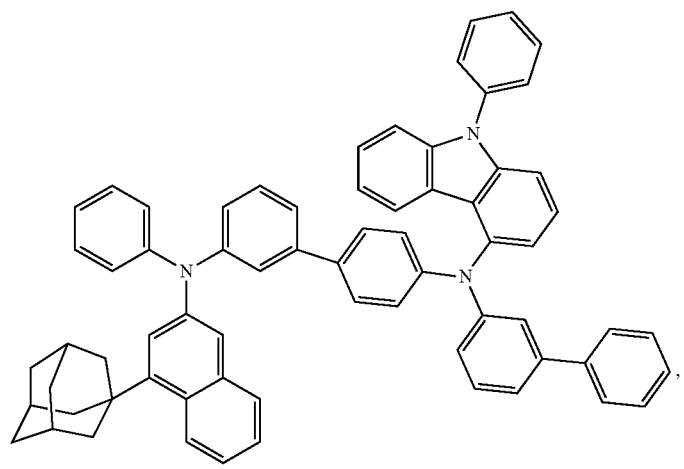
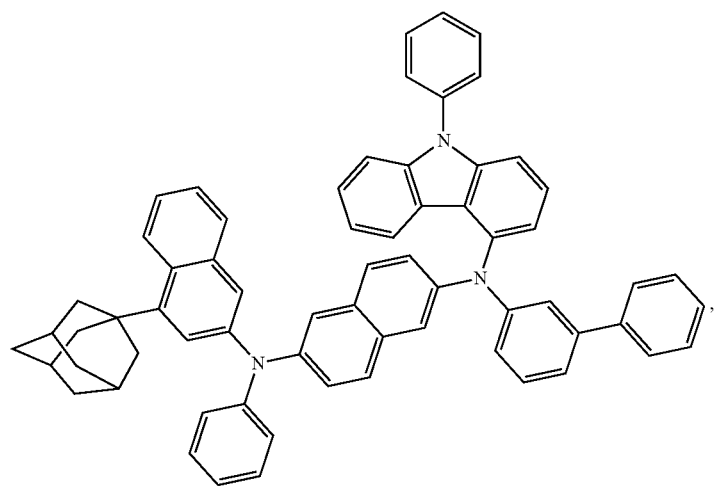

-continued
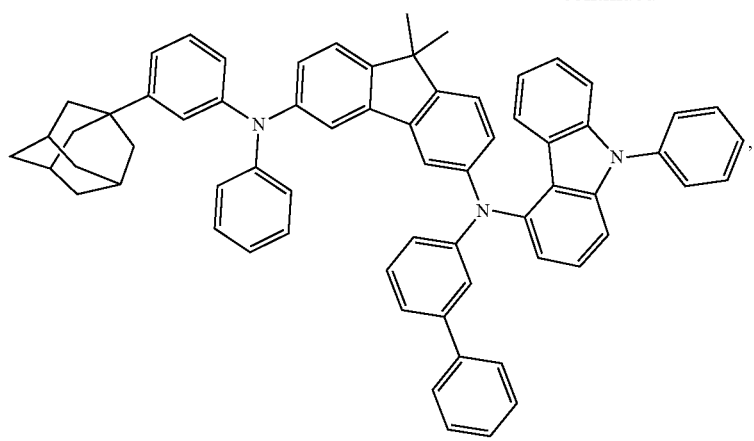

-continued
75
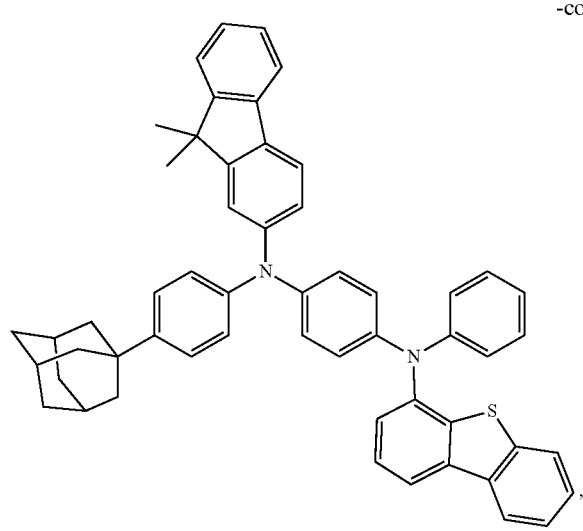
76
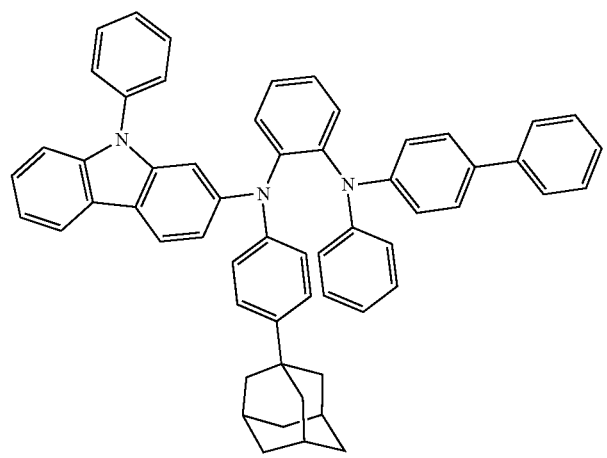
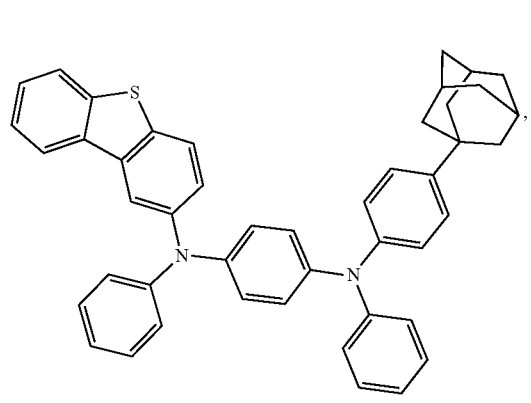
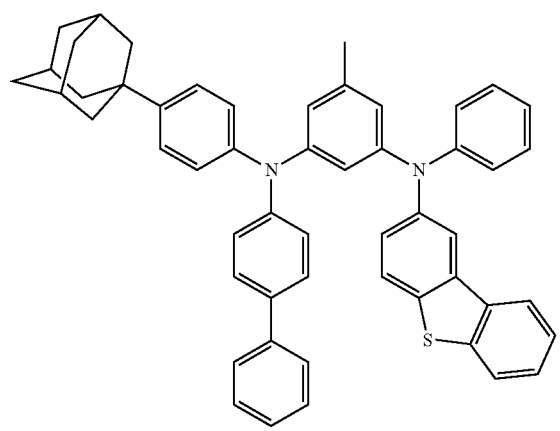
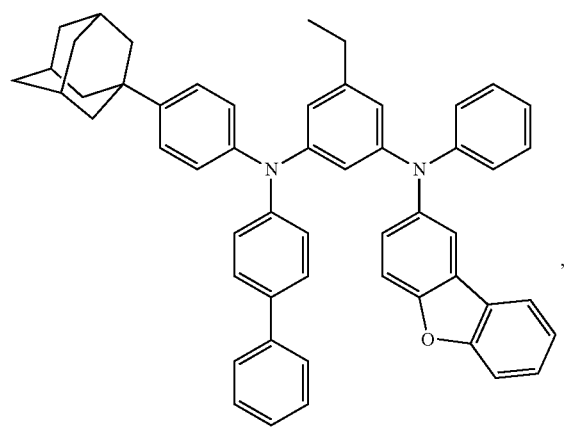
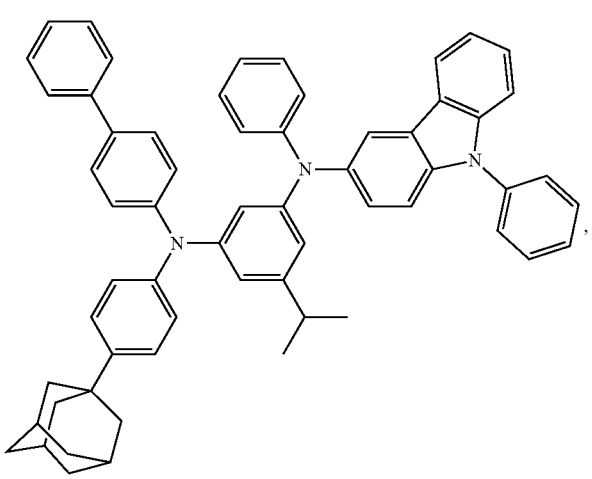

-continued
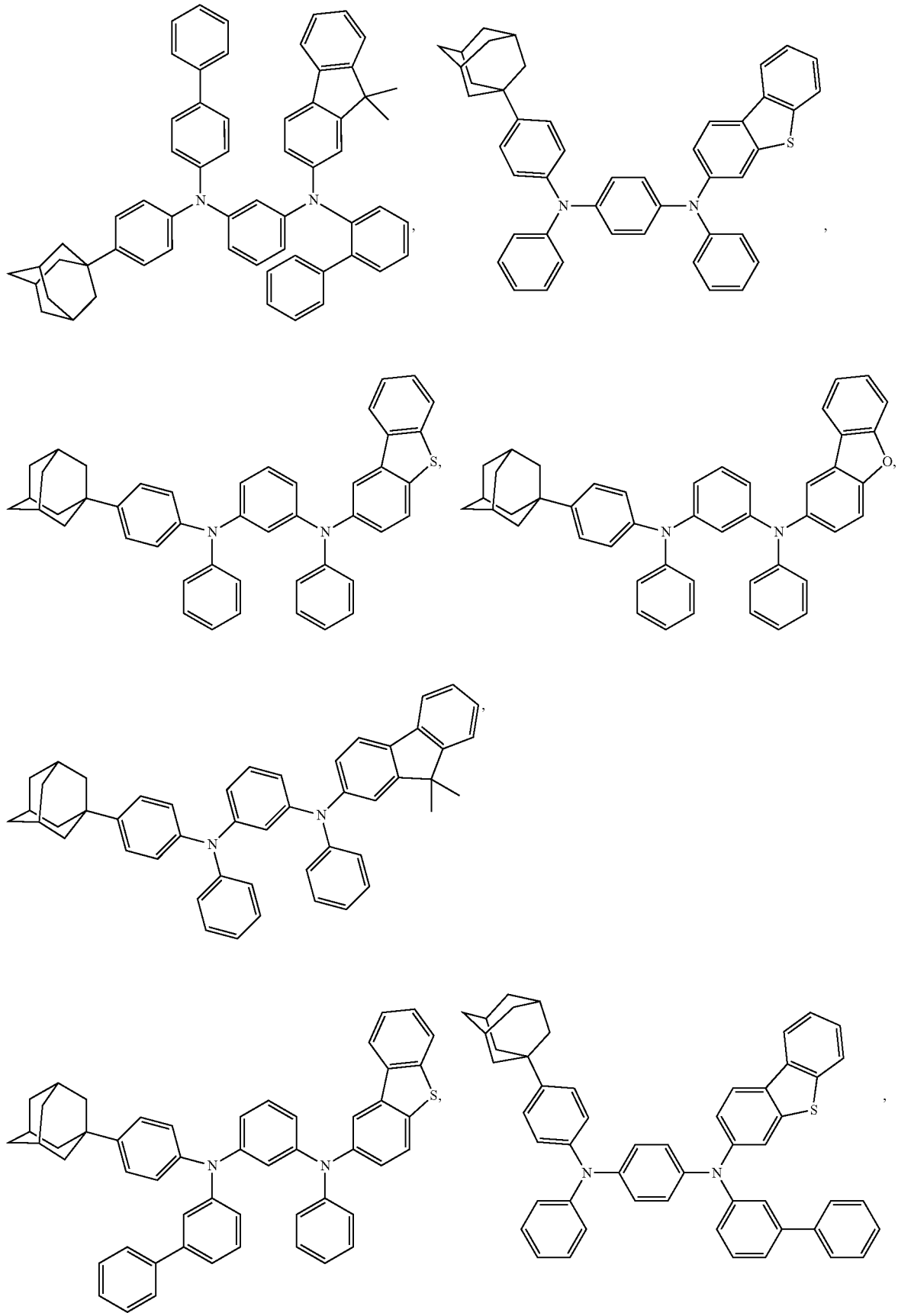

-continued
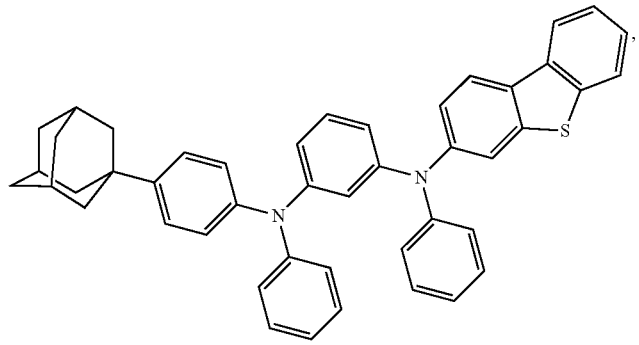
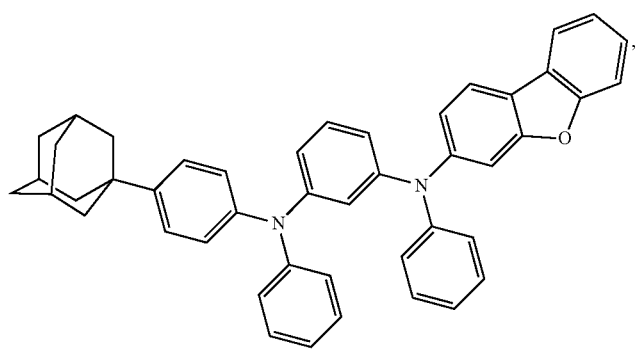
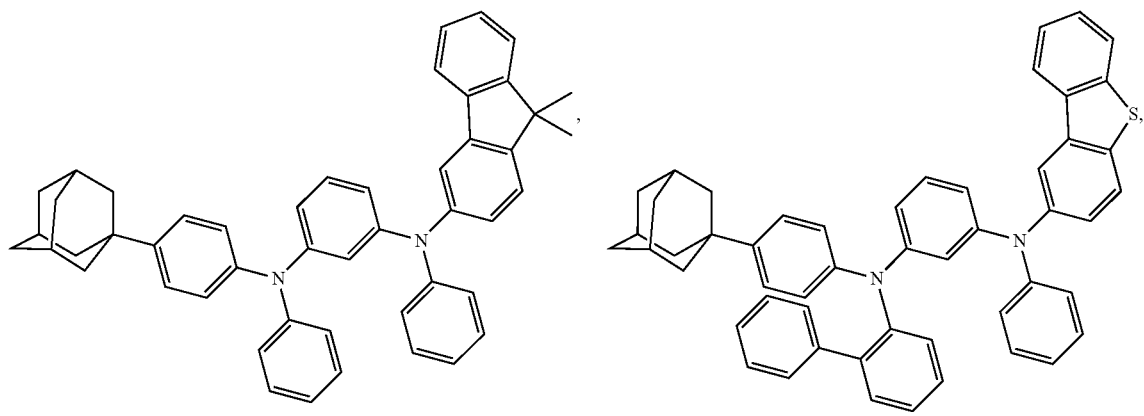
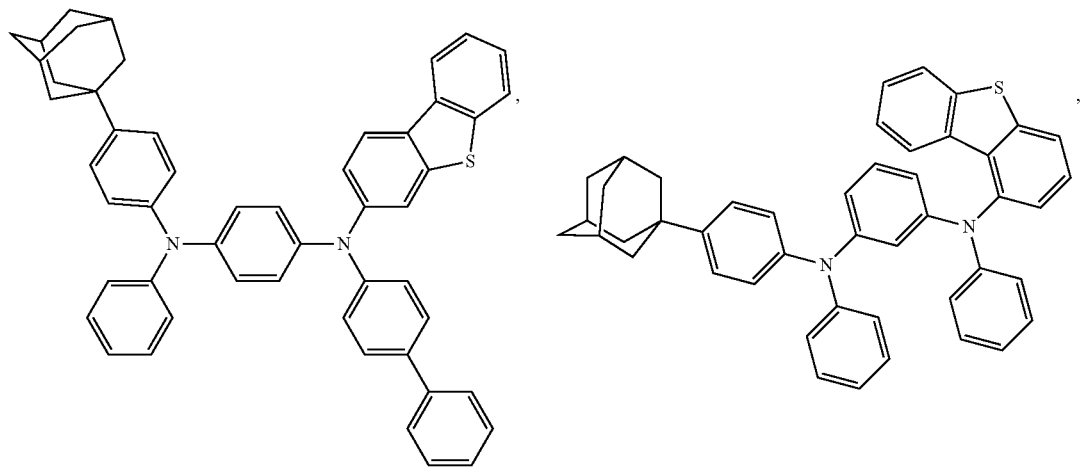

81
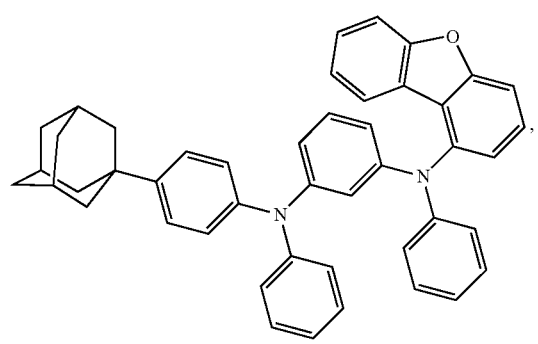
82
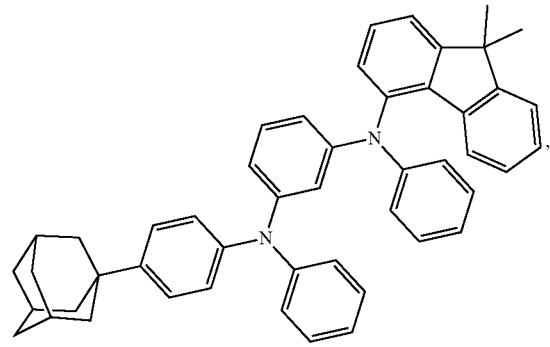
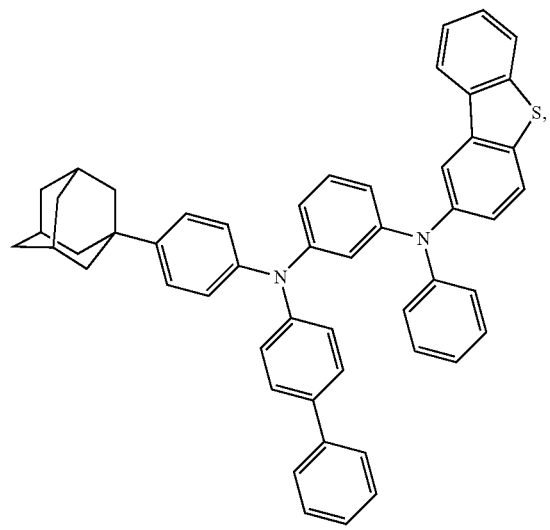
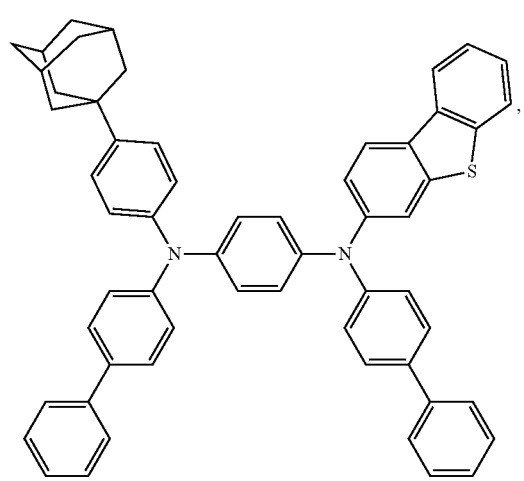
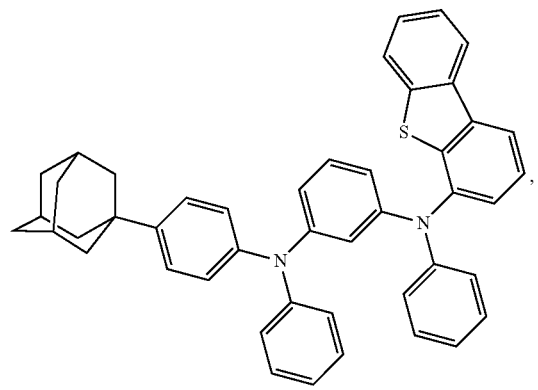
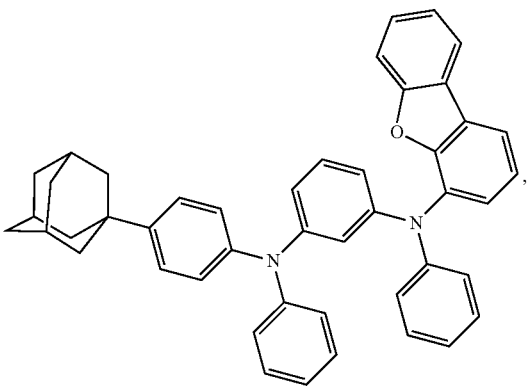

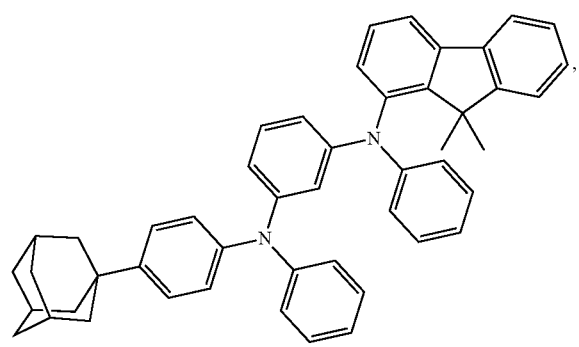
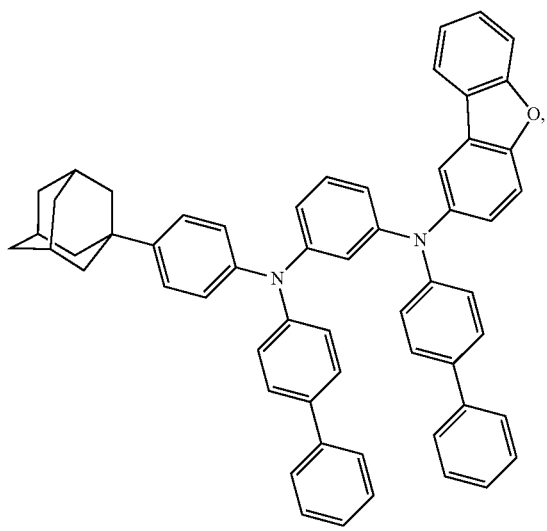
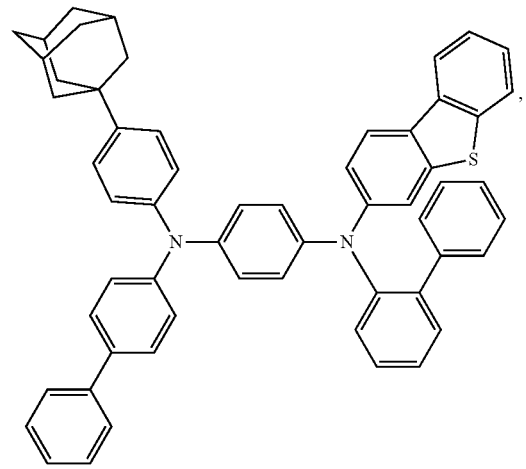
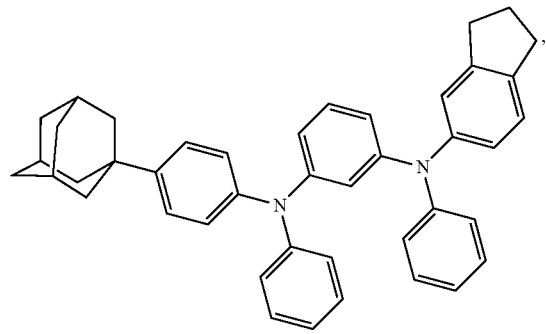
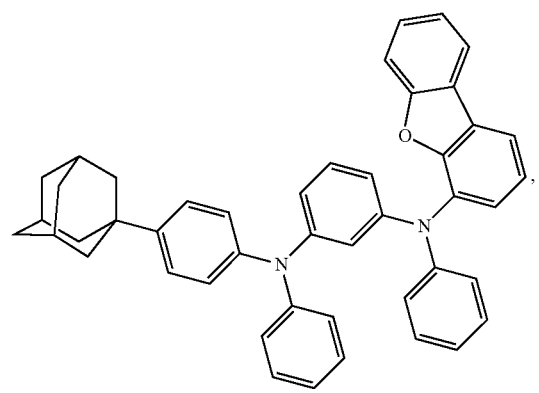
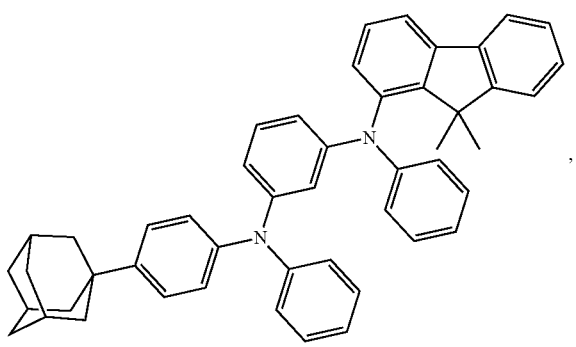

85 86
-continued
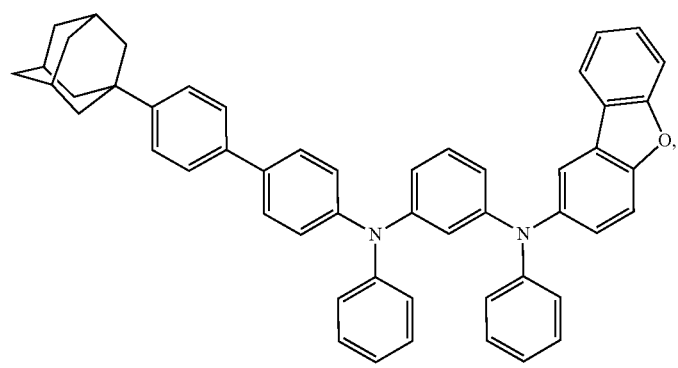
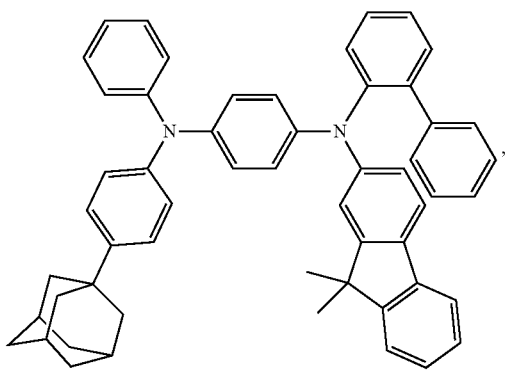
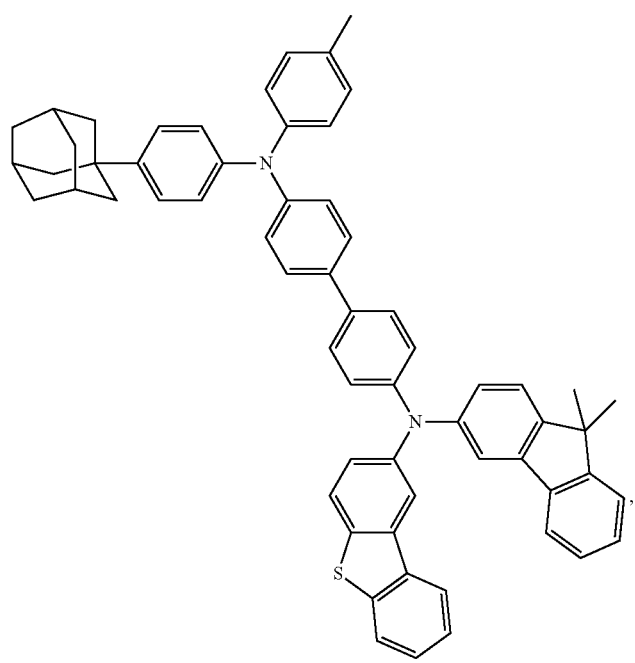
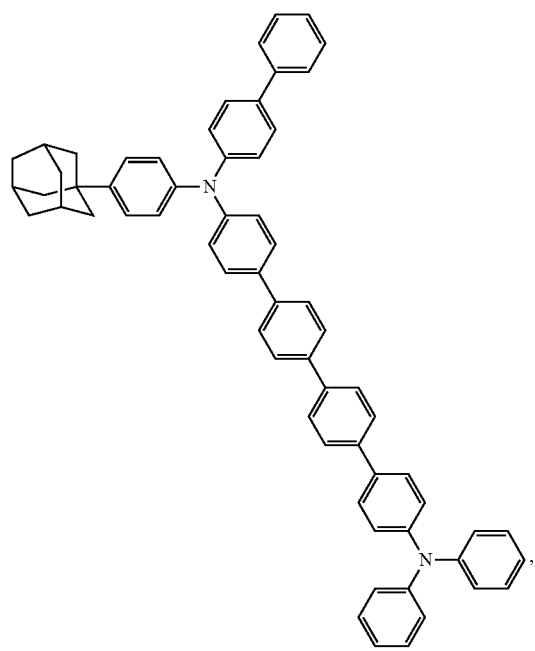

-continued

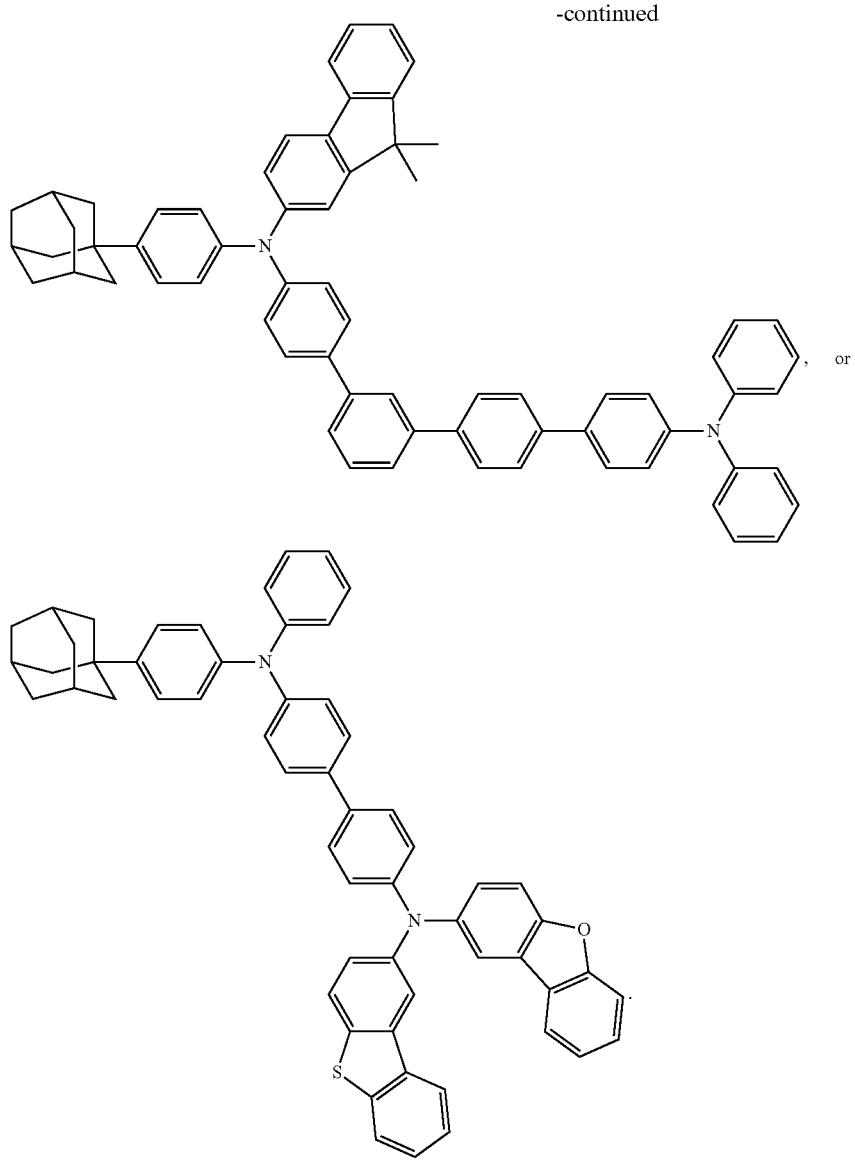

The present disclosure further provides an organic electroluminescent device, including an anode and a cathode that are oppositely arranged, and an organic layer arranged between the anode and the cathode. The organic layer includes a hole injection layer, a hole transport layer, an electron-blocking layer, an emitting layer, a hole blocking layer, an electron transport layer, and an electron injection layer.

In the organic electroluminescent device of the present disclosure, the hole transport layer or the electron-blocking layer includes the above compound to improve the voltage characteristics, efficiency characteristics, and service life characteristics of the organic electroluminescent device.

For example, the organic electroluminescent device may include an anode, a hole transport layer, an electron-blocking layer, an organic emitting layer, a hole blocking layer, an electron transport layer, and a cathode that are sequentially stacked. The compound provided in the present disclosure may be applied to the hole transport layer or the electron-blocking layer of the organic electroluminescent device, to prolong the service life of the organic electroluminescent device, increase the light emitting efficiency of the organic electroluminescent device, or reduce the drive voltage of the organic electroluminescent device.

Optionally, the anode includes an anode material, which is alternatively a material having a large work function and facilitating injection of holes into a functional layer. Specific examples of the anode material include, but are not limited to: a metal, such as nickel, platinum, vanadium, chromium, copper, zinc, and gold, or an alloy thereof; a metal oxide, such as zinc oxide, indium oxide, indium tin oxide (ITO), and indium zinc oxide (IZO); combined metal and oxide, such as ZnO:Al or $SnO_2$:Sb; or a conductive polymer, such as poly(3-methylthiophene), poly[3,4-(ethylene-1,2-dioxy) thiophene] (PEDT), polypyrrole, and polyaniline, and alternatively include a transparent electrode containing indium tin oxide (ITO) as the anode.

Optionally, the hole transport layer may include one or more hole transport materials, and the hole transport materials may be selected from the group consisting of the compound of the present disclosure, a carbazole polymer, a carbazole-linked triarylamine compound, or other types of compounds.

Optionally, the organic emitting layer may include a host material and a guest material. Holes injected into the organic emitting layer and electrons injected into the organic emitting layer may be recombined in the organic emitting layer to form excitons, the excitons transfer energy to the host material, and the host material transfers energy to the guest material, such that the guest material can emit light. In an embodiment of the present disclosure, the host material is CPB or ADN.

The guest material of the organic emitting layer may be a compound with a condensed aryl ring or a derivative thereof, a compound with a heteroaryl ring or a derivative thereof, an aromatic amine derivative or other materials. This is not particularly limited in the present disclosure. In an embodiment of the present disclosure, the guest material of the organic emitting layer may be, e.g., Ir(piq)$_2$(acac). In another embodiment of the present disclosure, the guest material of the organic emitting layer may be, e.g., Ir(qqy)$_3$.

Optionally, the electron transport layer may be a single-layer structure or a multilayer structure, and may include one or more electron transport materials. The electron transporting materials may be selected from, but are not limited to, a benzimidazole derivative, an oxadiazole derivative, a quinoxaline derivative, or other electron transport materials.

Optionally, the cathode may include a cathode material, which is a material having a small work function and facilitating injection of electrons into a functional layer. Specific examples of the cathode material include, but are not limited to, a metal such as magnesium, calcium, sodium, potassium, titanium, indium, yttrium, lithium, gadolinium, aluminum, silver, tin, and lead, or an alloy thereof; or a multilayer material, such as LiF/Al, Liq/Al, LiO$_2$/Al, LiF/Ca, LiF/Al, and BaF$_2$/Ca, and alternatively include an aluminum-containing metal electrode as the cathode. In an embodiment of the present disclosure, the cathode material may be a magnesium-silver alloy.

A hole injection layer may also be arranged between the anode and the hole transport layer to enhance the capacity of injecting holes into the hole transport layer. The hole injection layer may be selected from a benzidine derivative, a starburst arylamine compound, a phthalocyanine derivative, or other materials. This is not particularly limited in the present disclosure. For example, the hole injection layer may be composed of F4-TCNQ.

An electron-blocking layer may also be arranged between the hole transport layer and the organic emitting layer, to block electrons from being transported to the hole transport layer side, increase the recombination rate of electrons and holes in the organic emitting layer, and protect the hole transport layer from being impacted by the electrons. The material of the electron-blocking layer may be the compound of the present disclosure, a carbazole polymer, a carbazole-linked triarylamine compound, or other feasible structures.

An electron injection layer may also be arranged between the cathode and the electron transport layer to enhance the capacity of injecting electrons into the electron transport layer. The electron injection layer may include an inorganic material, such as an alkali metal sulfide and an alkali metal halide, or may include a complex of an alkali metal and an organic substance. For example, the electron injection layer may include LiQ.

SYNTHESIS EXAMPLES

The present disclosure will be further described in detail below in conjunction with the examples. However, the following examples are merely illustrations of the present disclosure, and do not impose limitations on the present disclosure.

In the synthesis examples described below, unless otherwise stated, the unit of all temperature is degree Celsius. Some reagents are purchased from commercial suppliers, such as Aldrich Chemical Company, Arco Chemical Company, and Alfa Chemical Company, and are used without any further purification, unless otherwise stated.

In each synthesis example, testing conditions of low-resolution mass spectrum (MS) data include: Agilent 6120 quadrupole HPLC-M (column model: Zorbax SB-C18, 2.1× 30 mm, 3.5 μm, 6 min, and flow rate: 0.6 mL/min. Mobile phase: 5%-95% (a proportion of (acetonitrile containing 0.1% formic acid) in (water containing 0.1% formic acid)), using electrospray ionization (ESI), and using UV detection at 210 nm/254 nm.

HNMR: Bruker 600 MHz NMR spectrometer at room temperature, with CD$_2$Cl$_2$ as a solvent (ppm), and with TMS (0 ppm) as a reference standard. When a multiplet appears, the following abbreviations will be used: s (singlet), d (doublet), t (triplet), or m (multiplet).

Synthesis Example 1

Synthesis of Compound 1

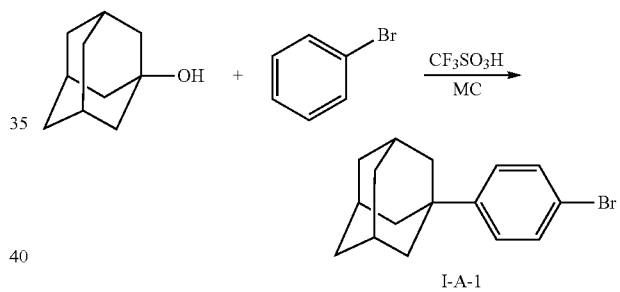

I-A-1

Adamantanol (50.0 g, 328.4 mmol), bromobenzene (51.6 g, 328.4 mmol), and dichloromethane (500 mL) were added into a round bottom flask, and cooled to −5 to 0° C. under the protection of nitrogen. Trifluoromethanesulfonic acid (73.9 g, 492.6 mmol) was added dropwise, and the mixture was stirred at the temperature for 3 h. The reaction mixture was washed with deionized water (300 mL) to pH=7, and extracted with dichloromethane (100 mL). The combined organic phase was dried over anhydrous magnesium sulfate, and filtered. The solvent was removed under reduced pressure; and the obtained crude product was purified by silica gel column chromatography using n-heptane as the mobile phase, to obtain intermediate I-A-1 as a white solid (53.1 g, 55.4%).

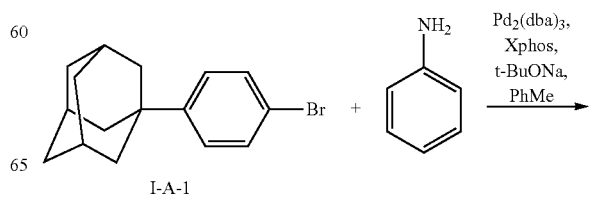

I-A-1

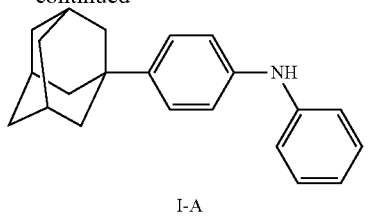

I-A

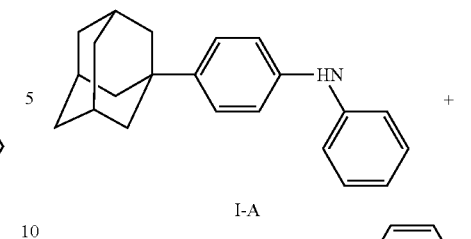

I-A      +

The intermediate I-A-1 (7.0 g, 24.04 mmol), phenylamine (2.69 g, 28.84 mmol), tris(dibenzylideneacetone)dipalladium (0.22 g, 0.24 mmol), 2-(dicyclohexylphosphino)-2',4',6'-triisopropylbiphenyl (0.23 g, 0.48 mmol), and sodium tert-butoxide (3.46 g, 36.05 mmol) were added to methylbenzene (60 mL). The mixture was heated to 108° C. under the protection of nitrogen, stirred for 3 h, and then cooled to room temperature. The reaction mixture was washed with deionized water, dried over anhydrous magnesium sulfate, and filtered. Then, the filtrate passed through a short silica gel column, and the solvent was removed under reduced pressure. The crude product was purified by recrystallization using a mixture of dichloromethane and n-heptane, to obtain intermediate I-A as a light green solid (5.83 g, 79.9%).

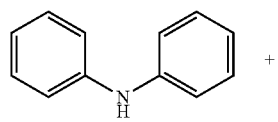   +

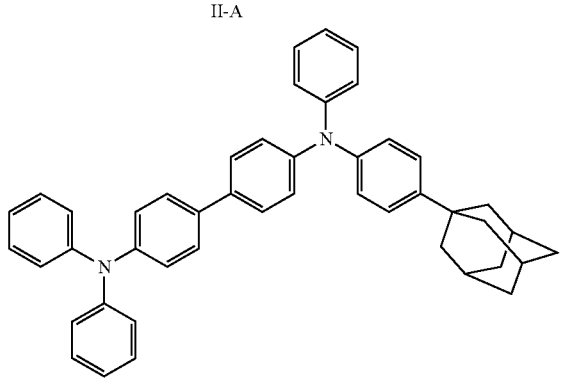

II-A

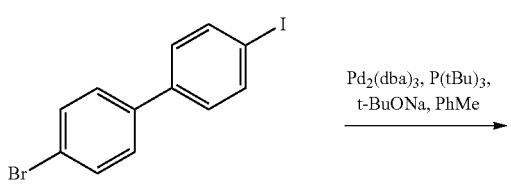

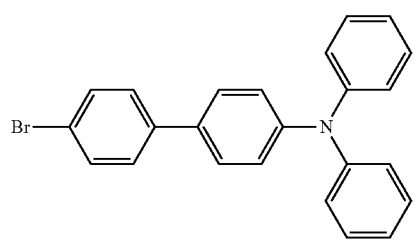

II-A

Diphenylamine (3.80 g, 22.45 mmol), 4-bromo-4'-iodobiphenyl (10.48 g, 29.19 mmol), tris(dibenzylideneacetone)dipalladium (0.21 g, 0.22 mmol), tri-tert-butylphosphine (0.10 g, 0.44 mmol), and sodium tert-butoxide (3.24 g, 33.68 mmol) were added to methylbenzene (100 mL). The mixture was heated to 108° C. under the protection of nitrogen, stirred for 10 h, and then cooled to room temperature. The reaction mixture was washed with water, dried over magnesium sulfate, and then filtered. Then, the solvent was removed from the filtrate under reduced pressure; and the residue was purified by silica gel column chromatography and eluted with n-heptane to obtain intermediate II-A as a white solid (3.6 g, 40.06%).

Compound 1

The intermediate I-A (3 g, 9.89 mmol), the intermediate II-A (3.55 g, 9.89 mmol), tris(dibenzylideneacetone)dipalladium (0.09 g, 0.10 mmol), 2-(dicyclohexylphosphino)-2',6'-dimethoxylbiphenyl (0.08 g, 0.20 mmol), and sodium tert-butoxide (1.43 g, 14.83 mmol) were added to methylbenzene (30 mL). The mixture was heated to 108° C. under the protection of nitrogen, stirred for 1 h, and then cooled to room temperature. After the reaction mixture was filtered, the solvent was removed from the filtrate under reduced pressure. The residue was purified by silica gel column chromatography and eluted with a mixture of dichloromethane and n-heptane (1:1) to obtain the crude product. Then, the crude product was purified by recrystallization using a mixture of dichloromethane and ethyl acetate, to obtain compound 1 as a white solid (5.15 g, 83.74%). MS: m/z=623.3 (M+H)$^+$ Synthesis Example 2

Synthesis of Compound 2

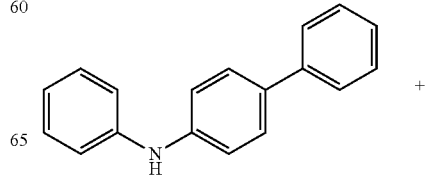   +

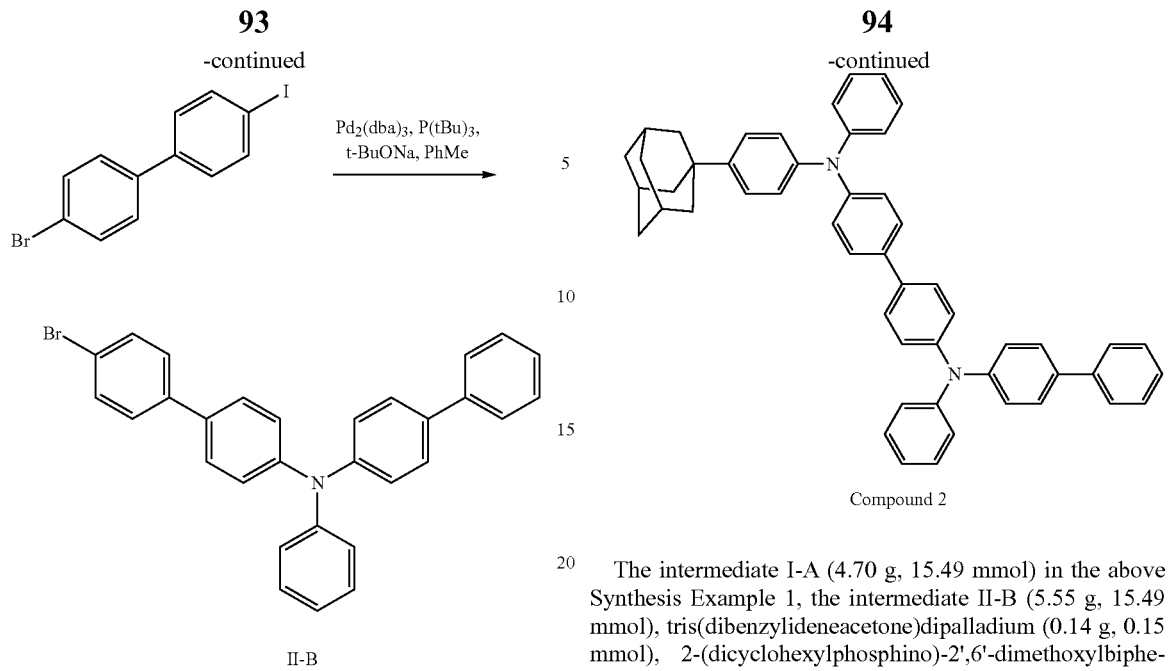

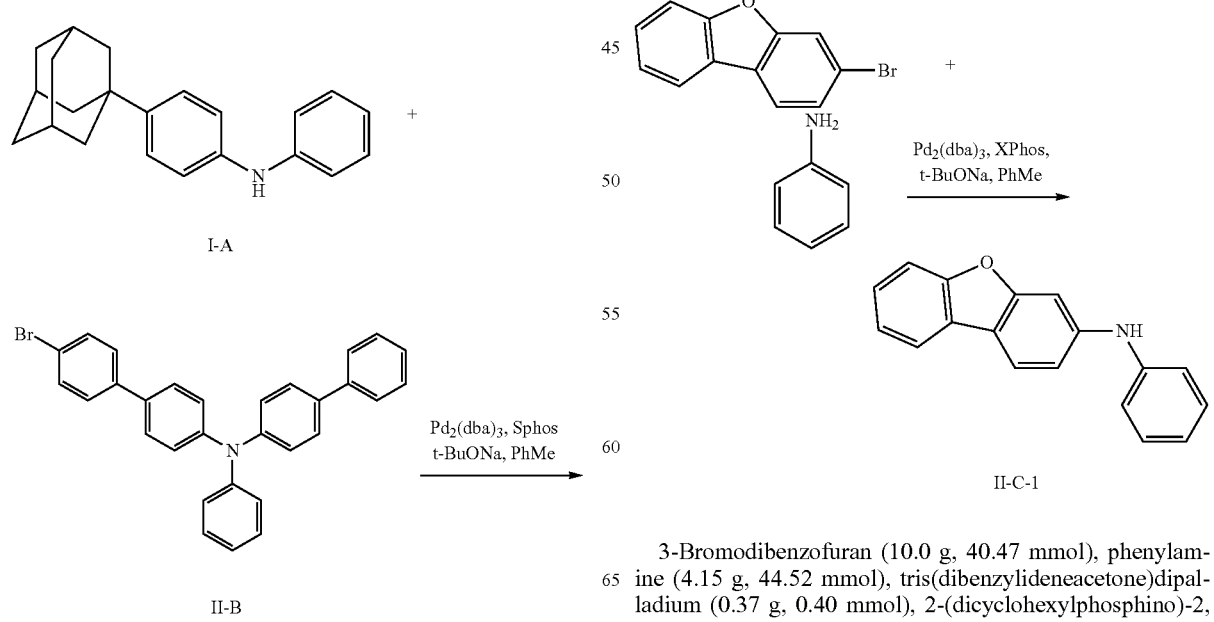

N-phenyl-4-biphenylamine (5.00 g, 20.38 mmol), 4-bromo-4'-iodobiphenyl (9.15 g, 25.48 mmol), tris(dibenzylideneacetone)dipalladium (0.19 g, 0.20 mmol), tri-tert-butylphosphine (0.08 g, 0.41 mmol), and sodium tert-butoxide (2.94 g, 30.57 mmol) were added to methylbenzene (80 mL). The mixture was heated to 108° C. under the protection of nitrogen, stirred for 16 h, and then cooled to room temperature. The reaction mixture was washed with water, dried over magnesium sulfate, and then filtered. Then, the solvent was removed from the filtrate under reduced pressure. The residue was purified by silica gel column chromatography and eluted with n-heptane to obtain an intermediate II-B (5.55 g, 57.16%).

The intermediate I-A (4.70 g, 15.49 mmol) in the above Synthesis Example 1, the intermediate II-B (5.55 g, 15.49 mmol), tris(dibenzylideneacetone)dipalladium (0.14 g, 0.15 mmol), 2-(dicyclohexylphosphino)-2',6'-dimethoxybiphenyl (0.13 g, 0.31 mmol), and sodium tert-butoxide (2.23 g, 23.23 mmol) were added to methylbenzene (50 mL). The mixture was heated to 108° C. under the protection of nitrogen, stirred for 1 h, and then cooled to room temperature. After the reaction mixture was filtered, the solvent was removed from the filtrate under reduced pressure. The residue was purified by silica gel column chromatography and eluted with a mixture of dichloromethane and n-heptane (1:1) to obtain the crude product. Then, the crude product was purified by recrystallization using a mixture of dichloromethane and ethyl acetate, to obtain compound 2 as a white solid (7.34 g, 67.78%). MS: m/z=699.4 (M+H)⁺

Synthesis Example 3

3-Bromodibenzofuran (10.0 g, 40.47 mmol), phenylamine (4.15 g, 44.52 mmol), tris(dibenzylideneacetone)dipalladium (0.37 g, 0.40 mmol), 2-(dicyclohexylphosphino)-2,4,6-triisopropylbiphenyl (0.39 g, 0.81 mmol), and sodium tert-butoxide (5.84 g, 60.71 mmol) were added to methylbenzene (100 mL). The mixture was heated to 108° C. under the nitrogen atmosphere, stirred for 1 h, and then cooled to room temperature. The reaction mixture was washed with water, dried over magnesium sulfate, and filtered. Then, the filtrate passed through a short silica gel column, and the solvent was removed from the eluent under reduced pressure. The crude product was purified by recrystallization using a mixture of dichloromethane and n-heptane, to obtain intermediate II-C-1 as a gray solid (8.2 g, 78.17%).

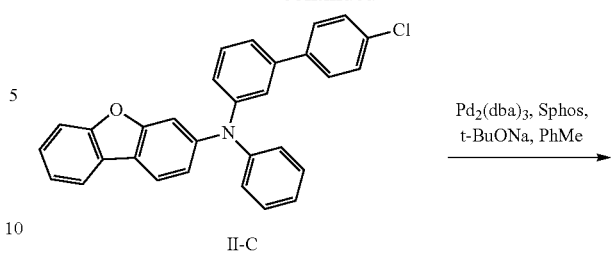

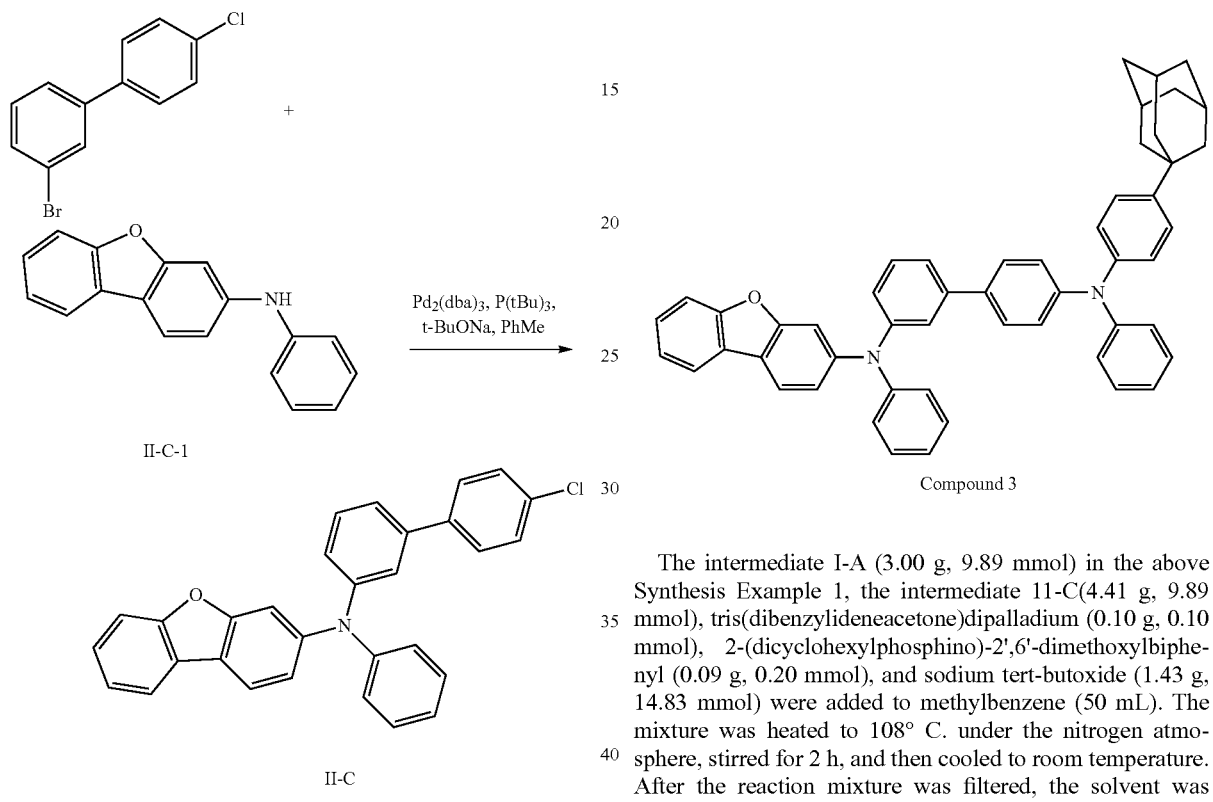

3-Bromo-4'-chloro-1,1'-biphenyl (8.00 g, 29.90 mmol), the intermediate II-C-1 (5.17 g, 19.93 mmol), tris(dibenzylideneacetone)dipalladium (0.18 g, 0.20 mmol), tri-tert-butylphosphine (0.10 g, 0.40 mmol), and sodium tert-butoxide (2.87 g, 29.90 mmol) were added to methylbenzene (70 mL). The mixture was heated to 108° C. under the nitrogen atmosphere, stirred for 12 h, and then cooled to room temperature. The reaction mixture was washed with water, dried over magnesium sulfate, and then filtered. Then, the solvent was removed from the filtrate under reduced pressure. The residue was purified by silica gel column chromatography and eluted with n-heptane to obtain intermediate II-C as a gray solid (4.82 g, 54.28%).

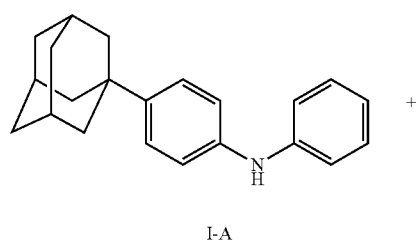

The intermediate I-A (3.00 g, 9.89 mmol) in the above Synthesis Example 1, the intermediate 11-C(4.41 g, 9.89 mmol), tris(dibenzylideneacetone)dipalladium (0.10 g, 0.10 mmol), 2-(dicyclohexylphosphino)-2',6'-dimethoxybiphenyl (0.09 g, 0.20 mmol), and sodium tert-butoxide (1.43 g, 14.83 mmol) were added to methylbenzene (50 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of dichloromethane and n-heptane (1:3) to obtain the crude product. Then, the crude product was purified by recrystallization using a mixture of dichloromethane and ethyl acetate, to obtain compound 3 as a white solid (5.35 g, 76.14%). MS: m/z=713.3 (M+H)$^+$ Synthesis Example 4

Synthesis of Compound 4

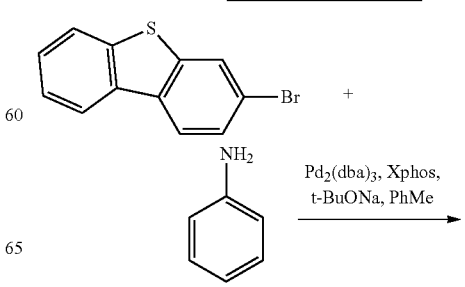

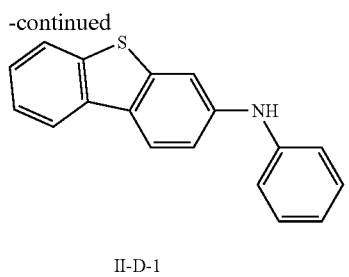

II-D-1

Phenylamine (10.0 g, 107.38 mmol), 3-bromodibenzothiophene (26.91 g, 102.26 mmol), tris(dibenzylideneacetone)dipalladium (0.94 g, 1.02 mmol), 2-(dicyclohexylphosphino)-2,4,6-triisopropylbiphenyl (0.98 g, 2.05 mmol), and sodium tert-butoxide (14.74 g, 153.40 mmol) were added to methylbenzene (180 mL). The mixture was heated to 108° C. under the nitrogen atmosphere, stirred for 2 h, and then cooled to room temperature. The reaction mixture was washed with water, dried over magnesium sulfate, and filtered. Then, the filtrate passed through a short silica gel column, and the solvent was removed from the eluent under reduced pressure. The crude product was purified by recrystallization using a mixture of dichloromethane and n-heptane, to obtain a white solid intermediate II-D-1 (21.69 g, 77.02%).

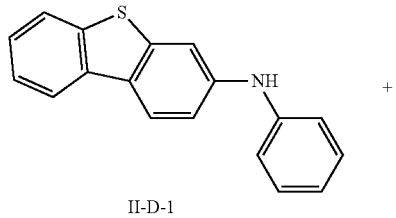

II-D-1

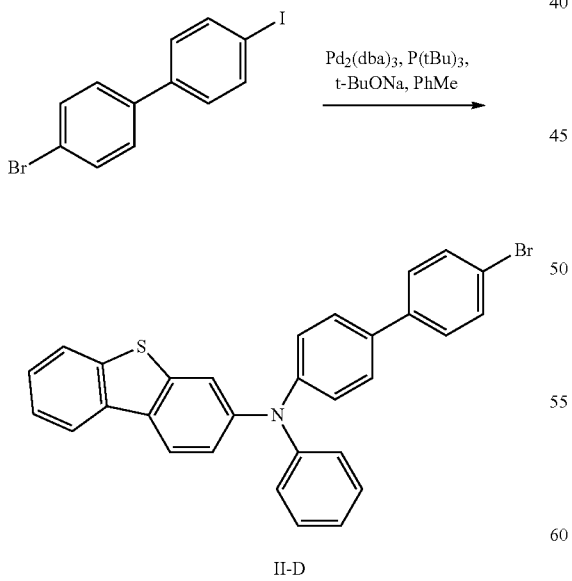

II-D

The intermediate II-D-1 (5.90 g, 21.43 mmol), 4-bromo-4'-iodobiphenyl (10 g, 27.85 mmol), tris(dibenzylideneacetone)dipalladium (0.19 g, 0.21 mmol), tri-tert-butylphosphine (0.20 g, 0.13 mmol), and sodium tert-butoxide (3.09 g, 32.14 mmol) were added to methylbenzene (80 mL). The mixture was heated to 108° C. under the nitrogen atmosphere atmosphere, stirred for 7 h, and then cooled to room temperature. After the reaction mixture was filtered, the solvent was removed from the filtrate under reduced pressure. The residue was purified by silica gel column chromatography and eluted with n-heptane to obtain the crude product. Then, the crude product was purified by recrystallization using a mixture of dichloromethane and n-heptane, to obtain intermediate II-D as a white solid (6.07 g, 55.95%).

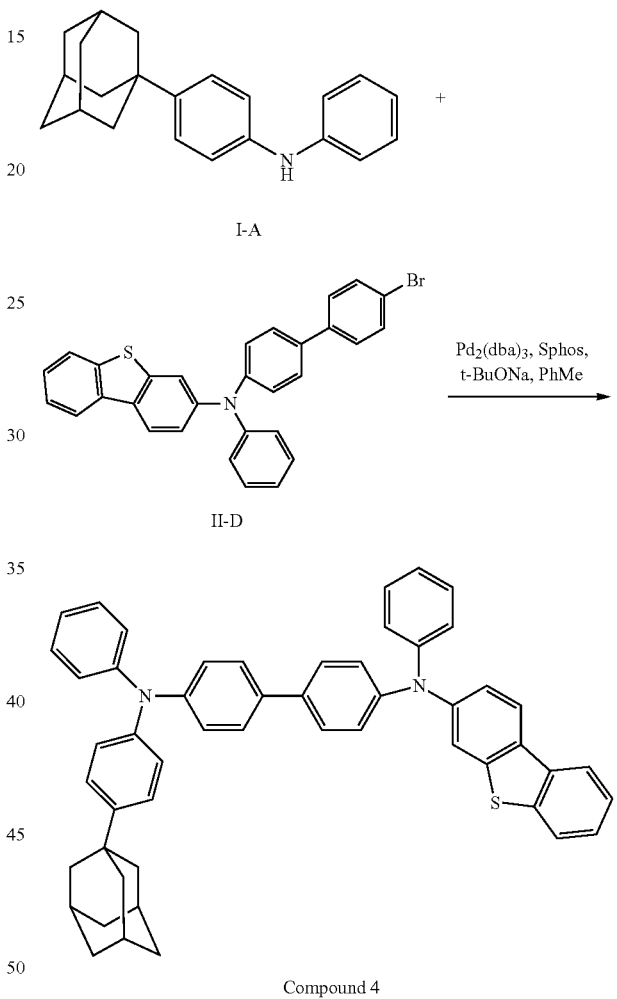

Compound 4

The intermediate I-A (3.60 g, 11.86 mmol) in the above Synthesis Example 1, the intermediate II-D (6.07 g, 11.86 mmol), tris(dibenzylideneacetone)dipalladium (0.11 g, 0.12 mmol), 2-(dicyclohexylphosphino)-2',6'-dimethoxylbiphenyl (0.11 g, 0.24 mmol), and sodium tert-butoxide (1.71 g, 17.80 mmol) were added to methylbenzene (50 mL). The mixture was heated to 108° C. under the nitrogen atmosphere, stirred for 1 h, and then cooled to room temperature. After the reaction mixture was filtered, the solvent was removed from the filtrate under reduced pressure; and the crude product was purified by recrystallization using a mixture of dichloromethane and n-heptane, to obtain compound 4 as a white solid (7.12 g, 56.62%). MS: m/z=729.3 (M+H)$^+$

Synthesis Example 5

Synthesis of Compound 5

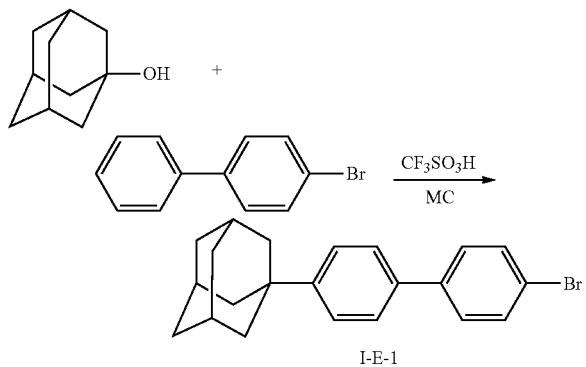

Adamantanol (10.0 g, 65.69 mmol) and 4-bromobiphenyl (15.31 g, 65.69 mmol) were added to 150 mL of dichloromethane present in a round bottom flask. The mixture was cooled to −20 to −10° C. under the nitrogen atmosphere, trifluoromethanesulfonic acid (14.7 g, 98.53 mmol) was added dropwise, and the mixture was stirred at the temperature for 6 h. The reaction mixture was washed with deionized water (100 mL) to pH=7, and extracted with dichloromethane (100 mL). The organic phases were combined, dried over anhydrous magnesium sulfate, and filtered. The solvent was removed under reduced pressure; and the obtained crude product was purified by silica gel column chromatography using n-heptane as the mobile phase, to obtain intermediate I-E-1 as a white solid (9.80 g, 40.61%).

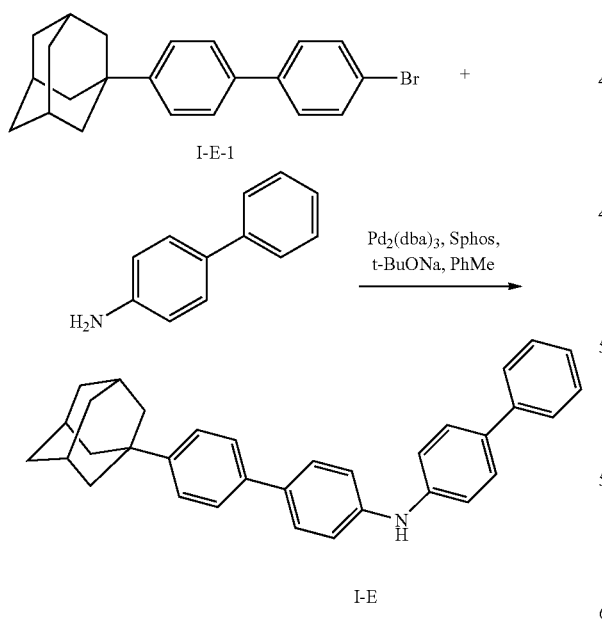

The intermediate I-E-1 (9.50 g, 25.89 mmol), 4-aminobiphenyl (4.60 g, 27.18 mmol), tris(dibenzylideneacetone)dipalladium (0.24 g, 0.26 mmol), 2-(dicyclohexylphosphino)-2',4',6'-triisopropylbiphenyl (0.25 g, 0.52 mmol), and sodium tert-butoxide (3.73 g, 38.83 mmol) were added to methylbenzene (100 mL). The mixture was heated to 108° C. under the nitrogen atmosphere, stirred for 3 h, and then cooled to room temperature. The reaction mixture was washed with deionized water, dried over anhydrous magnesium sulfate, and filtered. Then, the filtrate passed through a short silica gel column, and the solvent was removed under reduced pressure. The crude product was purified by recrystallization using a mixture of dichloromethane and n-heptane, to obtain intermediate I-E as a light green solid (8.71 g, 73.88%).

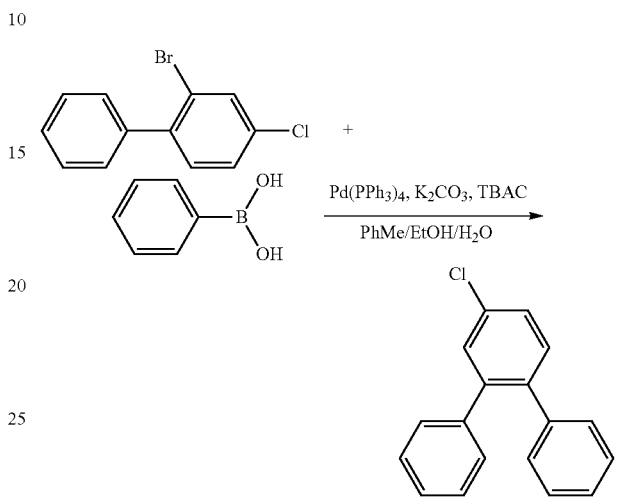

2-bromo-4-chlorobiphenyl (50.00 g, 180.69 mmol), phenylboronic acid (20.17 g, 170.79 mmol), tetrakis(triphenylphosphine)palladium (4.1 g, 0.36 mmol), potassium carbonate (54.0 g, 390.16 mmol), tetrabutylammonium chloride (9.9 g, 35.6 mmol), methylbenzene (400 mL), ethanol (100 mL), and deionized water (100 mL) were added to a round bottom flask. The mixture was heated to 78° C. under the nitrogen atmosphere, and stirred for 8 h. The reaction mixture was cooled to room temperature, and extracted with methylbenzene (1000 mL). The organic phases were combined, dried over anhydrous magnesium sulfate, and filtered. The solvent was removed under reduced pressure. The obtained crude product was purified by silica gel column chromatography using dichloromethane/n-heptane (1:8) as the mobile phase, and then purified by recrystallization with a mixture of dichloromethane and ethanol, to obtain intermediate II-E-1 as a light yellow solid (38.0 g, 80.85%).

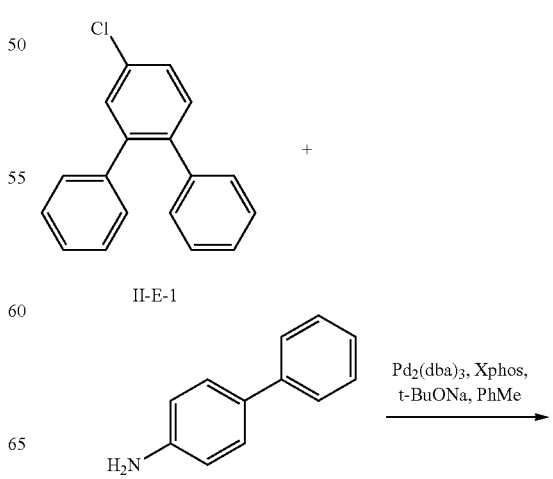

-continued

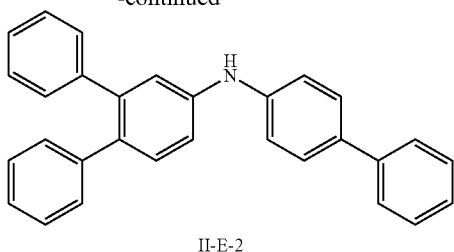

II-E-2

The intermediate II-E-1 (3.80 g, 14.35 mmol), 4-aminobiphenyl (2.55 g, 15.07 mmol), tris(dibenzylideneacetone)dipalladium (0.29 g, 0.31 mmol), 2-(dicyclohexylphosphino)-2',4',6'-triisopropylbiphenyl (0.26 g, 0.63 mmol), and sodium tert-butoxide (2.26 g, 23.5 mmol) were added to methylbenzene (30 mL). The mixture was heated to 108° C. under the nitrogen atmosphere, stirred for 5 h, and then cooled to room temperature. The reaction mixture was washed with deionized water, dried over anhydrous magnesium sulfate, and filtered. Then, the filtrate passed through a short silica gel column, and the solvent was removed under reduced pressure. The crude product was purified by recrystallization with dichloroethane, to obtain intermediate II-E-2 as a light green tablet-shaped solid (4.7 g, 82.31%).

II-E-2 (4.50 g, 11.14 mmol), 4-bromo-4'-iodobiphenyl (6.00 g, 16.7 mmol), tris(dibenzylideneacetone)dipalladium (0.10 g, 0.11 mmol), tri-tert-butylphosphine (0.05 g, 0.22 mmol), and sodium tert-butoxide (1.61 g, 16.71 mmol) were added to methylbenzene (50 mL). The mixture was heated to 108° C. under the nitrogen atmosphere, stirred for 16 h, and then cooled to room temperature. The reaction mixture was washed with water, dried over magnesium sulfate, and then filtered. Then, the solvent was removed from the filtrate under reduced pressure. The residue was purified by silica gel column chromatography and eluted with n-heptane to obtain intermediate II-E as a white solid (3.2 g, 45.71%).

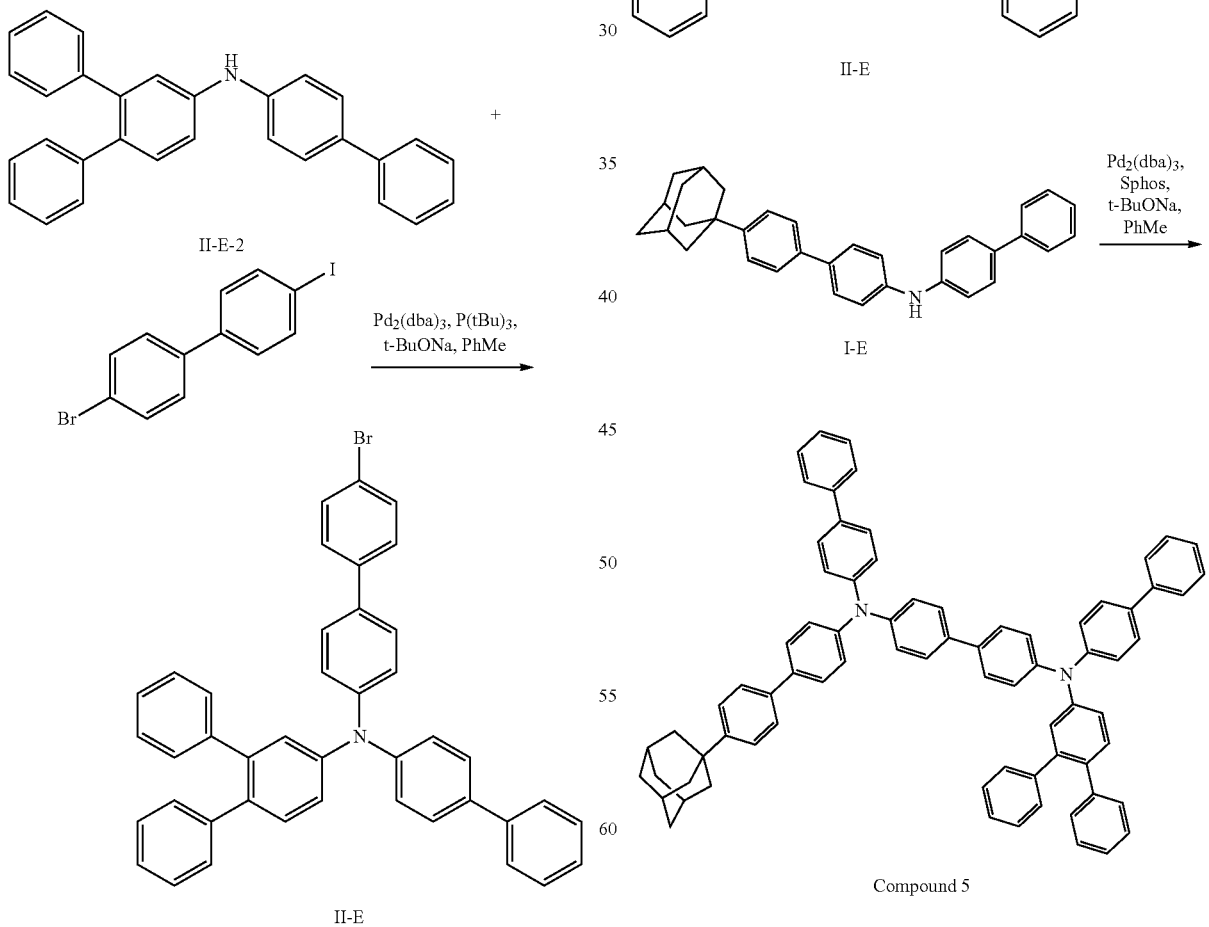

The intermediate I-E (2.30 g, 5.05 mmol), the intermediate II-E (3.2 g, 5.05 mmol), tris(dibenzylideneacetone)dipalladium (0.10 g, 0.11 mmol), 2-(dicyclohexylphosphino)-

2',6'-dimethoxylbiphenyl (0.08 g, 0.22 mmol), and sodium tert-butoxide (0.73 g, 7.58 mmol) were added to methylbenzene (30 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of dichloromethane and n-heptane (1:1) to obtain the crude product. Then, the crude product was purified by recrystallization using a mixture of dichloromethane/n-heptane, to obtain compound 5 as a white solid (2.12 g, 41.9%). MS: m/z=1003.5 (M+H)$^+$ Synthesis Example 6

Synthesis of Compound 6

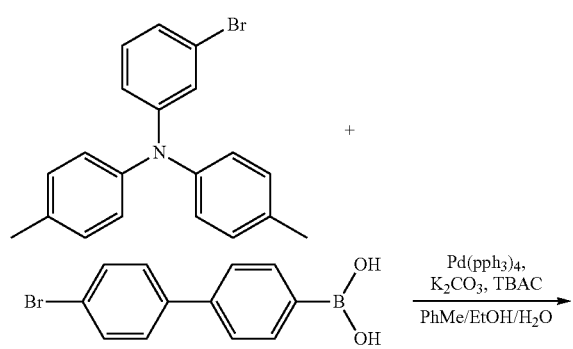

-continued

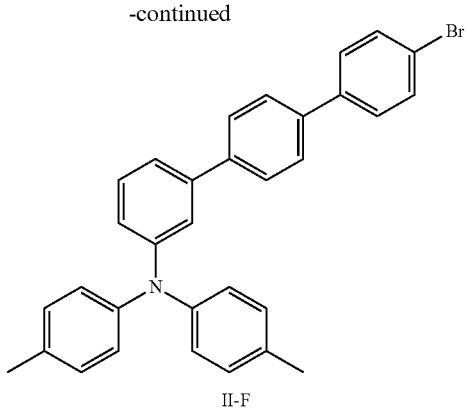

II-F

3-Bromo-N,N-bis(4-methylphenyl)phenylamine (10.0 g, 30.74 mmol), 4'-bromo-4-biphenylboronic acid (5.68 g, 20.50 mmol), tetrakis(triphenylphosphine)palladium (0.47 g, 0.41 mmol), potassium carbonate (6.22 g, 45.09 mmol), tetrabutylammonium chloride (1.14 g, 4.10 mmol), methylbenzene (80 mL), ethanol (20 mL), and deionized water (20 mL) were added to a round bottom flask. The mixture was heated to 78° C. under the nitrogen atmosphere, and stirred for 8 h. The reaction mixture was cooled to room temperature, and extracted with methylbenzene (100 mL). The organic phases were combined, dried over anhydrous magnesium sulfate, and filtered. The solvent was removed under reduced pressure. The obtained crude product was purified by silica gel column chromatography using n-heptane as the mobile phase, and then purified by recrystallization with a mixture of dichloromethane and ethyl acetate, to obtain intermediate II-F as a white solid (3.69 g, 35.69%).

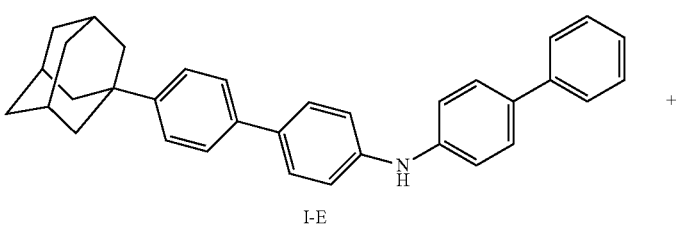

I-E

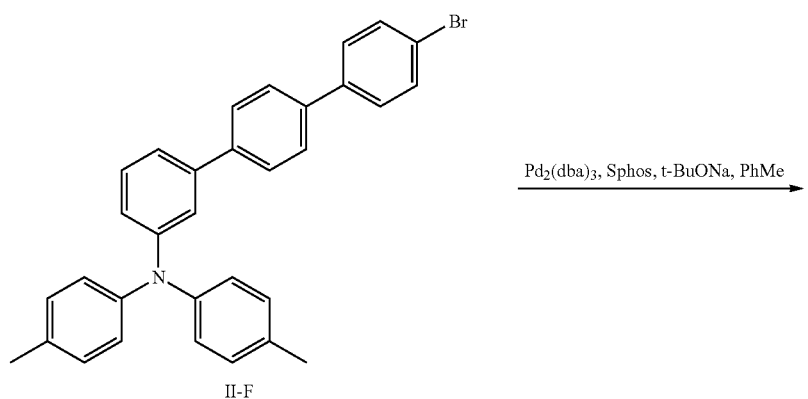

II-F

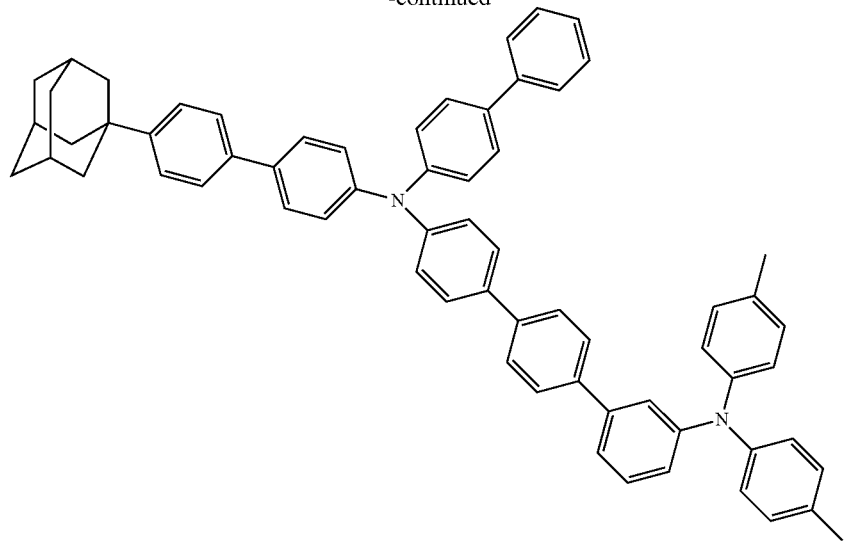

Compound 6

The intermediate I-D (3.50 g, 7.68 mmol) in the above Synthesis Example 4, the intermediate II-F (3.8 g, 7.68 mmol), tris(dibenzylideneacetone)dipalladium (0.14 g, 0.15 mmol), 2-(dicyclohexylphosphino)-2',6'-dimethoxybiphenyl (0.13 g, 0.31 mmol), and sodium tert-butoxide (1.11 g, 11.52 mmol) were added to methylbenzene (30 mL). The mixture was heated to 108° C. under the nitrogen atmosphere, stirred for 3 h, and then cooled to room temperature. After the reaction mixture was filtered, the solvent was removed from the filtrate under reduced pressure; and the crude product was purified by recrystallization using a mixture of dichloromethane and n-heptane, to obtain compound 6 as a white solid (4.17 g, 61.33%). MS: m/z=879.5 (M+H)$^+$ Synthesis Example 7

Synthesis of Compound 7

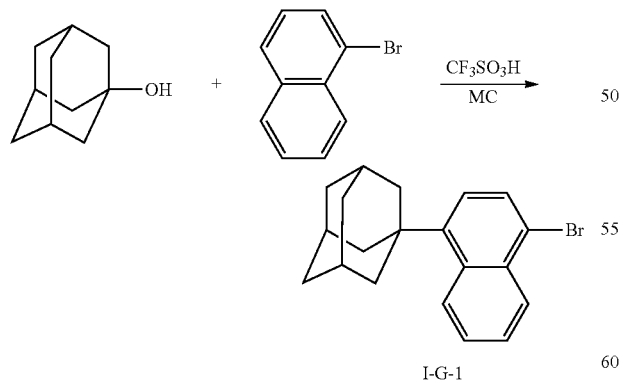

Adamantanol (10.0 g, 65.69 mmol), 1-bromonaphthalene (12.95 g, 62.56 mmol), and dichloromethane (120 mL) were added to a round bottom flask. The mixture was cooled to −20 to −10° C. under the nitrogen atmosphere, trifluoromethanesulfonic acid (14.08 g, 93.84 mmol) was added dropwise, and the mixture was stirred in heat for 6 h. The reaction mixture was washed with deionized water (300 mL) to pH=7, and extracted with dichloromethane (50 mL). The organic phases were combined, dried over anhydrous magnesium sulfate, and filtered. Then, the solvent was removed under reduced pressure; and the obtained crude product was purified by silica gel column chromatography using n-heptane as the mobile phase, to obtain intermediate I-G-1 as a white solid (12.58 g, 58.92%).

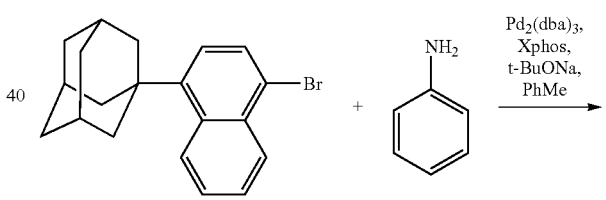

I-G-1

I-G

The intermediate I-G-1 (10 g, 29.30 mmol), phenylamine (2.87 g, 30.77 mmol), tris(dibenzylideneacetone)dipalladium (0.27 g, 0.29 mmol), 2-(dicyclohexylphosphino)-2',4',6'-triisopropylbiphenyl (0.28 g, 0.59 mmol), and sodium tert-butoxide (4.22 g, 43.95 mmol) were added to methylbenzene (80 mL). The mixture was heated to 108° C. under the nitrogen atmosphere, stirred for 3 h, and then cooled to room temperature. The reaction mixture was washed with deionized water, dried over anhydrous magnesium sulfate, and filtered. Then, the filtrate passed through a short silica gel column, and the solvent was removed under reduced pressure. The crude product was purified by recrystallization using a mixture of dichloromethane and n-heptane, to obtain intermediate I-G as an orange solid (7.63 g, 73.65%).

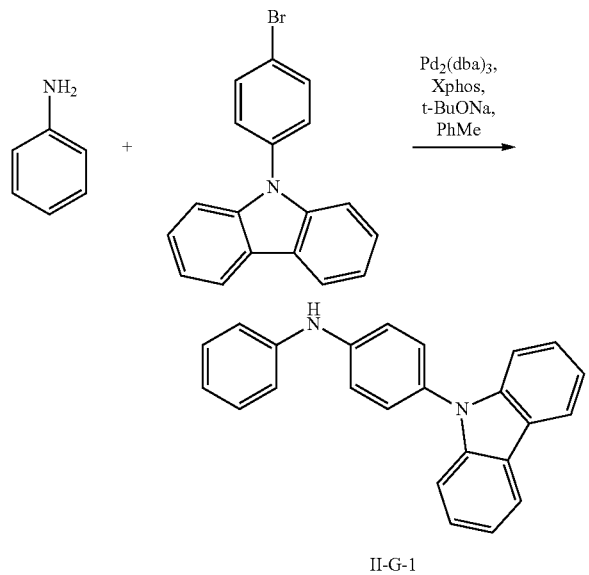

Phenylamine (3.00 g, 32.69 mmol), 9-(4-bromophenyl)-carbazole (10.00 g, 31.13 mmol), tris(dibenzylideneacetone)dipalladium (0.29 g, 0.31 mmol), 2-(dicyclohexylphosphino)-2',4',6'-triisopropylbiphenyl (0.29 g, 0.63 mmol), and sodium tert-butoxide (4.49 g, 46.70 mmol) were added to methylbenzene (80 mL). The mixture was heated to 108° C. under the nitrogen atmosphere, stirred for 6 h, and then cooled to room temperature. The reaction mixture was washed with deionized water, dried over anhydrous magnesium sulfate, and filtered. Then, the filtrate passed through a short silica gel column, and the solvent was removed under reduced pressure. The residue was purified by silica gel column chromatography and eluted with a mixture of dichloromethane/n-heptane (1:3) to obtain the crude product, and then the crude product was purified by recrystallization using a mixture of dichloromethane and n-heptane, to obtain intermediate II-G-1 as a white solid (8.54 g, 82.05%).

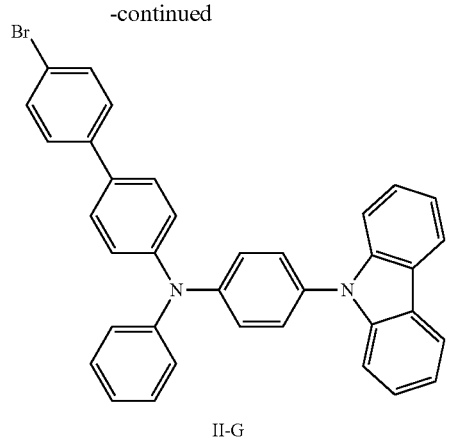

The intermediate II-G-1 (5.00 g, 14.95 mmol), 4-bromo-4'-iodobiphenyl (8.05 g, 22.43 mmol), tris(dibenzylideneacetone)dipalladium (0.14 g, 0.15 mmol), 2-(dicyclohexylphosphino)-2',6'-dimethoxybiphenyl (0.14 g, 0.30 mmol), and sodium tert-butoxide (2.16 g, 22.43 mmol) were added to methylbenzene (80 mL). The mixture was heated to 108° C. under the nitrogen atmosphere, stirred for 16 h, and then cooled to room temperature. After the reaction mixture was filtered, the solvent was removed from the filtrate under reduced pressure to obtain the crude product. The obtained crude product was purified by silica gel column chromatography using n-heptane as the mobile phase. Then, the crude product was purified by recrystallization with n-heptane, to obtain intermediate II-G as a yellow solid (3.52 g, 41.61%).

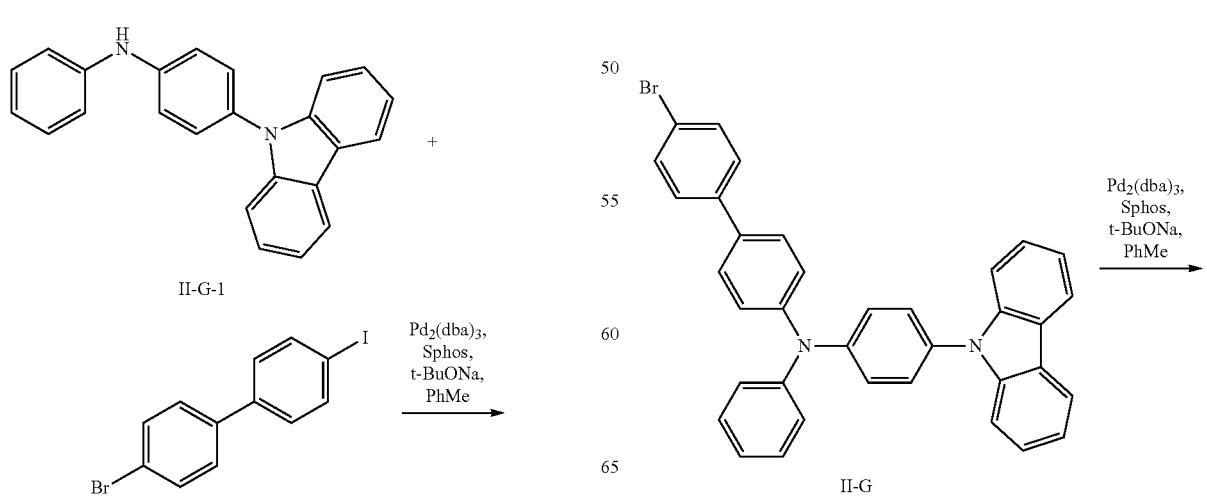

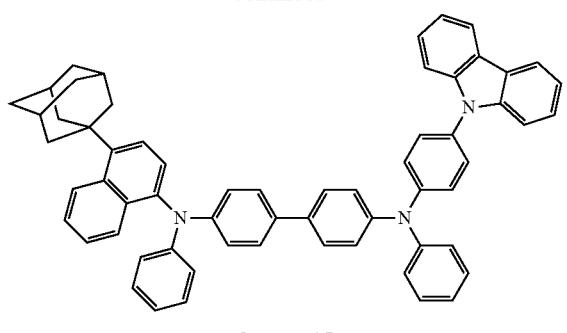

Compound 7

The intermediate I-G (2.20 g, 6.22 mmol), the intermediate II-G (3.52 g, 6.22 mmol), tris(dibenzylideneacetone)dipalladium (0.06 g, 0.06 mmol), 2-(dicyclohexylphosphino)-2',6'-dimethoxylbiphenyl (0.05 g, 0.12 mmol), and sodium tert-butoxide (0.90 g, 9.34 mmol) were added to methylbenzene (30 mL). The mixture was heated to 108° C. under the nitrogen atmosphere, stirred for 2 h, and then cooled to room temperature. After the reaction mixture was filtered, the solvent was removed from the filtrate under reduced pressure to obtain the crude product. The crude product was purified by recrystallization using a mixture of dichloromethane and ethyl acetate, to obtain compound 7 as a white solid (2.31 g, 44.25%). MS: m/z=838.4 (M+H)$^+$ Synthesis Example 8

Synthesis of Compound 8

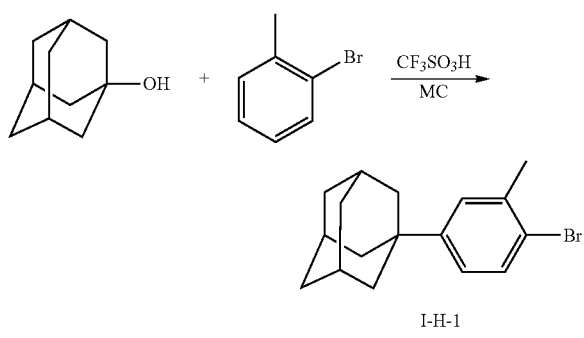

I-H-1

Adamantanol (10.0 g, 65.69 mmol), o-bromomethylbenzene (11.23 g, 65.69 mmol), and dichloromethane (120 mL) were added to a round bottom flask. The mixture was cooled to −45 to −35° C. under the nitrogen atmosphere, trifluoromethanesulfonic acid (14.78 g, 98.53 mmol) was added dropwise, and the mixture was stirred at the temperature for 5 h. The reaction mixture was washed with deionized water (300 mL) to pH=7, and extracted with dichloromethane (50 mL). The organic phases were combined, dried over anhydrous magnesium sulfate, and filtered. The solvent was removed under reduced pressure to obtain the crude product. The obtained crude product was purified by silica gel column chromatography using n-heptane as the mobile phase, to obtain intermediate I-H-1 as a white solid (12.84 g, 63.94%).

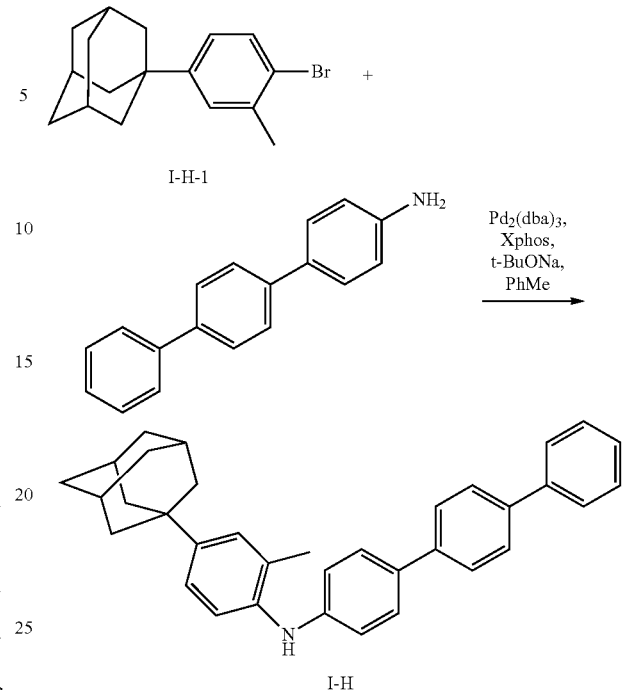

I-H

The intermediate I-H-1 (10.0 g, 32.76 mmol), 4-amino-p-terphenyl (8.28 g, 33.74 mmol), tris(dibenzylideneacetone)dipalladium (0.30 g, 0.33 mmol), 2-(dicyclohexylphosphino)-2',4',6'-triisopropylbiphenyl (0.31 g, 0.66 mmol), and sodium tert-butoxide (4.72 g, 49.14 mmol) were added to methylbenzene (100 mL). The mixture was heated to 108° C. under the nitrogen atmosphere, stirred for 5 h, and then cooled to room temperature. The reaction mixture was washed with deionized water, dried over anhydrous magnesium sulfate, and filtered. Then, the filtrate passed through a short silica gel column, and the solvent was removed under reduced pressure to obtain the crude product. The obtained crude product was purified by silica gel column chromatography using dichloromethane/n-heptane (1:5) as the mobile phase, and then purified by recrystallization using a mixture of dichloromethane and n-heptane, to obtain intermediate I-H as a gray white solid (10.96 g, 71.22%).

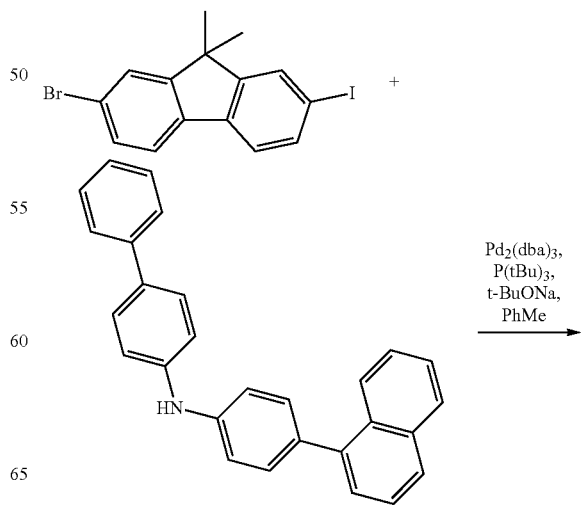

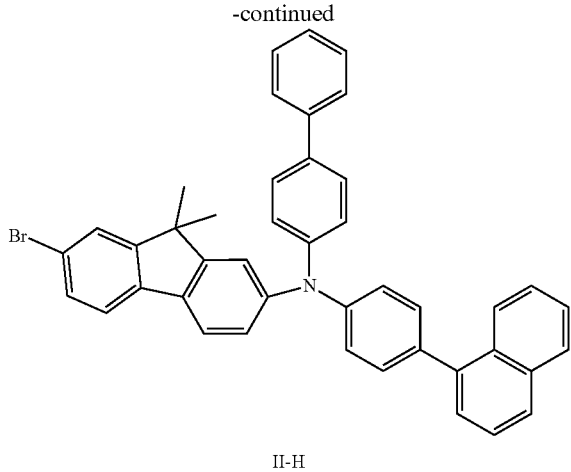

II-H

2-Bromo-7-iodo-9,9-dimethylfluorene (10.0 g, 25.06 mmol), N-(4-(1-naphthyl)phenyl)-4-biphenylamine (6.39 g, 17.21 mmol), tris(dibenzylideneacetone)dipalladium (0.15 g, 0.16 mmol), tri-tert-butylphosphine (0.07 g, 0.33 mmol), and sodium tert-butoxide (2.41 g, 23.5 mmol) were added to methylbenzene (100 mL). The mixture was heated to 18° C. under the nitrogen atmosphere, stirred for 16 h, and then cooled to room temperature. After the reaction mixture was filtered, the solvent was removed from the filtrate under reduced pressure to obtain the crude product. The obtained crude product was purified by silica gel column chromatography using n-heptane as the mobile phase, and then purified by recrystallization with n-heptane, to obtain intermediate II-H as a light yellow solid (3.07 g, 28.58%).

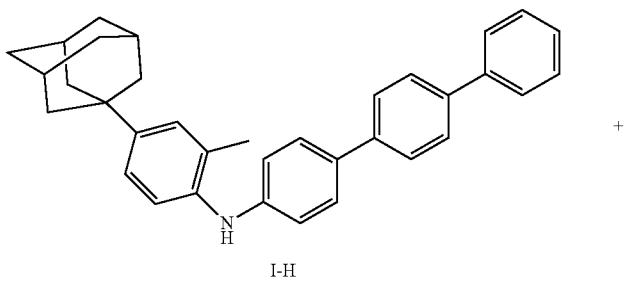

I-H

+

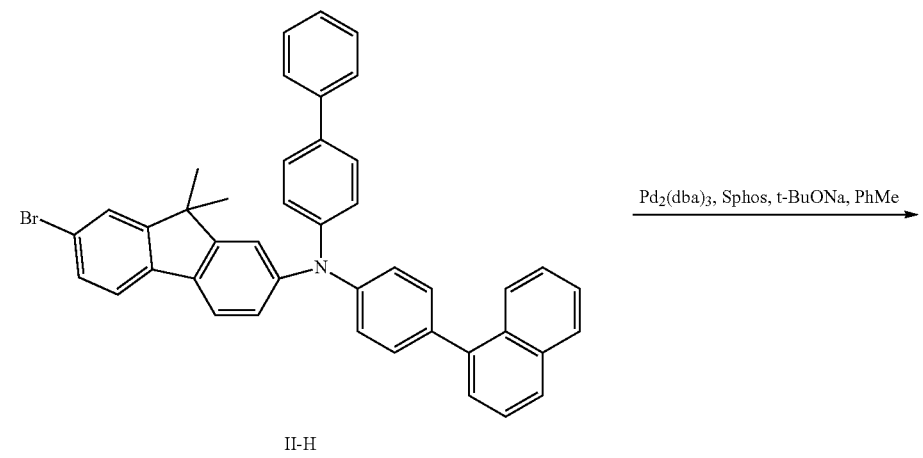

II-H

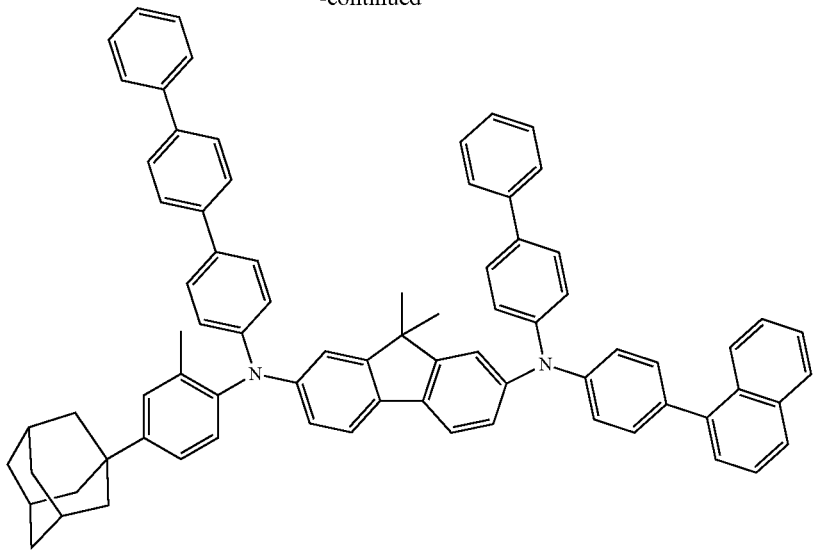

Compound 8

The intermediate I-H (2.20 g, 4.68 mmol), the intermediate 11-H (3.00 g, 4.68 mmol), tris(dibenzylideneacetone)dipalladium (0.09 g, 0.09 mmol), 2-(dicyclohexylphosphino)-2',6'-dimethoxylbiphenyl (0.08 g, 0.19 mmol), and sodium tert-butoxide (0.68 g, 7.03 mmol) were added to methylbenzene (30 mL). The mixture was heated to 108° C. under the nitrogen atmosphere, stirred for 4 h, and then cooled to room temperature. After the reaction mixture was filtered, the solvent was removed from the filtrate under reduced pressure to obtain the crude product. The crude product was purified by recrystallization using a mixture of dichloromethane and ethyl acetate, to obtain compound 8 as a white solid (2.18 g, 45.13%). MS: m/z=1031.5 (M+H)+

Synthesis Example 9

Sythesis of Compound 9

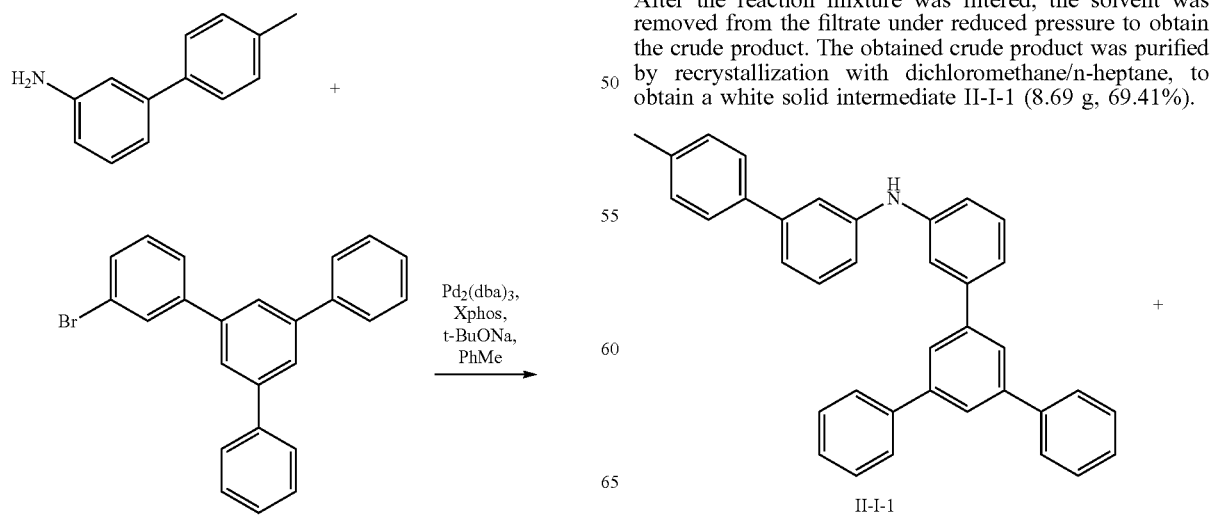

3-amino-4'-methylbiphenyl (5.00 g, 27.29 mmol), 3-bromo-5'-phenyl-1,1':3',1''-terphenyl (10.21 g, 26.49 mmol), tris(dibenzylideneacetone)dipalladium (0.49 g, 0.53 mmol), 2-(dicyclohexylphosphino)-2',4',6'-triisopropylbiphenyl (0.50 g, 1.06 mmol), and sodium tert-butoxide (3.82 g, 39.74 mmol) were added to methylbenzene (100 mL). The mixture was heated to 108° C. under the nitrogen atmosphere, stirred for 6 h, and then cooled to room temperature. After the reaction mixture was filtered, the solvent was removed from the filtrate under reduced pressure to obtain the crude product. The obtained crude product was purified by recrystallization with dichloromethane/n-heptane, to obtain a white solid intermediate II-I-1 (8.69 g, 69.41%).

II-I-1

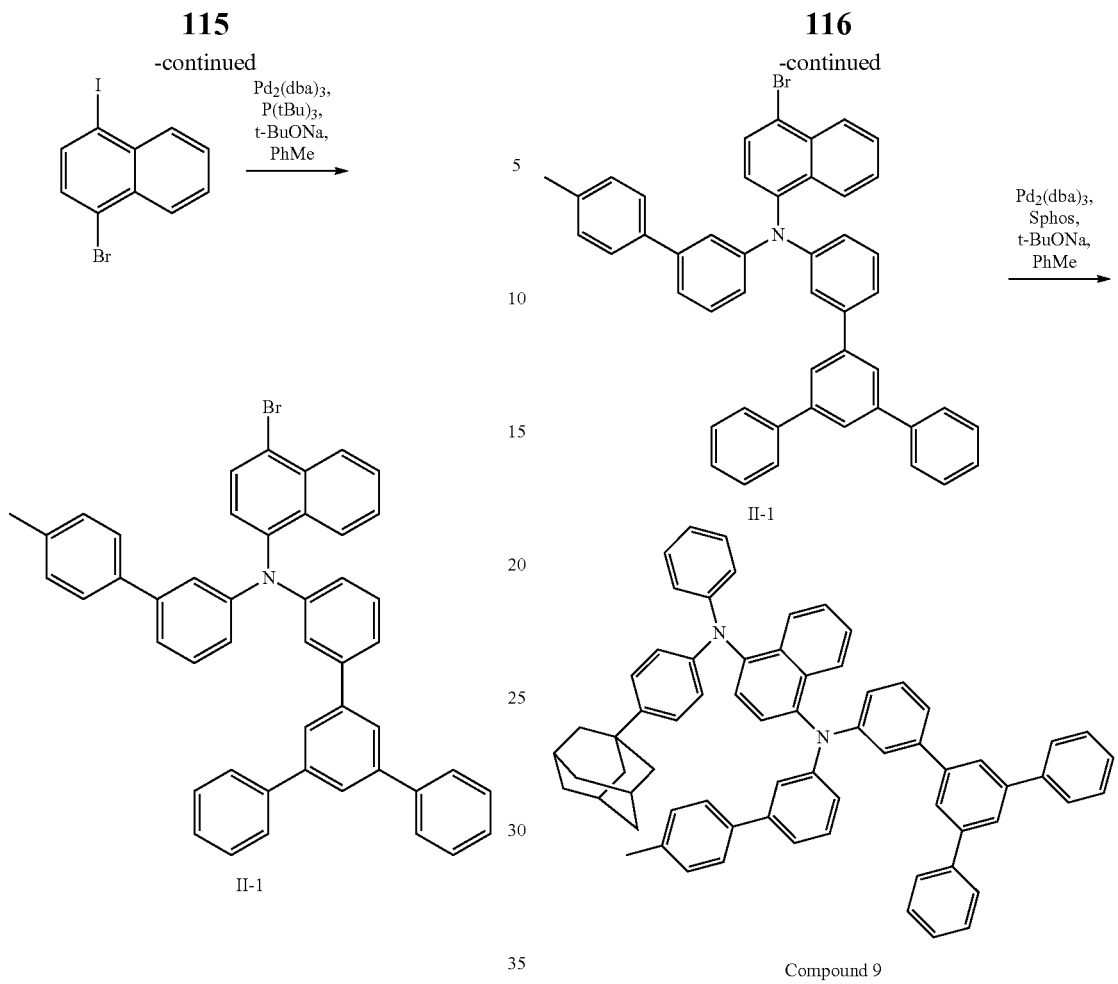

II-1

Compound 9

The intermediate II-I-1 (5.00 g, 10.25 mmol), 1-bromo-4-iodonaphthalene (5.12 g, 15.38 mmol), tris(dibenzylideneacetone)dipalladium (0.19 g, 0.21 mmol), tri-tert-butylphosphine (0.08 g, 0.41 mmol), and sodium tert-butoxide (1.48 g, 15.38 mmol) were added to methylbenzene (50 mL). The mixture was heated to 108° C. under the nitrogen atmosphere, stirred for 7 h, and then cooled to room temperature. After the reaction mixture was filtered, the solvent was removed from the filtrate under reduced pressure to obtain the crude product. The obtained crude product was purified by silica gel column chromatography using dichloromethane/n-heptane (1:8) as the mobile phase, and then purified by recrystallization with dichloromethane/n-heptane, to obtain intermediate II-1 as a gray white solid (3.61 g, 54.86%).

The intermediate I-A (1.70 g, 5.60 mmol) in the above Synthesis Example 1, the intermediate II-1 (3.60 g, 5.60 mmol), tris(dibenzylideneacetone)dipalladium (0.10 g, 0.11 mmol), 2-(dicyclohexylphosphino)-2',6'-dimethoxybiphenyl (0.09 g, 0.22 mmol), and sodium tert-butoxide (0.81 g, 8.4 mmol) were added to methylbenzene (30 mL). The mixture was heated to 108° C. under the nitrogen atmosphere, stirred for 4 h, and then cooled to room temperature.

After the reaction mixture was filtered, the solvent was removed from the filtrate under reduced pressure to obtain the crude product; and the crude product was purified by recrystallization using a mixture of dichloromethane and ethyl acetate, to obtain compound 9 as a white solid (2.04 g, 39.84%). MS: m/z=915.5 (M+H)+

Synthesis Example 10

Synthesis of Compound 10

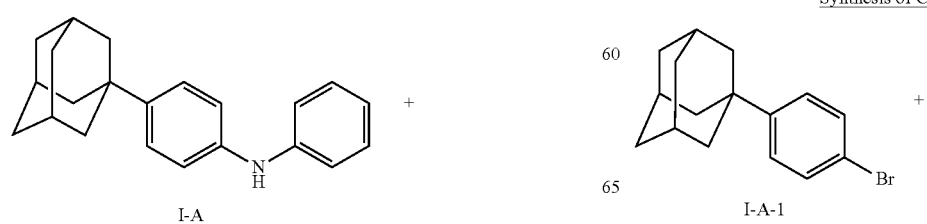

I-A

I-A-1

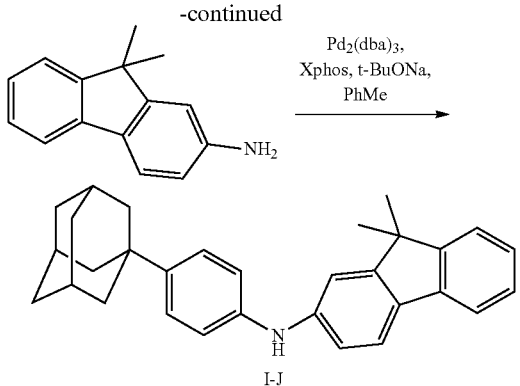

I-J

The intermediate I-A-1 (5.00 g, 17.17 mmol) in the above Synthesis Example 1, 2-amino-9,9-dimethylfluorene (3.70 g, 17.68 mmol), tris(dibenzylideneacetone)dipalladium (0.31 g, 0.34 mmol), 2-(dicyclohexylphosphino)-2',4',6'-triisopropylbiphenyl (0.32 g, 0.69 mmol), and sodium tert-butoxide (2.47 g, 25.75 mmol) were added to methylbenzene (50 mL). The mixture was heated to 108° C. under the nitrogen atmosphere, stirred for 3 h, and then cooled to room temperature. The reaction mixture was washed with deionized water, dried over anhydrous magnesium sulfate, and filtered. Then, the filtrate passed through a short silica gel column, and the solvent was removed under reduced pressure to obtain the crude product. The crude product was purified by recrystallization using a mixture of dichloromethane and n-heptane, to obtain intermediate I-J as a white solid (5.85 g, 81.25%).

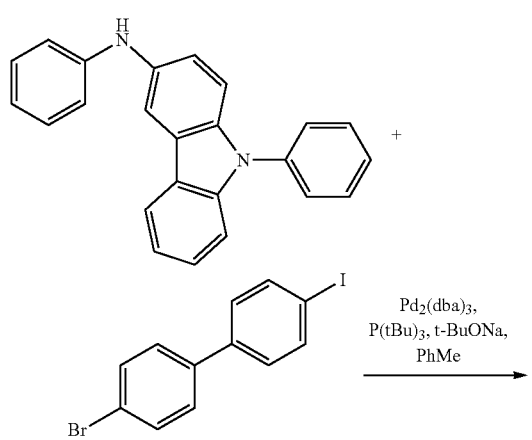

II-J

N,9-diphenyl-9H-carbazol-3-amine (5.00 g, 14.95 mmol), 4-bromo-4'-iodobiphenyl (8.05 g, 22.43 mmol), tris(dibenzylideneacetone)dipalladium (0.27 g, 0.30 mmol), tri-tert-butylphosphine (0.12 g, 0.60 mmol), and sodium tert-butoxide (2.16 g, 22.43 mmol) were added to methylbenzene (80 mL). The mixture was heated to 108° C. under the nitrogen atmosphere, stirred for 6 h, and then cooled to room temperature. After the reaction mixture was filtered, the solvent was removed from the filtrate under reduced pressure to obtain the crude product. The obtained crude product was purified by silica gel column chromatography using n-heptane as the mobile phase, and then purified by recrystallization with a mixture of dichloromethane and n-heptane, to obtain intermediate II-J as a yellow solid (3.10 g, 36.64%).

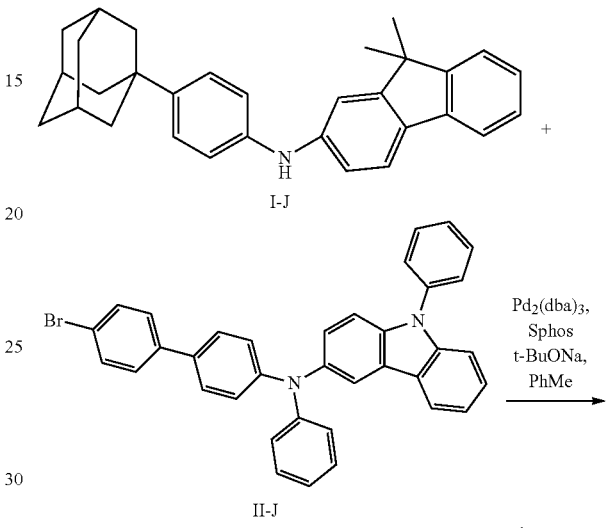

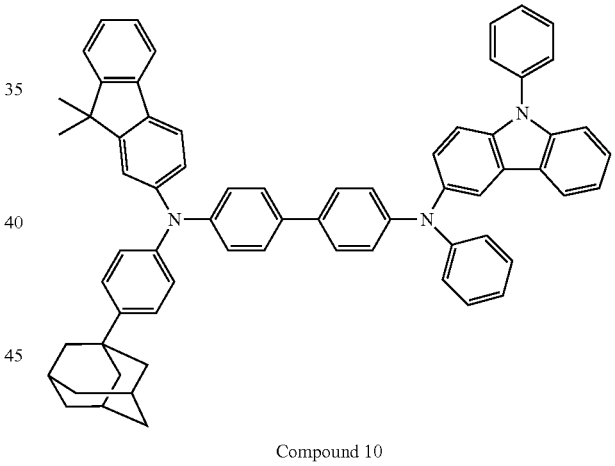

Compound 10

The intermediate I-J (2.30 g, 5.48 mmol), the intermediate II-J (3.10 g, 5.48 mmol), tris(dibenzylideneacetone)dipalladium (0.10 g, 0.11 mmol), 2-(dicyclohexylphosphino)-2',6'-dimethoxylbiphenyl (0.09 g, 0.22 mmol), and sodium tert-butoxide (0.79 g, 8.22 mmol) were added to methylbenzene (30 mL). The mixture was heated to 108° C. under the nitrogen atmosphere, stirred for 2 h, and then cooled to room temperature. After the reaction mixture was filtered, the solvent was removed from the filtrate under reduced pressure to obtain the crude product; and the crude product was purified by recrystallization using a mixture of dichloromethane and n-heptane, to obtain compound 10 as a white solid (2.36 g, 47.58%). MS: m/z=904.5 (M+H)$^+$ Synthesis Example 11

Synthesis of Compound 11

Except that phenylamine was replaced with 5.64 g (15 mmol) of 4-amino-4'-methylbiphenyl, and diphenylamine was replaced with 5.23 g (16.5 mmol) of the intermediate II-E-2, Compound 11 was synthesized using a method identical to that in Synthesis Example 1. MS: m/z=942.3 (M+H)+

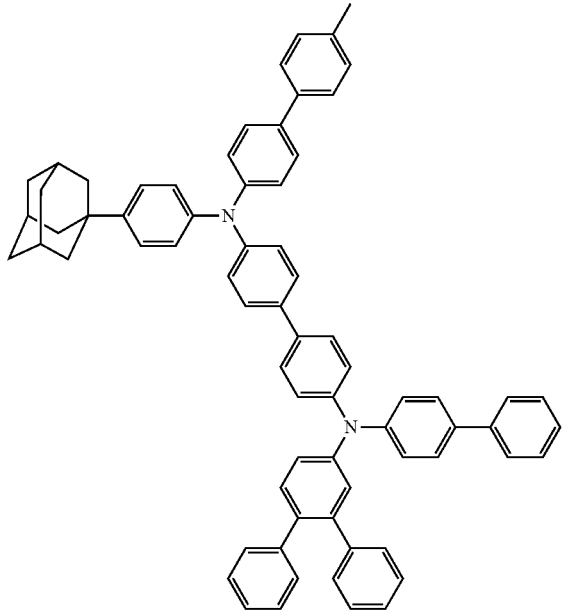 [SMILES: Cc1ccc(-c2ccc(N(c3ccc(-c4ccc(N(c5ccc(-c6ccccc6)cc5)c5ccc(-c6ccccc6)c(-c6ccccc6)c5)cc4)cc3)c3ccc(C45CC6CC(CC(C6)C4)C5)cc3)cc2)cc1]

Synthesis Example 12

Synthesis of Compound 12

Except that phenylamine was replaced with 5.42 g (15 mmol) of 2-naphthylamine, and diphenylamine was replaced with 5.33 g (16.5 mmol) of the intermediate II-E-2, Compound 12 was synthesized using a method identical to that in Synthesis Example 1. MS: m/z=901.4 (M+H)+

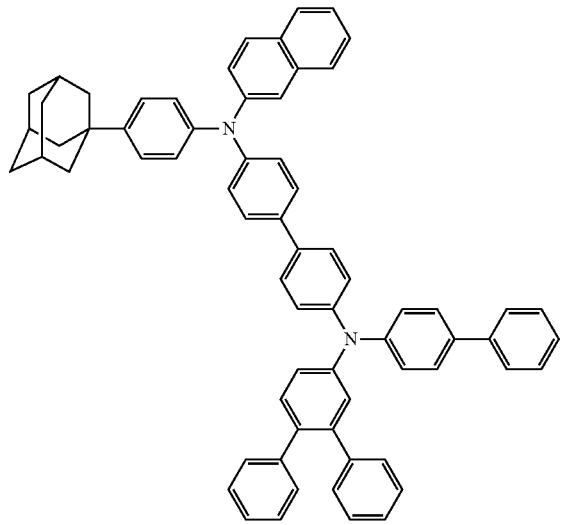 [SMILES: c1ccc(-c2ccc(N(c3ccc(-c4ccc(N(c5ccc(C67CC8CC(CC(C8)C6)C7)cc5)c5ccc6ccccc6c5)cc4)cc3)c3ccc(-c4ccccc4)c(-c4ccccc4)c3)cc2)cc1]

Synthesis Example 13

Synthesis of Compound 13

Except that 4-aminobiphenyl was replaced with 3.11 g (15 mmol) of p-methylphenylamine, 3-bromo-N,N-bis(4-methylphenyl)phenylamine was replaced with 4-bromo-N,N-bis(4-methylphenyl)phenylamine, and 4'-bromo-4-biphenylboronic acid was replaced with 5.06 g (16.5 mmol) of 4-bromo-2,3-dimethylbiphenylboronic acid, Compound 13 was synthesized using a method identical to that in Synthesis Example 6. MS: m/z=770.1 (M+H)+

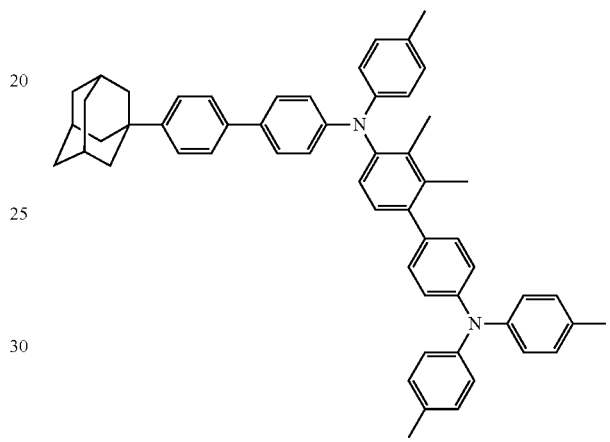

Synthesis Example 14

Synthesis of Compound 14

Except that bromobenzene was replaced with 4.96 g (15 mmol) of 2-bromobiphenyl, an intermediate I-S was prepared using a synthetic route identical to that of the intermediate I-A, and then I-A was replaced with I-S, Compound 14 was synthesized using a method identical to that in Synthesis Example 3. MS: m/z=790.0 (M+H)+

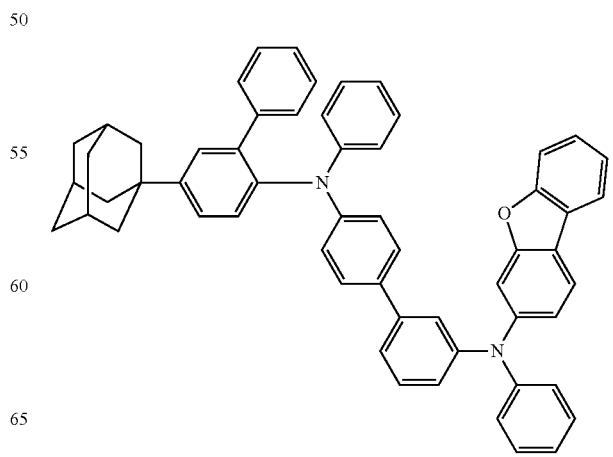

Synthesis Example 15

Synthesis of Compound 15

Except that phenylamine was replaced with 5.73 g (15 mmol) of 3-aminobiphenyl, Compound 15 was synthesized using a method identical to that in Synthesis Example 1. MS: m/z=699.9 (M+H)+

Synthesis Example 16

Synthesis of Compound 16

Except that 4-bromo-4'-iodobiphenyl was replaced with 5.64 g (15 mmol) of 3-bromo-4'-iodobiphenyl, Compound 16 was synthesized using a method identical to that in Synthesis Example 1. MS: m/z=623.9 (M+H)+ MS: m/z=623.9 (M+H)+

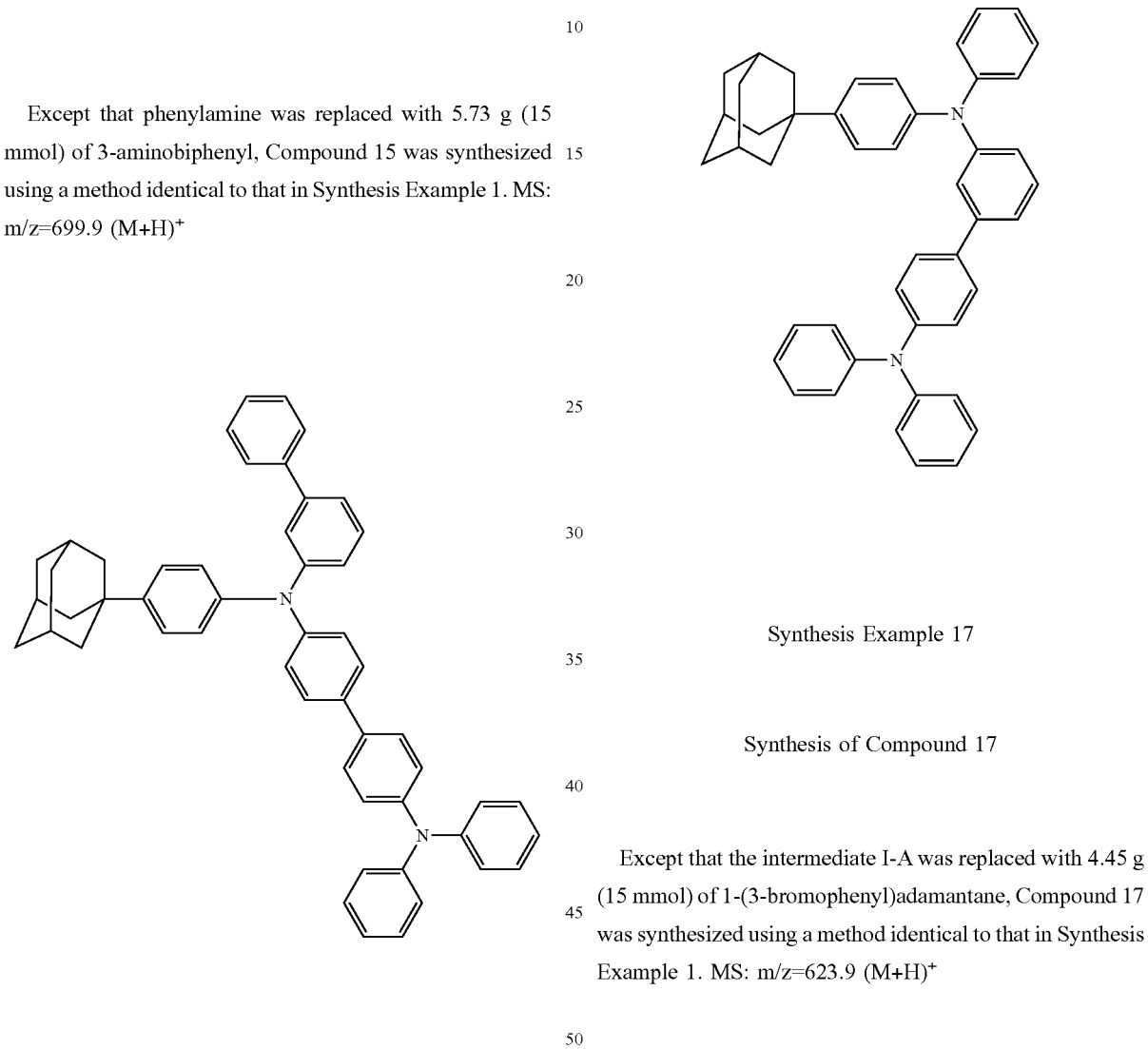

Synthesis Example 17

Synthesis of Compound 17

Except that the intermediate I-A was replaced with 4.45 g (15 mmol) of 1-(3-bromophenyl)adamantane, Compound 17 was synthesized using a method identical to that in Synthesis Example 1. MS: m/z=623.9 (M+H)+

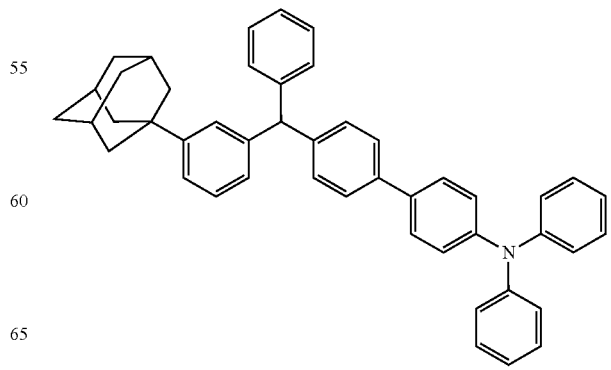

Synthesis Example 18

Synthesis of Compound 18

Except that 3-bromo-N,N-bis(4-methylphenyl)phenylamine, and 4'-bromo-4-biphenylboronic acid were replaced with 5.28 g (15 mmol) of 4-aminobiphenyl, 5.35 g (16.5 mmol) of 4-bromo-4'-methylbiphenyl, and 4.29 g (13.5 mmol) of p-chlorophenylboronic acid, Compound 18 was synthesized using a method identical to that in Synthesis Example 6. MS: m/z=1017.5 (M+H)$^+$

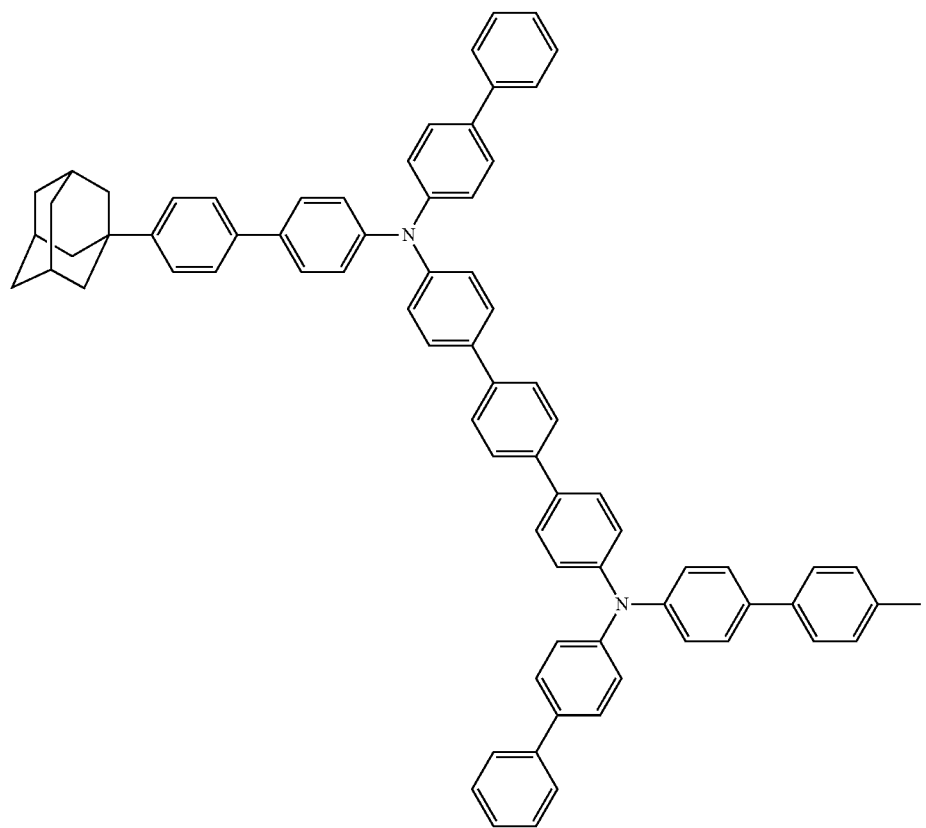 [SMILES: Cc1ccc(-c2ccc(N(c3ccc(-c4ccccc4)cc3)c3ccc(-c4ccc(-c5ccc(N(c6ccc(-c7ccccc7)cc6)c6ccc(-c7ccc(C89CC%10CC(CC(C%10)C8)C9)cc7)cc6)cc5)cc4)cc3)cc2)cc1]

Synthesis Example 19

Synthesis of Compound 19

Except that 3-bromo-N,N-bis(4-methylphenyl)phenylamine, and 4'-bromo-4-biphenylboronic acid were replaced with 9-(4-bromophenyl)carbazole, phenylamine, and p-chlorophenylboronic acid, Compound 19 was synthesized using a method identical to that in Synthesis Example 6. MS: m/z=1016.5 (M+H)$^+$

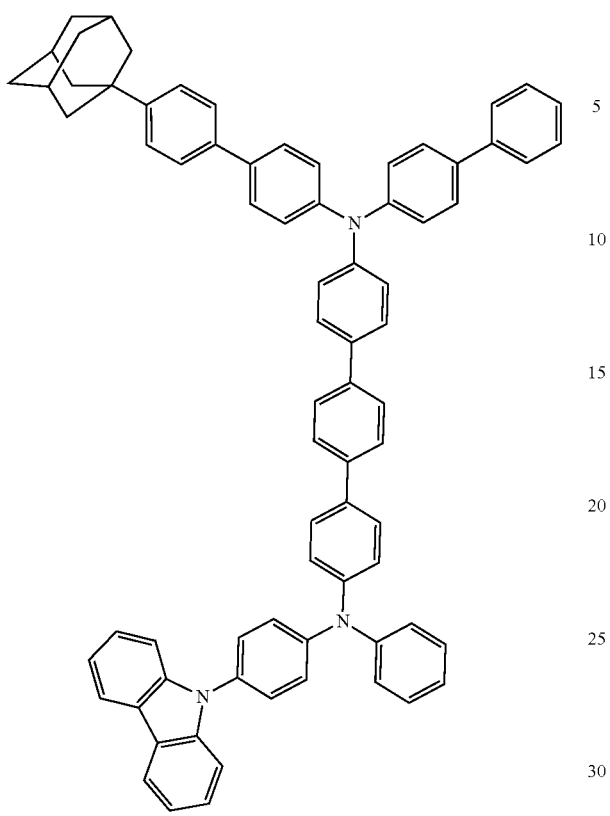

Synthesis Example 20

Synthesis of Compound 20

Except using 5.17 g (15 mmol) of diphenylamine, 5.81 g (16.5 mmol) of 4-bromo-4'-iodo-biphenyl, and 4.29 g (13.5 mmol) of m-chlorophenylboronic acid, Compound 22 was synthesized using a method identical to that in Synthesis Example 5. MS: m/z=775.4 (M+H)$^+$

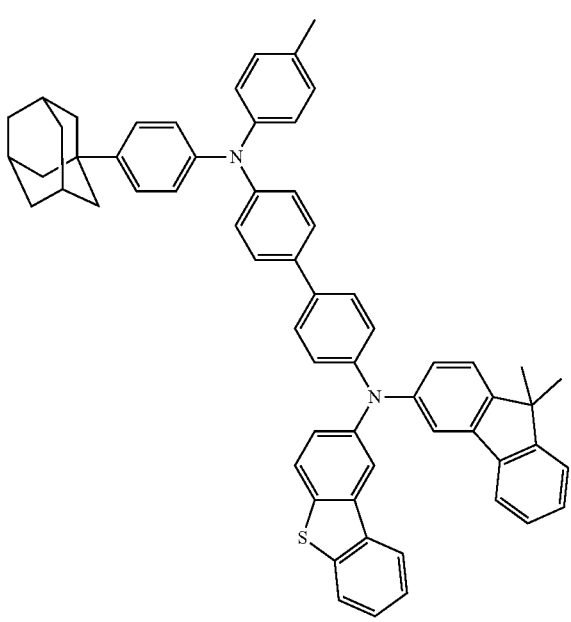 [SMILES: Cc1ccc(N(c2ccc(-c3ccc(N(c4ccc5c(c4)-c4ccccc4C5(C)C)c4ccc5sc6ccccc6c5c4)cc3)cc2)c2ccc(C34CC5CC(CC(C5)C3)C4)cc2)cc1]

Synthesis Example 21

Synthesis of Compound 21

Except that diphenylamine and phenylamine were replaced with 4-chlorobiphenyl-4'-boric acid and 4-aminobiphenyl, Compound 21 was synthesized using a method identical to that in Synthesis Example 1. MS: m/z=851.5 (M+H)$^+$

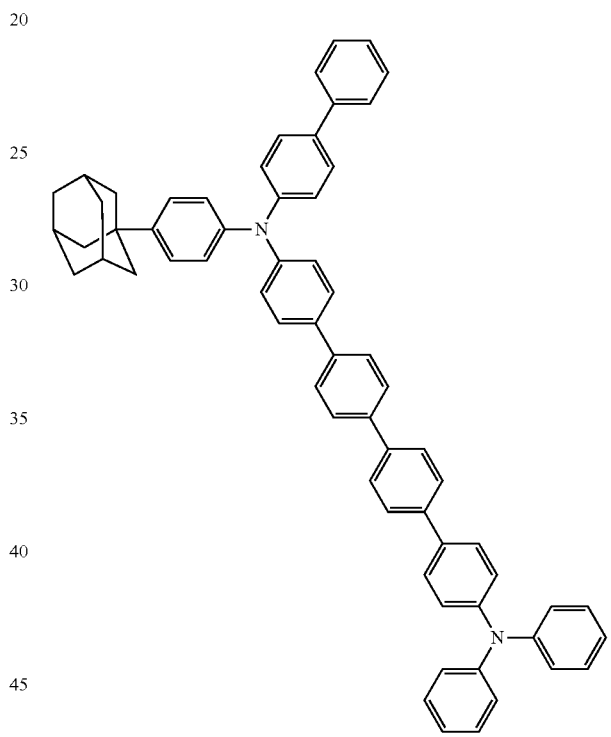

Synthesis Example 22

Synthesis of Compound 22

Except that diphenylamine and phenylamine were replaced with 4-chlorobiphenyl-3'boric acid and 2-amino-9,9-dimethylfluorene, Compound 22 was synthesized using a method identical to that in Synthesis Example 1. MS: m/z=891.5 (M+H)$^+$

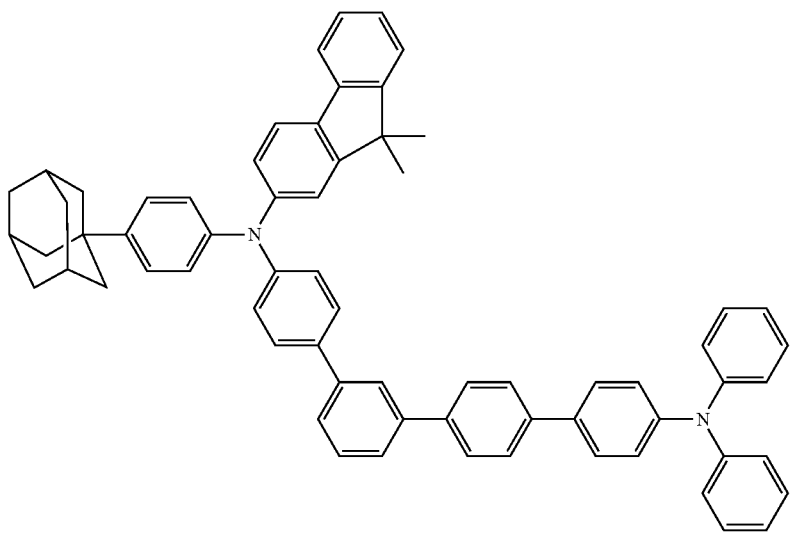 [SMILES: CC1(C)c2ccccc2-c2ccc(N(c3ccc(-c4cccc(-c5ccc(-c6ccc(N(c7ccccc7)c7ccccc7)cc6)cc5)c4)cc3)c3ccc(C45CC6CC(CC(C6)C4)C5)cc3)cc21]

Synthesis Example 23

Synthesis of Compound 23

Except that diphenylamine was replaced with 3-dibenzothiophene and 3-bromodibenzofuran, Compound 23 was synthesized using a method identical to that in Synthesis Example 1. MS: m/z=819.3 (M+H)$^+$

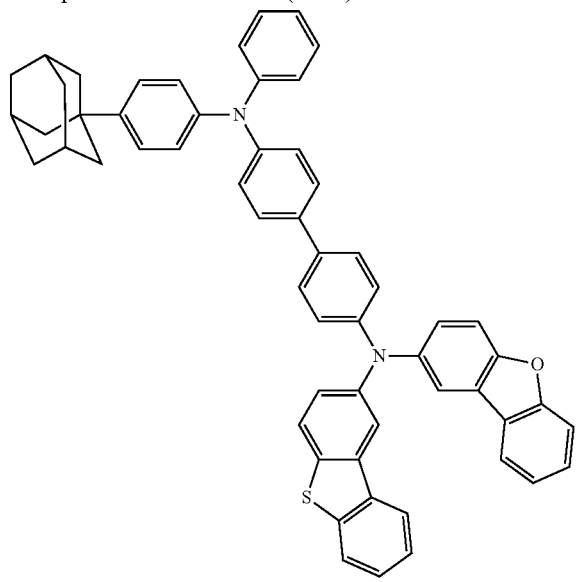

Synthesis Example 24

Synthesis of Compound 24

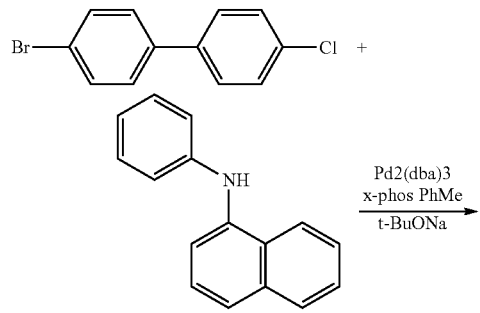

-continued

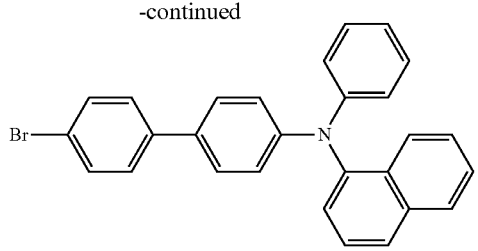

Phenyl-1-naphthylamine (21.9 g, 100 mmol), 4-bromo-4'-chlorobiphenyl (26.7 g, 100 mmol), tris(dibenzylideneacetone)dipalladium (0.10 g, 0.1 mmol), X-PHOS (0.05 g, 0.2 mmol), and sodium tert-butoxide (1.61 g, 150 mmol) were added to methylbenzene (200 mL). The mixture was heated to 108° C. under the nitrogen atmosphere, stirred for 6 h, and then cooled to room temperature. The reaction mixture was washed with water, dried over magnesium sulfate, and then filtered. Then, the solvent was removed from the filtrate under reduced pressure to obtain the crude product. The crude product was purified by silica gel column chromatography and eluted with n-heptane to obtain intermediate as a white solid (27.6 g, 68%).

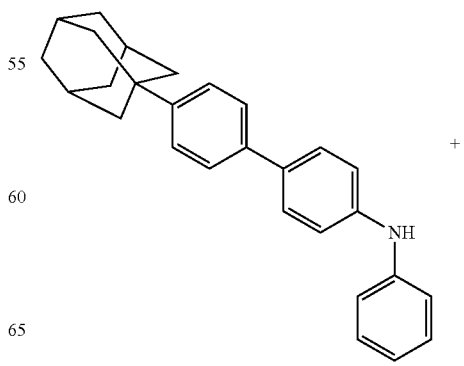

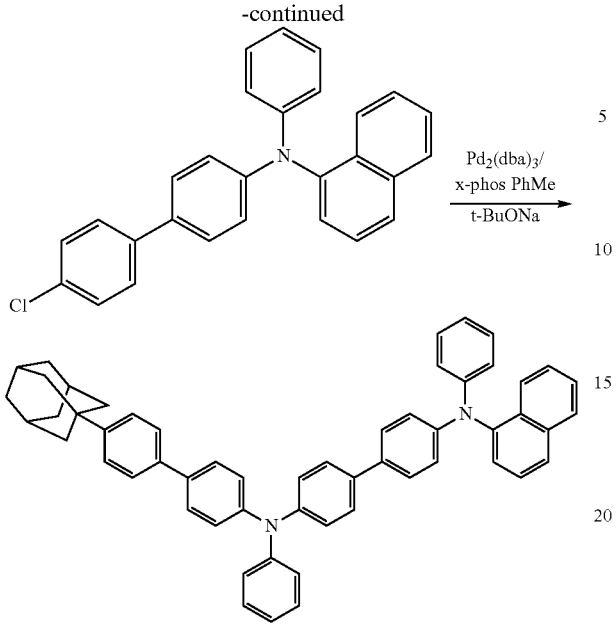

The intermediate (8.12 g, 20 mmol) synthesized above, the intermediate II-C (7.58 g, 20 mmol), tris(dibenzylideneacetone)dipalladium (0.018 g, 0.02 mmol), 2-(dicyclohexylphosphino)-2',4',6'-triisopropylbiphenyl (0.019 g, 0.04 mmol), and sodium tert-butoxide (2.88 g, 30 mmol) were added to methylbenzene (100 mL). The mixture was heated to 108° C. under the nitrogen atmosphere, stirred for 2 h, and then cooled to room temperature. After the reaction mixture was filtered, the solvent was removed from the filtrate under reduced pressure to obtain the residue. The residue was purified by silica gel column chromatography and eluted with a mixture of dichloromethane/n-heptane (1:3). Then, the crude product was purified by recrystallization using a mixture of dichloromethane and ethyl acetate, to obtain compound as a white solid (7.79 g, 52%). MS: m/z=749.3 (M+H)+

$^1$HNMR (400 MHz, CD$_2$Cl$_2$): 7.97 (d, 1H), 7.92 (d, 1H), 7.82 (d, 1H), 7.54-7.36 (m, 14H), 7.36 (t, 2H), 7.21 (t, 2H), 7.15-7.12 (m, 6H), 7.07-7.04 (m, 5H), 6.96 (t, 1H), 2.11-2.10 (m, 3H), 1.96-1.95 (m, 6H), 1.83-1.77 (m, 6H).

Synthesis Example 25

Synthesis of Compound 25

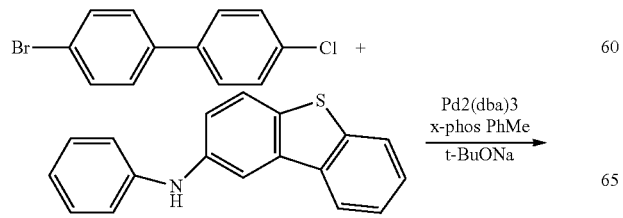

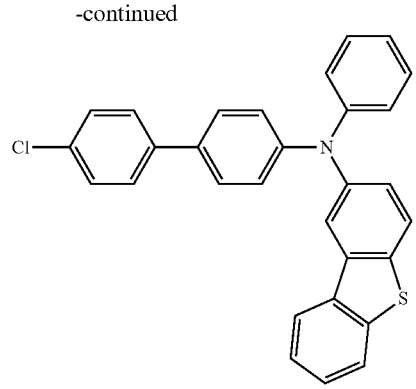

N-phenyldibenzothiophen-2-amine (13.75 g, 50 mmol), 4-bromo-4'-chlorobiphenyl (13.35 g, 50 mmol), tris(dibenzylideneacetone)dipalladium (0.046 g, 0.05 mmol), X-PHOS (0.048 g, 0.1 mmol), and sodium tert-butoxide (7.2 g, 75 mmol) were added to methylbenzene (150 mL). The mixture was heated to 108° C. under the nitrogen atmosphere, stirred for 6 h, and then cooled to room temperature. The reaction mixture was washed with water, dried over magnesium sulfate, and then filtered. Then, the solvent was removed from the filtrate under reduced pressure to obtain the crude product; The residue was purified by silica gel column chromatography and eluted with n-heptane to obtain a white intermediate (15.24 g, 66%).

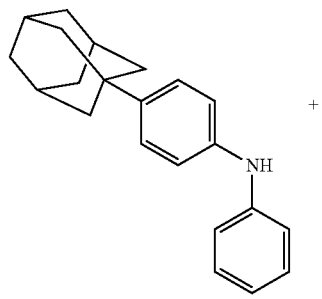

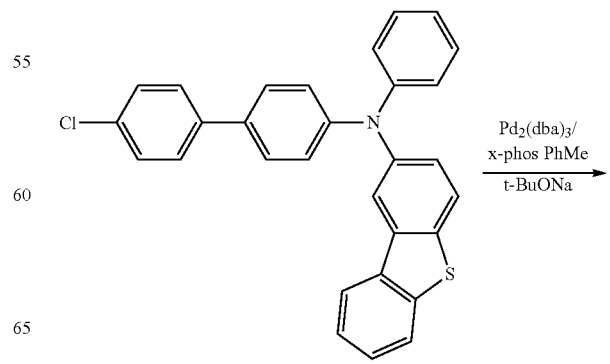

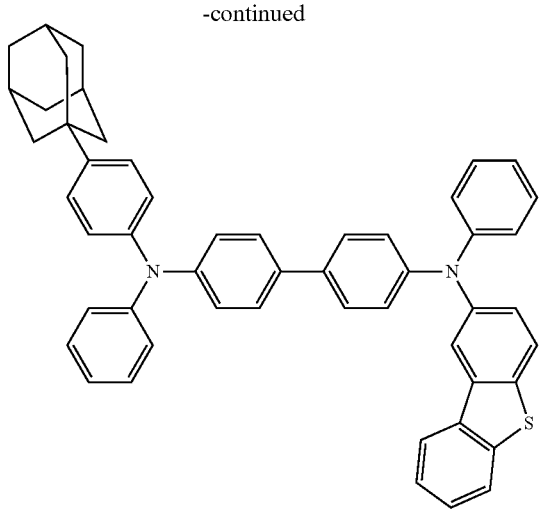

The intermediate (9.24 g, 20 mmol) synthesized above, the intermediate I-A (6.04 g, 20 mmol), tris(dibenzylideneacetone)dipalladium (0.018 g, 0.02 mmol), 2-(dicyclohexylphosphino)-2',4',6'-triisopropylbiphenyl (0.019 g, 0.04 mmol), and sodium tert-butoxide (2.88 g, 30 mmol) were added to methylbenzene (100 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of dichloromethane and n-heptane (1:3) to obtain the crude product. Then, the crude product was purified by recrystallization using a mixture of dichloromethane and ethyl acetate system, to obtain compound as a white solid (8.45 g, 58%). MS: m/z=729.3 (M+H)$^+$ $^1$HNMR (400 MHz, CD$_2$Cl$_2$): 7.99 (d, 1H), 7.94 (s, 1H), 7.85 (d, 1H), 7.77 (d, 1H), 7.47-7.39 (m, 6H), 7.30-7.24 (m, 7H), 7.16-7.00 (m, 12H), 2.08-2.09 (m, 3H), 1.91-1.90 (m, 6H), 1.81-1.75 (dd, 6H).

Synthesis Example 26

Synthesis of Compound 26

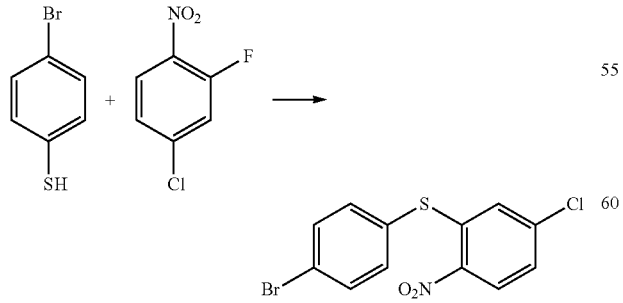

4-Bromobenzenethiol (18.9 g, 100 mmol), 4-chloro-2-fluoronitrobenzene (17.5 g, 100 mmol), and DMF (100 mL) were mixed and stirred, such that the system was dissolved and clear. Potassium carbonate (17.94 g, 130 mmol) was added. The mixture was heated to 80° C.-90° C., and kept at the temperature for 18 h to complete the reaction. The reaction mixture was cooled to 20° C.-30° C., diluted with 20 L of water, fully stirred, and filtered. The filter cake was washed with water for 3 times to neutral, and slurried with ethanol at 20° C.-30° C. The slurry was filtered at room temperature, and oven-dried at 50-60° C. to dryness, to obtain a light yellow solid (31.01 g, yield 90%).

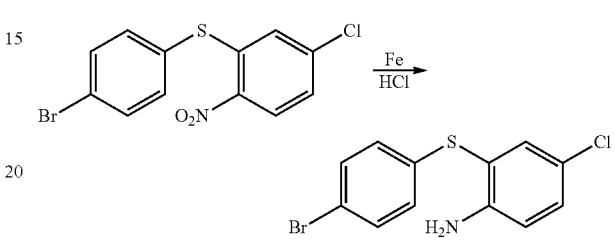

The nitro-intermediate (17.23 g, 50 mmol) obtained in the last step and ethanol (100 mL) were added in the bottle. The iron powder (9.8 g, 175 mmol) was added while stirring, and then the mixture was heated to T=50° C.-60° C., and 5 mL of concentrated hydrochloric acid (diluted 10 times) was added dropwise. The mixture was kept at T=50-60° C. for hours, to complete the reaction. The reaction mixture was cooled to 20-25° C., and filtered through a short column of alumina. The filter cake was rinsed with THF, and then temporarily stored. The filtrates were combined, extracted with water and dichloroethane while stirring for 10 min, and left to stand for 1 h for stratification. The aqueous phase was extracted with dichloroethane once. The organic phases were combined, washed with water to pH=6-7, dried over anhydrous sodium sulfate for 1 h, and filtered. The filter cake was rinsed with dichloroethane. The filtrates were combined, and concentrated under −0.075 MPa to −0.09 MPa at 50-65° C. to dryness until no solvent was separated. In this case, petroleum ether was added while fully stirring. The mixture was cooled to 0-5° C., and the precipitate appeared. Filtered, the filter cake was collected, and oven-dried in a blast drying oven at 40-45° C. for about 6 h, to obtain 13.37 g of a product with a yield of 85%.

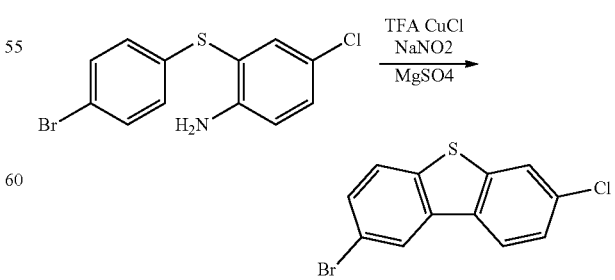

The above amino-intermediate (18.87 g, 60 mmol) was dissolved in 100 mL of dichloroethane until a transparent solution was obtained, and trifluoroacetic acid (13.68 g, 120 mmol) and anhydrous magnesium sulfate (3.6 g, 30 mmol) were added while stirring for 10 min. Sodium nitrite (8.48 g, 132 mmol) was added portionwise, strictly controlled at a temperature of 40° C.-50° C., and kept at the temperature of 40° C.-50° C., to complete the reaction. The reaction mixture was cooled to 20° C.-30° C., and filtered through a silica gel funnel. The filter cake was rinsed with dichloroethane. The combined filtrate was washed with water for 3 to 4 times to neutral, and stratified. The organic phase was dried over anhydrous sodium sulfate, and filtered. The filter cake of anhydrous sodium sulfate was rinsed with dichloroethane. The filtrates were combined, concentrated under −0.075 MPa to −0.09 MPa at 50° C.-65° C. The residue was washed twice by boiling with petroleum ether at 45-50° C. to obtain a solid. The solid was dissolved in methylbenzene, and passed through a column at room temperature. The eluent was concentrated under −0.08 MPa to −0.09 MPa at 65-80° C., cooled for recrystallization, and filtered at T=−5 to 0° C. The filter cake was dried, and dissolved in dichloroethane while refluxing until a transparent solution was obtained, which was recrystallized again, cooled to −5 to 0° C., filtered, and dried at 50-60° C., to obtain 8.03 g with a yield of 45%.

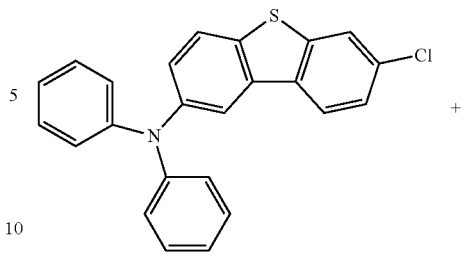

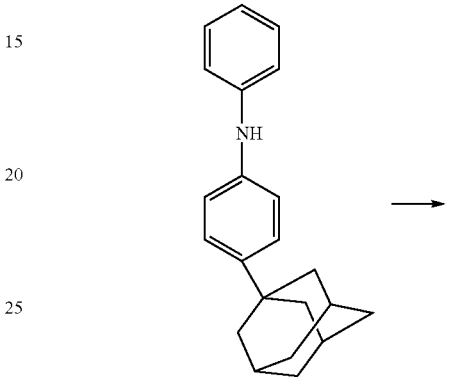

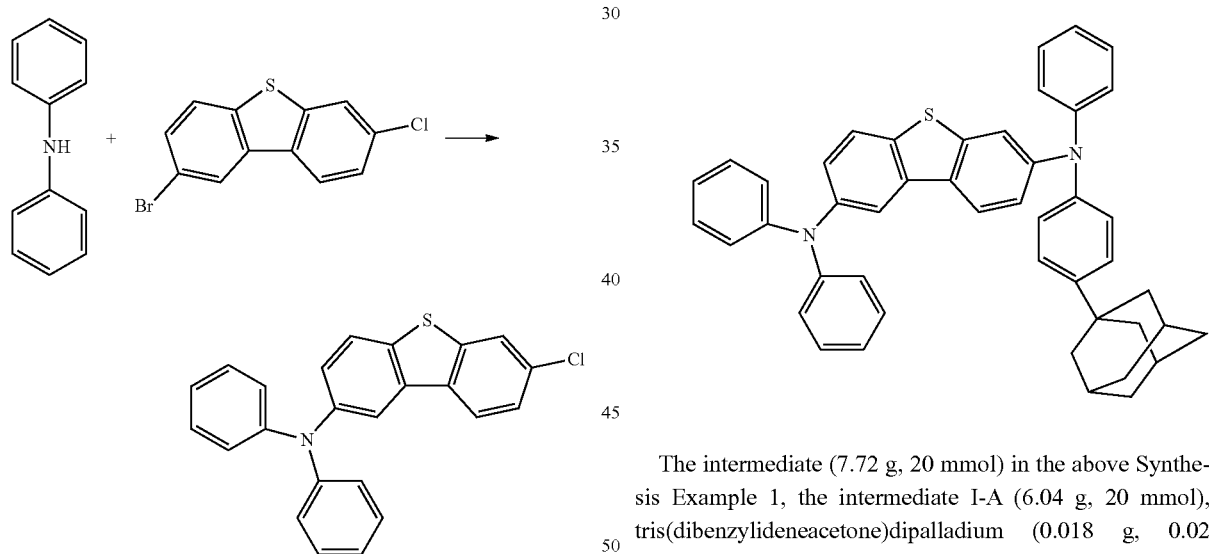

Diphenylamine (8.45 g, 50 mmol), 2-chloro-7-bromo-dibenzothiophene (14.88 g, 50 mmol), tris(dibenzylideneacetone)dipalladium (0.046 g, 0.05 mmol), X-PHOS (0.048 g, 0.1 mmol), and sodium tert-butoxide (7.2 g, 75 mmol) were added to methylbenzene (150 mL). The mixture was heated to 108° C. under the nitrogen atmosphere, stirred for 6 h, and then cooled to room temperature. The reaction mixture was washed with water, dried over magnesium sulfate, and then filtered. Then, the solvent was removed from the filtrate under reduced pressure to obtain the crude product. The residue was purified by silica gel column chromatography and eluted with n-heptane to obtain a white intermediate (13.89 g, 72%).

The intermediate (7.72 g, 20 mmol) in the above Synthesis Example 1, the intermediate I-A (6.04 g, 20 mmol), tris(dibenzylideneacetone)dipalladium (0.018 g, 0.02 mmol), 2-(dicyclohexylphosphino)-2',4',6'-triisopropylbiphenyl (0.019 g, 0.04 mmol), and sodium tert-butoxide (2.88 g, 30 mmol) were added to methylbenzene (100 mL). The mixture was heated to 108° C. under the nitrogen atmosphere, stirred for 2 h, and then cooled to room temperature. After the reaction mixture was filtered, the solvent was removed from the filtrate under reduced pressure to obtain the residue. The residue was purified by silica gel column chromatography and eluted with a mixture of dichloromethane and n-heptane (v:v=1:3) to obtain the crude product. Then, the crude product was purified by recrystallization using a mixture of dichloromethane and ethyl acetate, to obtain compound 26 as a white solid (8.22 g, 63%). MS: m/z=653.3 (M+H)$^+$

Synthesis Example 27

Synthesis of Compound 27

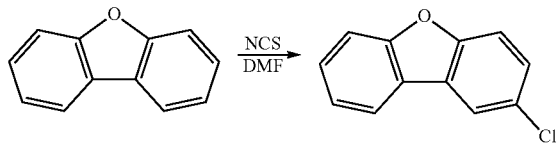

Dibenzofuran (16.8 g, 100 mmol), DMF (150 mL), and NCS (13.3 g, 100 mmol) were heated while stirring, and reacted at 40-50° C. The reaction mixture was brown at the beginning, and then become yellow as the reaction proceeded. The reaction was completed in 7 h. The reaction mixture was poured into water, and a solid precipitated. The solid was recrystallized with n-heptane (m/v=1/3), (dissolved by heating to 95-98° C., naturally cooled to 25-30° C.), filtered and collected the filter cake, repeated the recrystallization operation for 4 times according to the above process. The combined filter cake was dried to obtain 3-chlorodibenzofuran 7.67 g as a white solid with a yield of 38%. The purity of 3-chlorodibenzofuran is HPLC=98.54%.

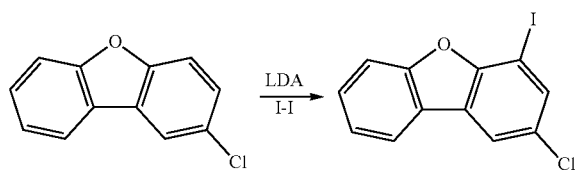

3-Chlorodibenzofuran (20.2 g, 100 mmol) and tetrahydrofuran (200 mL) were stirred under the nitrogen atmosphere, and cooled with liquid nitrogen to −45 to −35° C. 120 mmol of LDA (1 mol/L solution in THF) was added dropwise in 40 min. The reaction mixture was kept at the temperature for 1 h, and then cooled with liquid nitrogen to −95 to −85° C. An iodine solution (29.4 g, 120 mmol of iodine dissolved in 100 mL of THF) was added dropwise in 60 min. After the mixture was kept at the temperature for 40 min, the reaction was ended. After the reaction was ended, an aqueous solution of sodium bisulfate was added to the reaction mixture, which was stirred for 10 min to decolor the reaction mixture, and left to stand for 10 min for stratification. The aqueous phase was extracted twice with 2 L/time ethyl acetate. The organic phases were combined, dried over anhydrous sodium sulfate for 60 min, and concentrated under 0.07 MPa at 60-85° C., to obtain a crude oil. n-Heptane was added to the crude oil. The mixture was heated to 95-98° C., stirred for 60 min, cooled to 15-20° C. to precipitate a solid, and filtered to obtain a crude product.

Recrystallization operation: 1 g of crude product was dissolved in 4 mL of ethyl acetate at 75-80° C., naturally cooled to 20-25° C. to precipitate a solid, and filtered. The filter cake was dried in a blast drying oven at 60-65° C. for 12 h, to obtain 130.00 g of an off-white solid, LC=99.08%. The mother liquor was recycled, and the obtained solid was recrystallized twice to obtain 13.79 g of a solid with a total yield of 42%.

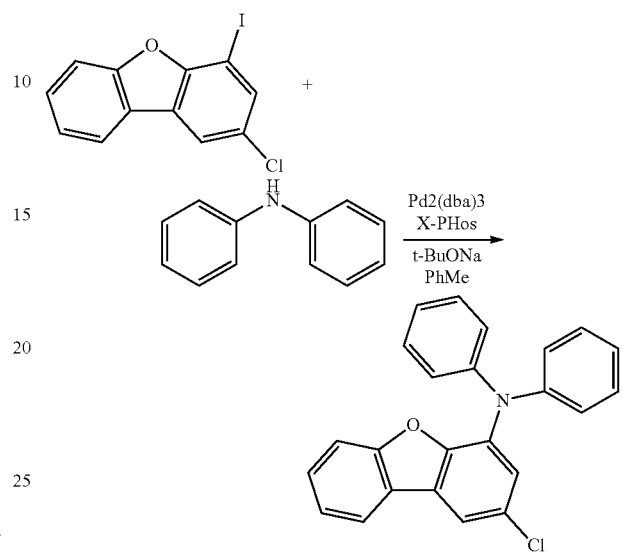

Diphenylamine (8.45 g, 50 mmol), 2-chloro-4-iododibenzofuran (16.42 g, 50 mmol), tris(dibenzylideneacetone)dipalladium (0.046 g, 0.05 mmol), X-PHOS (0.048 g, 0.1 mmol), and sodium tert-butoxide (7.2 g, 75 mmol) were added to methylbenzene (150 mL). The mixture was heated to 108° C. under the nitrogen atmosphere, stirred for 8 h, and then cooled to room temperature. The reaction mixture was washed with water, dried over magnesium sulfate, and then filtered. Then, the solvent was removed from the filtrate under reduced pressure to obtain the crude product. The residue was purified by silica gel column chromatography and eluted with n-heptane to obtain a white intermediate (14.05 g, 76%).

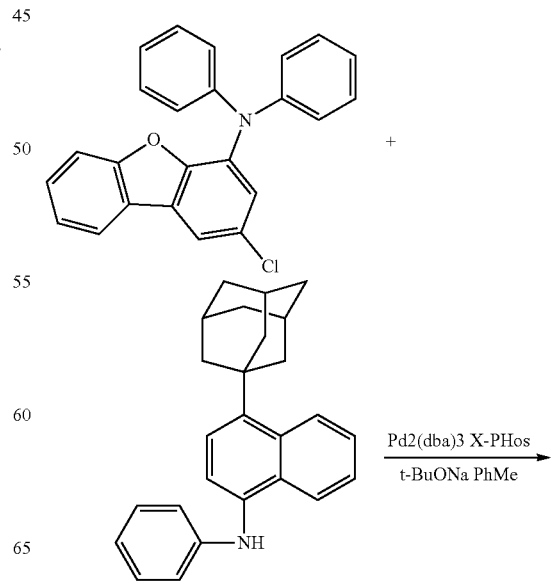

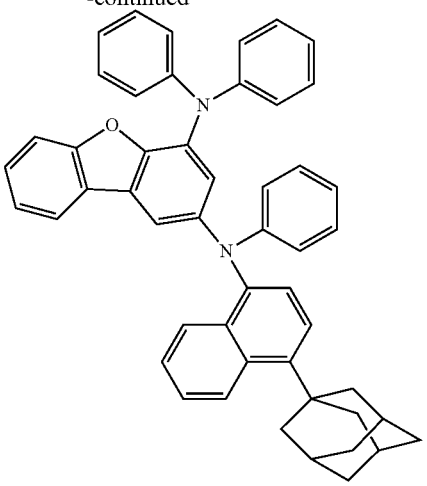

The intermediate (7.40 g, 20 mmol) in the above Synthesis Example, the intermediate I-G (7.06 g, 20 mmol), tris(dibenzylideneacetone)dipalladium (0.018 g, 0.02 mmol), 2-(dicyclohexylphosphino)-2',4',6'-triisopropylbiphenyl (0.019 g, 0.04 mmol), and sodium tert-butoxide (2.88 g, 30 mmol) were added to methylbenzene (100 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of dichloromethane/n-heptane (1:3) to obtain the crude product. Then, the crude product was purified by recrystallization using a mixture of dichloromethane and ethyl acetate, to obtain compound 27 as a white solid (9.61 g, 70%). MS: m/z=687.3 (M+H)$^+$ Synthesis Example 28

Synthesis of Compound 28

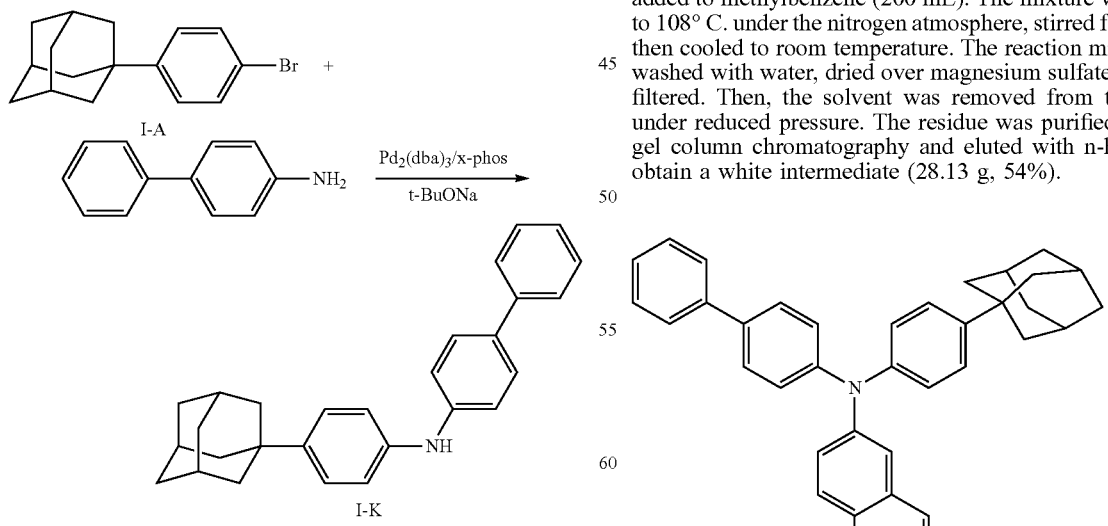

The intermediate I-A (7.0 g, 24.04 mmol), 1,1'-biphenyl-4-amine (4.87 g, 28.84 mmol), tris(dibenzylideneacetone) dipalladium (0.22 g, 0.24 mmol), 2-(dicyclohexylphosphino)-2',4',6'-triisopropylbiphenyl (0.23 g, 0.48 mmol), and sodium tert-butoxide (3.46 g, 36.05 mmol) were added to methylbenzene (70 mL). The mixture was heated to 108° C. under the nitrogen atmosphere, stirred for 3 h, and then cooled to room temperature. The reaction mixture was washed with deionized water, dried over anhydrous magnesium sulfate, and filtered. Then, the filtrate passed through a short silica gel column, and the solvent was removed under reduced pressure to obtain the crude product. The crude product was purified by recrystallization using a mixture of dichloromethane and n-heptane, to obtain intermediate I-K as a light green solid (7.30 g, 80%).

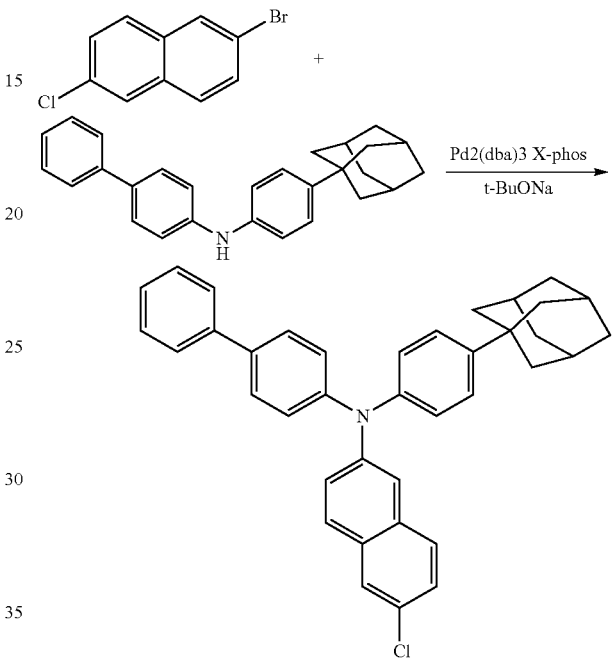

2-Bromo-6-chloro-naphthalene (24.1 g, 100 mmol), the intermediate I-K (37.9 g, 100 mmol), tris(dibenzylideneacetone)dipalladium (0.91 g, 1 mmol), X-Phos (0.95 g, 2 mmol), and sodium tert-butoxide (19.2 g, 200 mmol) were added to methylbenzene (200 mL). The mixture was heated to 108° C. under the nitrogen atmosphere, stirred for 6 h, and then cooled to room temperature. The reaction mixture was washed with water, dried over magnesium sulfate, and then filtered. Then, the solvent was removed from the filtrate under reduced pressure. The residue was purified by silica gel column chromatography and eluted with n-heptane to obtain a white intermediate (28.13 g, 54%).

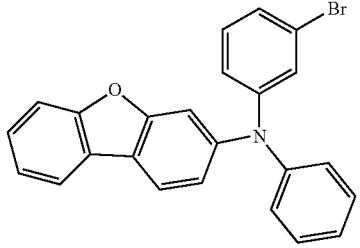

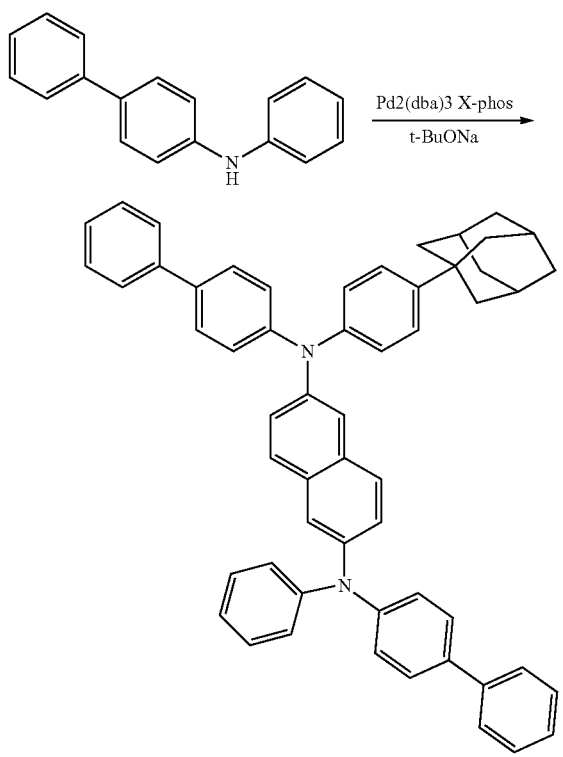

The intermediate (27 g, 50 mmol) synthesized above, phenylbiphenylamine (12.25 g, 50 mmol), tris(dibenzylideneacetone)dipalladium (0.49 g, 0.5 mmol), 2-(dicyclohexylphosphino)-2',4',6'-triisopropylbiphenyl (0.47 g, 1 mmol), and sodium tert-butoxide (9.6 g, 100 mmol) were added to methylbenzene (200 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of dichloromethane/n-heptane (v/v=1:3) to obtain the crude product. Then, the crude product was purified by recrystallization using a mixture of dichloromethane and ethyl acetate, to obtain compound 28 as a white solid (16.10 g, 43%). MS: m/z=749.3 (M+H)$^+$ Synthesis Example 29

Synthesis of Compound 29

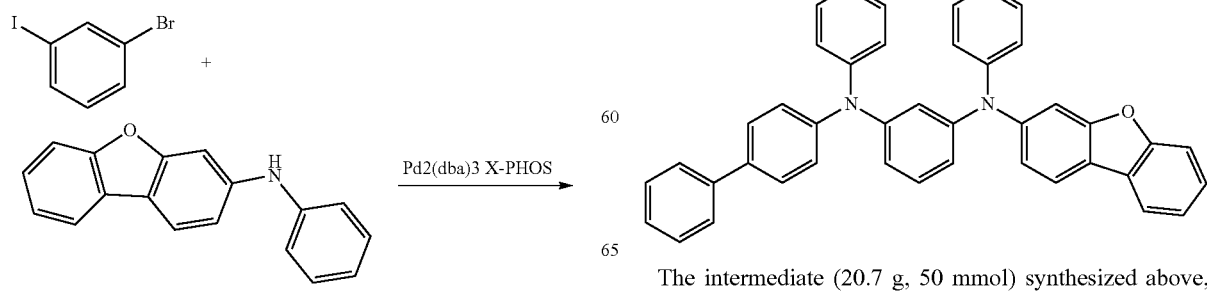

m-Bromoiodobenzene (28.3 g, 100 mmol), the intermediate II-C-1 (25.9 g, 100 mmol), tris(dibenzylideneacetone)dipalladium (0.91 g, 1 mmol), X-Phos (0.95 g, 2 mmol), and sodium tert-butoxide (19.2 g, 200 mmol) were added to methylbenzene (200 mL). The mixture was heated to 108° C. under the nitrogen atmosphere, stirred for 6 h, and then cooled to room temperature. The reaction mixture was washed with water, dried over magnesium sulfate, and then filtered. Then, the solvent was removed from the filtrate under reduced pressure. The residue was purified by silica gel column chromatography and eluted with n-heptane to obtain a white solid (26.49 g, 64%).

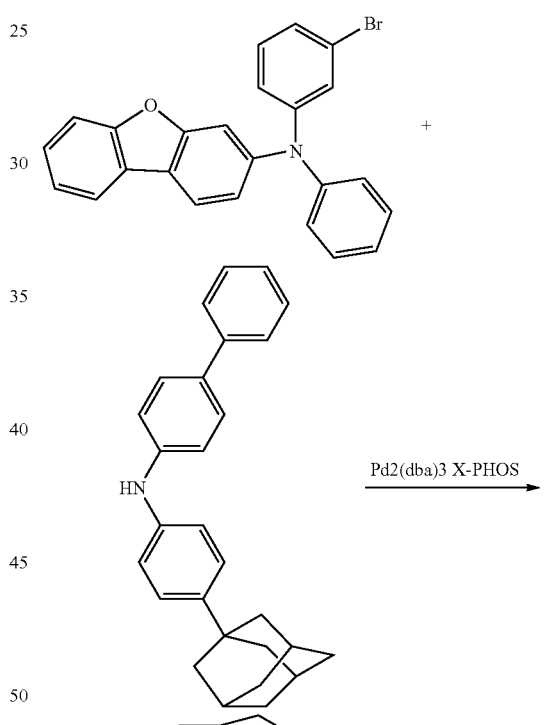

The intermediate (20.7 g, 50 mmol) synthesized above, the intermediate I-K (18.95 g, 50 mmol), tris(dibenzylideneacetone)dipalladium (0.49 g, 0.5 mmol), 2-(dicyclohexylphosphino)-2',4',6'-triisopropylbiphenyl (0.47 g, 1 mmol), and sodium tert-butoxide (9.6 g, 100 mmol) were added to methylbenzene (200 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of dichloromethane and n-heptane (v:v=1:3) to obtain the crude product. Then, the crude product was purified by recrystallization using a mixture of dichloromethane and ethyl acetate, to obtain compound as a white solid (20.67 g, 58%). MS: m/z=713.4 (M+H)+.

Synthesis Example 30

Synthesis of Compound 30

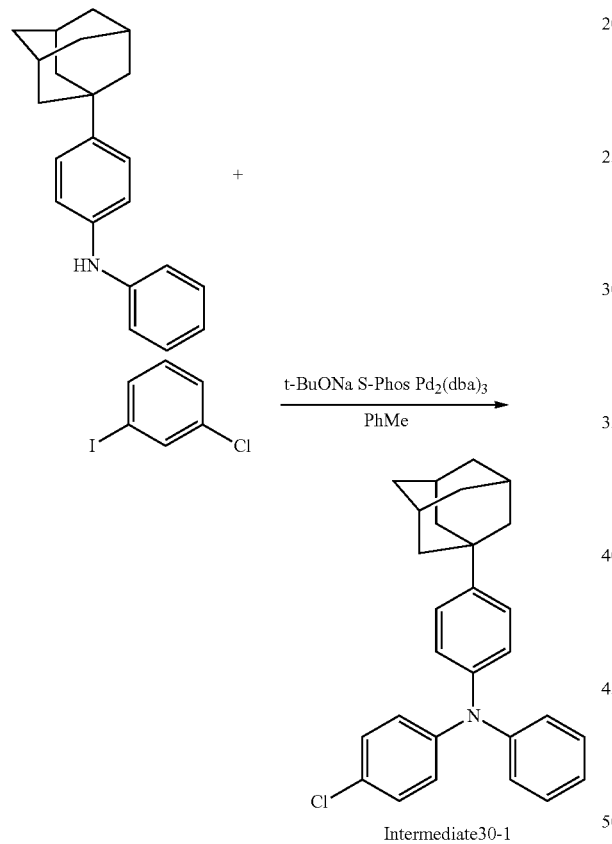

Intermediate30-1

The intermediate I-A (13.6 g, 4.5 mmol), m-chloroiodobenzene (1068 g, 4.5 mmol), tris(dibenzylideneacetone)dipalladium (0.41 g, 0.45 mmol), 2-(dicyclohexylphosphino)-2',6'-dimethoxylbiphenyl (0.3674 g, 0.9 mmol), and sodium tert-butoxide (5.16 g, 5.3 mmol) were added to methylbenzene (136 mL). The mixture was heated to 108° C. under the nitrogen atmosphere, stirred for 1 h, and then cooled to room temperature. After the reaction mixture was filtered, the solvent was removed from the filtrate under reduced pressure. The residue was purified by silica gel column chromatography and eluted with a mixture of dichloromethane and n-heptane (1:5) to obtain the crude product. Then, the crude product was purified by recrystallization using a mixture of dichloromethane and ethyl acetate, to obtain compound 30-1 as a white solid (15 g, 25%).

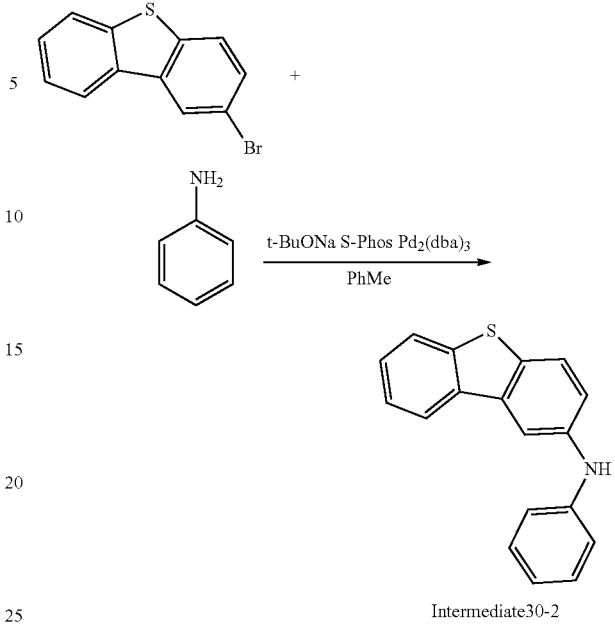

Intermediate30-2

Phenylamine (3.72 g, 4 mmol), 2-bromodibenzothiophene (10 g, 3.8 mmol), tris(dibenzylideneacetone)dipalladium (0.348 g, 0.38 mmol), 2-(dicyclohexylphosphino)-2,4,6-triisopropylbiphenyl (0.355 g, 0.76 mmol), and sodium tert-butoxide (5.478 g, 5.7 mmol) were added to methylbenzene (100 mL). The mixture was heated to 108° C. under the nitrogen atmosphere, stirred for 2 h, and then cooled to room temperature. The reaction mixture was washed with water, dried over magnesium sulfate, and filtered. Then, the filtrate passed through a short silica gel column, and the solvent was removed from the eluent under reduced pressure. The crude product was purified by recrystallization using a mixture of dichloromethane and n-heptane, to obtain intermediate 30-2 as a white solid (7.2 g, 72%).

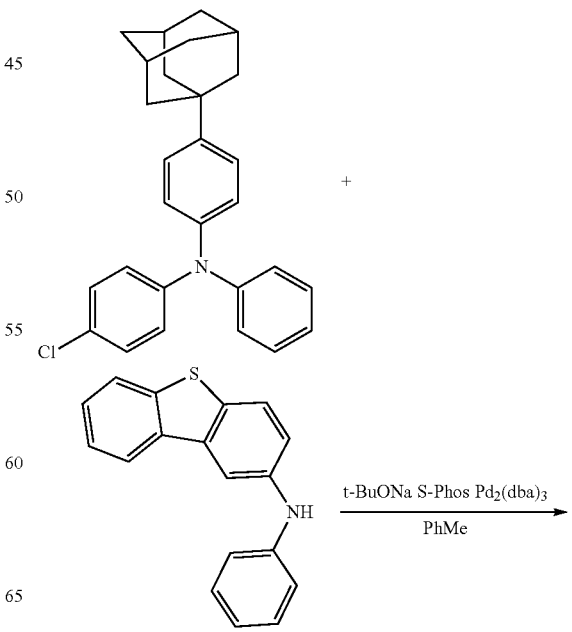

-continued

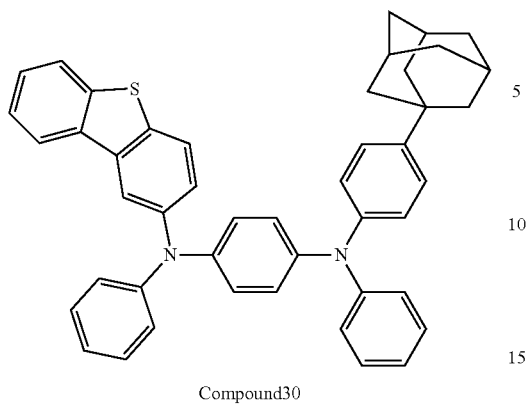

Compound 30

The intermediate 34-1 (6.2 g, 15 mmol) synthesized above, the intermediate 34-2 (4.13 g, 15 mmol), tris(dibenzylideneacetone)dipalladium (0.14 g, 0.15 mmol), 2-(dicyclohexylphosphino)-2',4',6'-triisopropylbiphenyl (0.13 g, 0.3 mmol), and sodium tert-butoxide (2.16 g, 22.5 mmol) were added to methylbenzene (60 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of dichloromethane and n-heptane (v:v=1:5) to obtain the crude product. Then, the crude product was purified by recrystallization using a mixture of dichloromethane and ethyl acetate, to obtain a white solid compound 30 (6.9, 71%). MS: m/z=653.3 (M+H)$^+$ Synthesis Example 31

Synthesis of Compound 31

-continued

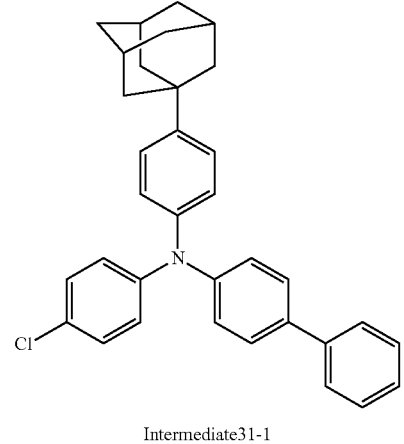

Intermediate 31-1

The intermediate I-k (17.1 g, 4.5 mmol), p-chloroiodobenzene (10.7 g, 4.5 mmol), tris(dibenzylideneacetone)dipalladium (0.41 g, 0.45 mmol), 2-(dicyclohexylphosphino)-2',6'-dimethoxylbiphenyl (0.3674 g, 0.9 mmol), and sodium tert-butoxide (5.16 g, 5.3 mmol) were added to methylbenzene (150 mL). The mixture was heated to 108° C. under the nitrogen atmosphere, stirred for 1 h, and then cooled to room temperature. After the reaction mixture was filtered, the solvent was removed from the filtrate under reduced pressure. The residue was purified by silica gel column chromatography and eluted with a mixture of methylbenzene and n-heptane (1:8) to obtain the crude product. Then, the crude product was purified by recrystallization using a mixture of methylbenzene and ethyl acetate, to obtain compound 31-1 as a white solid (16.6 g, 51%).

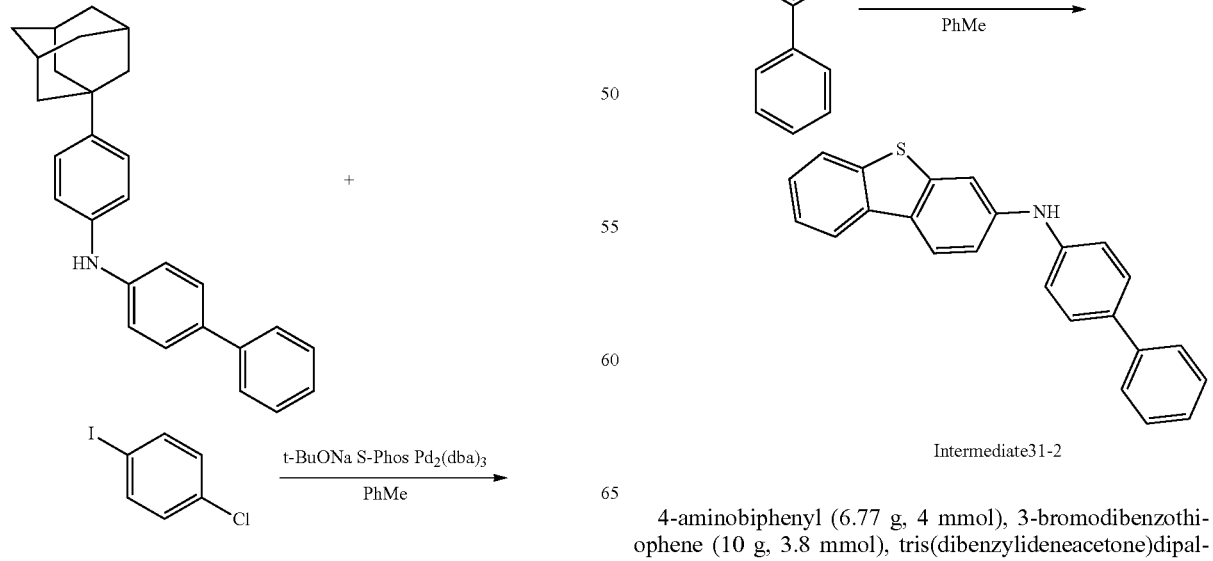

Intermediate 31-2

4-aminobiphenyl (6.77 g, 4 mmol), 3-bromodibenzothiophene (10 g, 3.8 mmol), tris(dibenzylideneacetone)dipalladium (0.348 g, 0.38 mmol), 2-(dicyclohexylphosphino)-2,4,6-triisopropylbiphenyl (0.355 g, 0.76 mmol), and sodium tert-butoxide (5.478 g, 5.7 mmol) were added to methylbenzene (100 mL). The mixture was heated to 108° C. under the nitrogen atmosphere, stirred for 2 h, and then cooled to room temperature. The reaction mixture was washed with water, dried over magnesium sulfate, and filtered. Then, the filtrate passed through a short silica gel column, and the solvent was removed from the eluent under reduced pressure. The crude product was purified by recrystallization using a mixture of dichloromethane and n-heptane, to obtain intermediate 31-2 as a white solid (10 g, 75%).

added to methylbenzene (60 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of methylbenzene and n-heptane (v:v=1:5) to obtain the crude product. Then, the crude product was purified by recrystallization using a mixture of methylbenzene and ethyl acetate, to obtain a white solid compound (7.8, 65%). MS: m/z=805.3 (M+H)$^+$ Synthesis Example 32

Synthesis of Compound 32

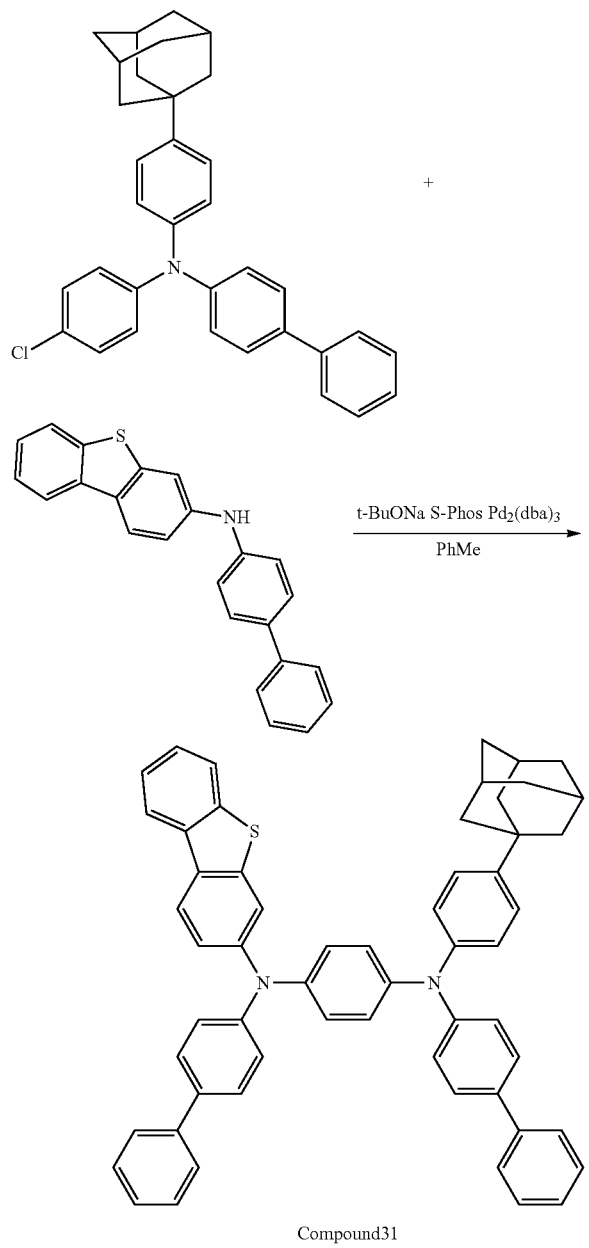

Compound31

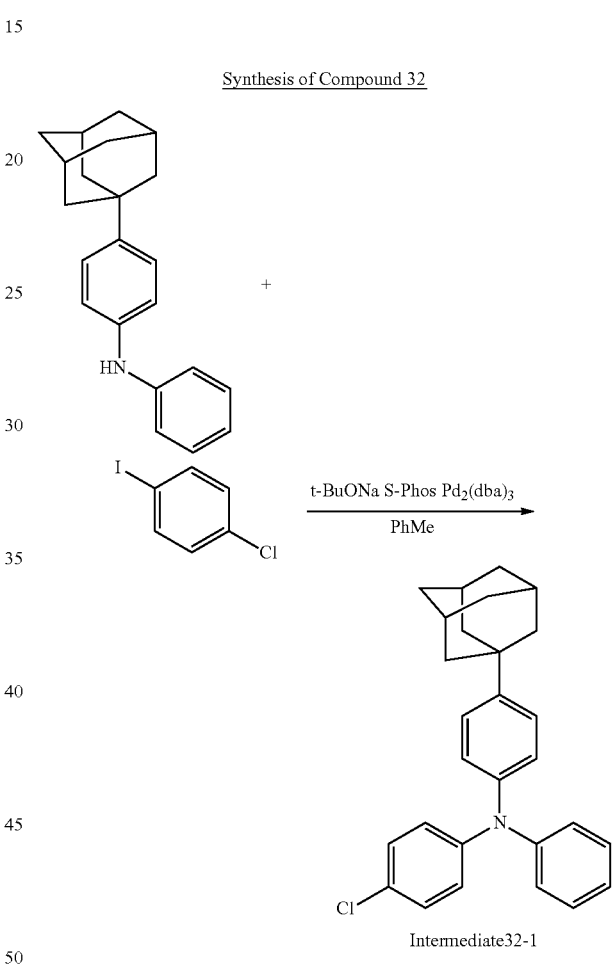

Intermediate32-1

The intermediate 31-1 (7.14 g, 15 mmol) synthesized above, the intermediate 31-2 (5.3 g, 15 mmol), tris(dibenzylideneacetone)dipalladium (0.14 g, 0.15 mmol), 2-(dicyclohexylphosphino)-2',4',6'-triisopropylbiphenyl (0.13 g, 0.3 mmol), and sodium tert-butoxide (2.16 g, 22.5 mmol) were The intermediate I-A (13.6 g, 4.5 mmol), p-chloroiodobenzene (10.68 g, 4.5 mmol), tris(dibenzylideneacetone)dipalladium (0.41 g, 0.45 mmol), 2-(dicyclohexylphosphino)-2',6'-dimethoxylbiphenyl (0.3674 g, 0.9 mmol), and sodium tert-butoxide (5.16 g, 5.3 mmol) were added to methylbenzene (136 mL). The mixture was heated to 108° C. under the nitrogen atmosphere, stirred for 1 h, and then cooled to room temperature. After the reaction mixture was filtered, the solvent was removed from the filtrate under reduced pressure. The residue was purified by silica gel column chromatography and eluted with a mixture of dichloromethane and n-heptane (1:5) to obtain the crude product. Then, the crude product was purified by recrystallization using a mixture of dichloromethane and ethyl acetate, to obtain compound 32-1 as a white solid (17 g, 75%).

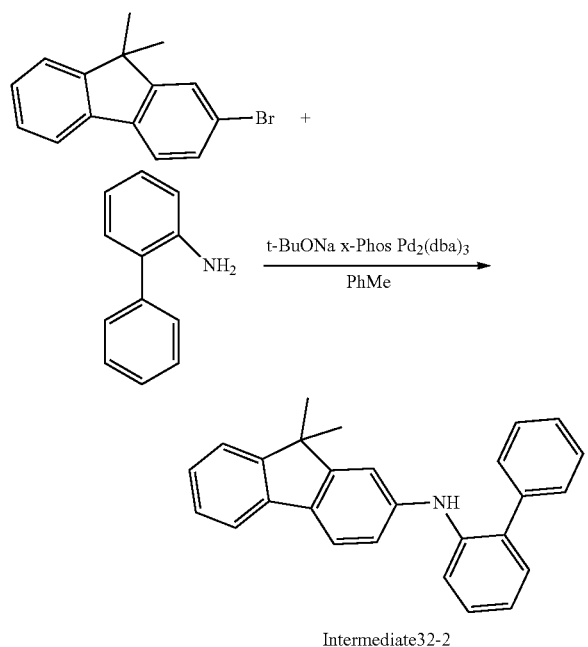

Intermediate32-2

2-Aminobiphenyl (6.77 g, 4 mmol), 2-bromofluorene (10.4 g, 3.8 mmol), tris(dibenzylideneacetone)dipalladium (0.348 g, 0.38 mmol), 2-(dicyclohexylphosphino)-2,4,6-triisopropylbiphenyl (0.355 g, 0.76 mmol), and sodium tert-butoxide (5.478 g, 5.7 mmol) were added to methylbenzene (100 mL). The mixture was heated to 108° C. under the nitrogen atmosphere, stirred for 2 h, and then cooled to room temperature. The reaction mixture was washed with water, dried over magnesium sulfate, and filtered. Then, the filtrate passed through a short silica gel column, and the solvent was removed from the eluent under reduced pressure. The crude product was purified by recrystallization using a mixture of methylbenzene and n-heptane, to obtain intermediate 32-2 as a white solid (10.43 g, 76%).

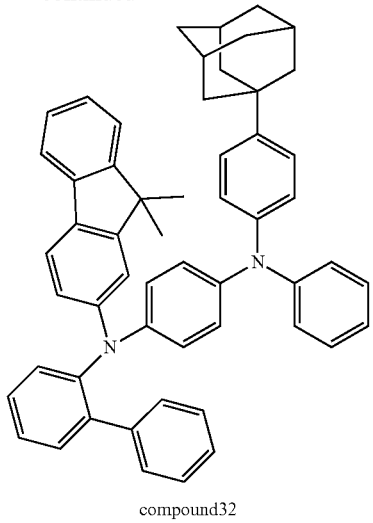

compound32

The intermediate 32-1 (6.2 g, 15 mmol) synthesized above, the intermediate 36-2 (5.4 g, 15 mmol), tris(dibenzylideneacetone)dipalladium (0.14 g, 0.15 mmol), 2-(dicyclohexylphosphino)-2',4',6'-triisopropylbiphenyl (0.13 g, 0.3 mmol), and sodium tert-butoxide (2.16 g, 22.5 mmol) were added to methylbenzene (60 mL). The mixture was heated to 108° C. under the nitrogen atmosphere, stirred for 2 h, and then cooled to room temperature. After the reaction mixture was filtered, the solvent was removed from the filtrate under reduced pressure. The residue was purified by silica gel column chromatography and eluted with a mixture of methylbenzene and n-heptane (v:v=1:5) to obtain the crude product. Then, the crude product was purified by recrystallization using a mixture of methylbenzene and ethyl acetate, to obtain compound 32 as a white solid (8.2, 73%). MS: m/z=739.4 (M+H)$^+$.

Manufacture of Organic Electroluminescent Device

Example 1: Organic Electroluminescent Device Using the Compound of the Present Disclosure as a Hole Transport Layer An anode was prepared using the following process: an ITO substrate (manufactured by Corning) with a thickness of 1500 Å was cut into a size of 40 mm×40 mm×0.7 mm, and was made into an experimental substrate with a cathode, an anode, and insulating layer patterns using a photoetching process. Surface treatment was performed using UV ozone and $O_2:N_2$ plasma, for increasing the work function of the anode (experimental substrate) and descumming.

m-MTDATA was vacuum-evaporated on the experimental substrate (anode) to form a hole injection layer (HIL) with a thickness of 100 Å, and Compound 1 was vacuum-evaporated on the hole injection layer to form a hole transport layer (HTL) with a thickness of 800 Å.

TCTA was evaporated on the hole transport layer to form an electron-blocking layer (EBL) with a thickness of 300 Å.

4,4'-(3,8-diphenylpyren-1,6-diyl)bis(N,N-diphenylaniline) was blended into a host compound α, β-AND, to form an emitting layer (EML) with a thickness of 350 Å.

DBimiBphen and LiQ were mixed at a weight ratio of 1:1, and evaporated to form an electron transport layer (ETL) with a thickness of 300 Å. LiQ was evaporated on the electron transport layer to form an electron injection layer (EIL) with a thickness of 10 Å. Then, magnesium (Mg) and argentum (Ag) were mixed at an evaporation rate of 1:9, and vacuum-evaporated on the electron injection layer to form a cathode with a thickness of 120 Å.

In addition, N-(4-(9H-carbazol-9-yl)phenyl)-4'-(9H-carbazol-9-yl)-N-phenyl-[1,1'-biphenyl]-4-amine with a thickness of 65 nm was evaporated on the above cathode, to form a capping layer (CPL), thereby completing the manufacture of the organic electroluminescent device.

Example 2-23

Except that the compound shown in Table 1 was used to form the hole transport layer (HTL), organic electroluminescent devices were manufactured using a method identical to that in Example 1, The performance of the above devices were shown in Table 1.

Comparison Example 1 to Comparison Example 2

In Comparison Example 1 to Comparison Example 2, except that Compound 1 was replaced with NPB and Compound B as the hole transport layer separately, the organic electroluminescent device was manufactured using a method identical to that in Example 1. That is, the organic electroluminescent device was manufactured using NPB to replace Compound 1 in Comparison Example 1, while the organic electroluminescent device was manufactured using Compound B to replace Compound 1 in Comparison Example 2. Both of the performance of the device were shown in Table 1.

The electroluminescent device was prepared from materials having the following structures:

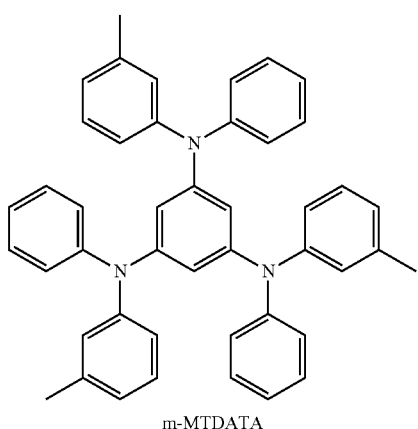

m-MTDATA

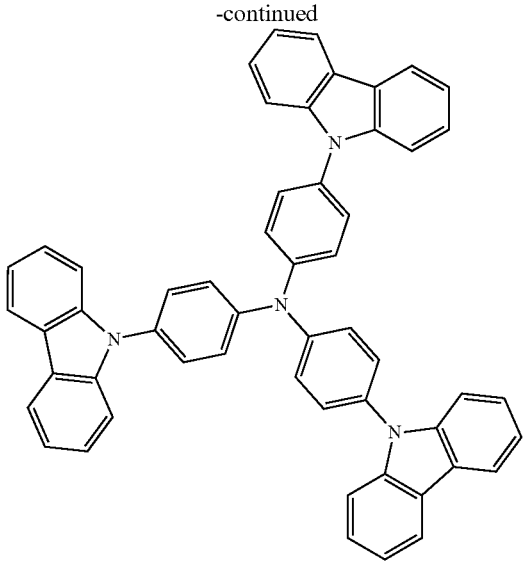

TCTA

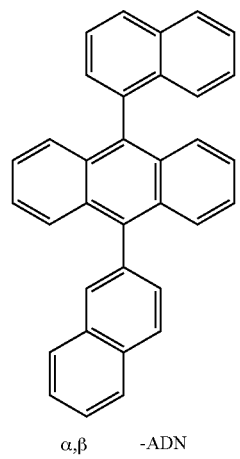

α,β -ADN

LiQ

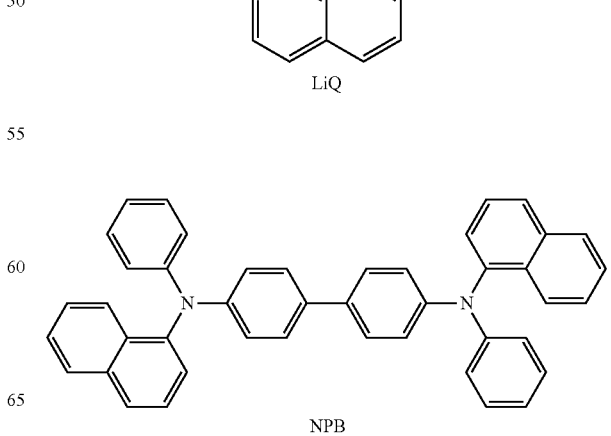

NPB

The performance of the organic electroluminescent device manufactured above was analyzed under the condition of 20 mA/cm², with the results thereof shown in Table 1 below.

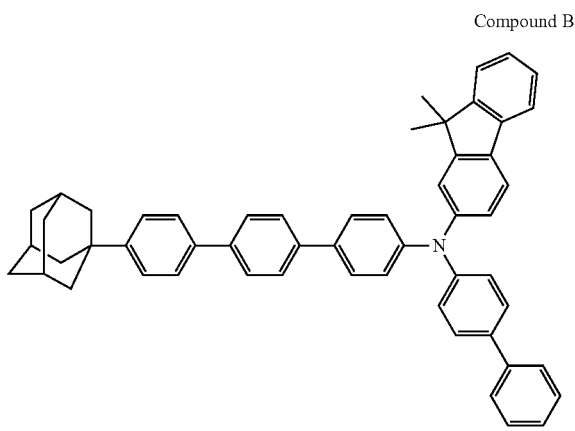 [SMILES: CC1(C)c2ccccc2-c2ccc(N(c3ccc(-c4ccccc4)cc3)c3ccc(-c4ccc(-c5ccc(C67CC8CC(CC(C8)C6)C7)cc5)cc4)cc3)cc21]

Compound B

TABLE 1

| Examples | Compound | Volt (V) | Cd/A | EQE(%) | T95 (hrs) | CIEx | CIEy |
|---|---|---|---|---|---|---|---|
| Example 1 | Compound 1 | 4.0 | 6.7 | 14.3 | 200 | 0.140 | 0.045 |
| Example 2 | Compound 2 | 4.1 | 6.8 | 14.6 | 210 | 0.141 | 0.044 |
| Example 3 | Compound 3 | 3.9 | 6.9 | 14.9 | 198 | 0.141 | 0.045 |
| Example 4 | Compound 4 | 4.2 | 7.2 | 15.1 | 209 | 0.141 | 0.042 |
| Example 5 | Compound 5 | 3.8 | 6.4 | 14.7 | 180 | 0.142 | 0.044 |
| Example 6 | Compound 6 | 3.9 | 6.6 | 14.3 | 176 | 0.143 | 0.043 |
| Example 7 | Compound 7 | 4.4 | 6.4 | 14.4 | 169 | 0.142 | 0.042 |
| Example 8 | Compound 11 | 4.1 | 6.8 | 14.5 | 165 | 0.141 | 0.044 |
| Example 9 | Compound 12 | 4.18 | 6.7 | 14.0 | 168 | 0.143 | 0.045 |
| Example 10 | Compound 13 | 3.98 | 6.4 | 14.4 | 167 | 0.142 | 0.047 |
| Example 11 | Compound 14 | 3.93 | 6.5 | 13.5 | 174 | 0.141 | 0.046 |
| Example 12 | Compound 15 | 4.37 | 6.5 | 13.3 | 172 | 0.140 | 0.045 |
| Example 13 | Compound 16 | 4.28 | 6.8 | 14.2 | 198 | 0.141 | 0.048 |
| Example 14 | Compound 17 | 3.98 | 6.4 | 13.8 | 194 | 0.141 | 0.045 |
| Example 15 | Compound 18 | 4.02 | 6.8 | 13.3 | 174 | 0.141 | 0.042 |
| Example 16 | Compound 21 | 4.14 | 6.8 | 13.2 | 203 | 0.140 | 0.045 |
| Example 17 | Compound 22 | 3.98 | 6.8 | 13.2 | 172 | 0.141 | 0.046 |
| Example 18 | Compound 24 | 3.97 | 6.7 | 14.6 | 205 | 0.141 | 0.046 |
| Example 19 | Compound 25 | 4.07 | 6.7 | 14.3 | 205 | 0.142 | 0.044 |
| Example 20 | Compound 28 | 4.03 | 6.6 | 14.1 | 193 | 0.141 | 0.046 |
| Example 21 | Compound 30 | 3.92 | 6.7 | 14.5 | 183 | 0.141 | 0.047 |
| Example 22 | Compound 32 | 4.02 | 6.4 | 13.7 | 198 | 0.143 | 0.045 |
| Example 23 | Compound 31 | 4.1 | 6.8 | 14.5 | 195 | 0.141 | 0.044 |
| Comparison Example 1 | NPB | 5.0 | 4.0 | 6.4 | 80 | 0.142 | 0.043 |
| Comparison Example 2 | Compound B | 4.4 | 5.9 | 10 | 160 | 0.141 | 0.043 |

As can be seen from the evaluation results of the device in the above Table 1, the compounds of the present disclosure were used as the hole transport layer (HTL) in Examples 1-7. Compared with the compounds in Comparison Examples 1-2, when the color coordinate CIEy was not greatly different, the experimental test is carried out under the same current density, all of the organic electroluminescent devices made of the compounds of the present disclosure have significantly lower drive voltage (V), and have significantly higher current efficiency (Cd/A) and external quantum efficiency (EQE) obviously superior to those of the device made of the compound in the comparison examples, showing a trend of improvement. The service life (T95) has significantly prolonged, and the external quantum efficiency is increased by more than 30%.

Example 24: Organic Electroluminescent Device Using the Compound of the Present Disclosure as an Electron-Blocking Layer An anode was prepared using the following process: an ITO substrate (manufactured by Corning) with a thickness of 1500 Å was cut into a size of 40 mm×40 mm×0.7 mm, and was made into an experimental substrate with a cathode, an anode, and insulating layer patterns using a photoetching process. Surface treatment was performed using UV ozone and $O_2:N_2$ plasma, for increasing the work function of the anode (experimental substrate) and descumming.

m-MTDATA was vacuum-evaporated on the experimental substrate (anode) to form a hole injection layer (HIL) with a thickness of 100 Å, and compound NPB was vacuum-evaporated on the hole injection layer to form a hole transport layer (HTL) with a thickness of 1000 Å.

Compound 8 of the present disclosure was evaporated on the hole transport layer to form an electron-blocking layer (EBL) with a thickness of 300 Å.

4,4'-(3,8-diphenylpyren-1,6-diyl)bis(N,N-diphenylaniline) was blended into a host compound α, β-AND, to form an emitting layer (EML) with a thickness of 350 Å.

DBimiBphen and LiQ were mixed at a weight ratio of 1:1, and evaporated to form an electron transport layer (ETL) with a thickness of 300 Å. LiQ was evaporated on the electron transport layer to form an electron injection layer (EIL) with a thickness of 10 Å. Then, magnesium (Mg) and argentum (Ag) were mixed at a ratio of 1:9, and vacuum-evaporated on the electron injection layer to form a cathode with a thickness of 120 Å.

In addition, N-(4-(9H-carbazol-9-yl)phenyl)-4'-(9H-carbazol-9-yl)-N-phenyl-[1,1'-biphenyl]-4-amine with a thickness of 650 Å was evaporated on the above cathode, to form a capping layer (CPL), thereby completing the manufacture of the organic electroluminescent device.

Examples 24-35

Except that the compound shown in Table 2 was used to form the electron-blocking layer (EBL), organic electroluminescent devices were manufactured using a method identical to that in Example 24.

That is, the organic electroluminescent device was manufactured using Compound 9 of the present disclosure in Example 25, while the organic electroluminescent device was manufactured using Compound 10 of the present disclosure in Example 26, The performance of the above devices were shown in Table 2.

Comparison Example 3 to Comparison Example 5

In the Comparison Example 3 to Comparison Example 5, except that Compound 8 was replaced with TCTA, NPD,

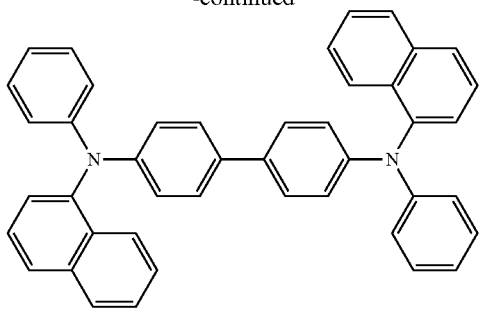

NPD

The performance of the organic electroluminescent device prepared above was analyzed under the condition of 20 mA/cm$^2$, with the results thereof shown in Table 2 below.

TABLE 2

| Examples | Compound | Volt (V) | Cd/A | EQE(%) | T95 (hrs) | CIEx | CIEy |
| --- | --- | --- | --- | --- | --- | --- | --- |
| Example 24 | Compound 8 | 4.1 | 6.5 | 12.1 | 152 | 0.141 | 0.043 |
| Example 25 | Compound 9 | 3.7 | 6.1 | 14.4 | 178 | 0.143 | 0.043 |
| Example 26 | Compound 10 | 4.5 | 6.1 | 13.2 | 186 | 0.142 | 0.042 |
| Example 27 | Compound 19 | 4.0 | 6.4 | 14.6 | 167 | 0.141 | 0.043 |
| Example 28 | Compound 20 | 3.8 | 6.7 | 14.9 | 155 | 0.143 | 0.042 |
| Example 29 | Compound 23 | 3.8 | 6.5 | 14.7 | 168 | 0.142 | 0.042 |
| Example 30 | Compound 26 | 3.9 | 6.6. | 14.7 | 175 | 0.143 | 0.043 |
| Example 31 | Compound 27 | 4.1 | 6.3 | 14.4 | 176 | 0.143 | 0.044 |
| Example 32 | Compound 29 | 4.0 | 6.5 | 14.5 | 183 | 0.142 | 0.042 |
| Example 33 | Compound 30 | 4.1 | 6.4 | 14.4 | 188 | 0.143 | 0.043 |
| Example 34 | Compound 31 | 3.9 | 6.3 | 14.2 | 185 | 0.143 | 0.043 |
| Example 35 | Compound 32 | 4.1 | 6.4 | 13.5 | 189 | 0.142 | 0.042 |
| Comparison Example 3 | TCTA | 5.0 | 5.1 | 8.3 | 75 | 0.141 | 0.044 |
| Comparison Example 4 | NPD | 6.5 | 4.2 | 8.7 | 68 | 0.140 | 0.043 |
| Comparison Example 5 | TPD | 5.7 | 4.9 | 9.5 | 59 | 0.144 | 0.045 | and TPD as the electron-blocking layer separately, the organic electroluminescent device was manufactured using a method identical to that in Example 24.

That is, the organic electroluminescent device was manufactured using TCTA to replace Compound 8 in Comparison Example 3, the organic electroluminescent device was manufactured using NPD to replace Compound 8 in Comparison Example 4, and the organic electroluminescent device was manufactured using TPD to replace Compound 8 in Comparison Example 5. All of the performances of the device shown in Table 2.

The electroluminescent device was manufactured using materials having the following structures:

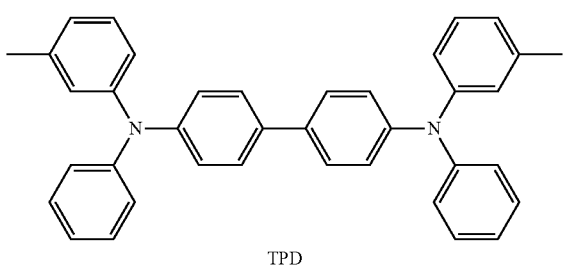

TPD

As can be seen from the evaluation results of the device in the above Table 2, the compounds of the present disclosure were used as the electron-blocking layer (EBL) in Examples 24-35. Compared with the compounds in Comparison Examples 3-5, when the color coordinate CIEy was not greatly different, the experimental test is carried out under the same current density, all of the organic electroluminescent devices made of the compounds of the present disclosure have significantly lower drive voltage (V), and have significantly higher current efficiency (Cd/A) and external quantum efficiency (EQE) obviously superior to those of the device made of the compound in the comparison examples, showing a trend of improvement. The service life (T95) has significantly prolonged.

As can be seen from Table 2, when the compound of the present disclosure is used in an electron-blocking layer of a blue light device, the external quantum efficiency is increased by more than 20% compared with that in the comparison examples, which is a very significant improvement for the blue light device. For an OLED device (i.e., organic electroluminescent device), the improvement in its effects (for example, in respect of EQE) is only a few percent in terms of data, but such improvement is also very significant.

Specifically, the external quantum efficiency (EQE) may be computed according to the following formula, for example, EQE=quantity of photons emitted from the component/quantity of injected electrons; for another example, EQE=light emitting efficiency*internal quantum efficiency (light emitting efficiency less than 1).

For the blue light device, a fluorescent material is used for the emitting layer, the fluorescent material emits light from singlet excitons, and its internal quantum efficiency is up to 25%. When light is emitted to the outside, due to light losses caused by device structures such as coupling, and other reasons, only 25% excitons can be used. Therefore, the external quantum efficiency must be lower than 25%, such that its efficiency is generally low.

Therefore, the device made of the compound of the present disclosure is characterized by reduced drive voltage, improved light emitting efficiency, and prolonged service life.

In conclusion, the compound of the present disclosure is used for a hole transport layer or an electron-blocking layer of an organic electroluminescent device, such that the organic electroluminescent device including the compound has lower drive voltage, higher light emitting efficiency, and longer service life.

The above examples are only further descriptions of the compound of the present disclosure, and are not intended to limit the scope of protection claimed in the present disclosure. For those of ordinary skills in the art to which the present disclosure belongs, various supplements and modifications made to the present disclosure without departing from the scope of the technical idea of the present disclosure disclosed in the scope of protection claimed in the disclosure also belong to the scope of protection of the present disclosure.

The invention claimed is:

1. An organic electroluminescent material, having a structure as shown in chemical formula 1:

Chemical formula 1

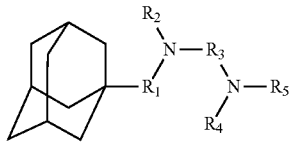

wherein $R_2$, $R_4$, and $R_5$ are identical or different, and are each independently selected from the following substituted or unsubstituted groups: phenyl, naphthyl, pyrenyl, dimethylfluorenyl, anthracenyl, phenanthryl, chrysenyl, azulenyl, acenaphthenyl, biphenyl, benzanthracenyl, quinolinyl, indolyl, carbazolyl, dibenzofuryl, dibenzothienyl, and dibenzoselenophenyl;

$R_1$ and $R_3$ are identical or different, and are each independently selected from substituted or unsubstituted following groups: phenylene, naphthylene, pyrenylene, dimethylfluorenylene, anthracenylene, phenanthrylene, chrysenylene, azulenylene, acenaphthenylene, biphenylene, terphenylene, and benzanthracenylene;

the "substituted" means to be independently substituted by substituent(s) selected from the following groups: methyl, ethyl, propyl, and aryl group with 6 carbon atoms.

2. The organic electroluminescent material according to claim 1, wherein $R_1$ and $R_3$ are identical or different, and are each independently selected from substituted or unsubstituted phenylene, substituted or unsubstituted biphenylene, substituted or unsubstituted terphenylene, substituted or unsubstituted chrysenylene, substituted or unsubstituted phenanthrylene, substituted or unsubstituted naphthylene, and substituted or unsubstituted azulenylene;

the "substituted" means to be independently substituted by substituent(s) selected from the following groups: methyl, ethyl, propyl, and aryl group with 6 carbon atoms.

3. An organic electroluminescent material, which has one of the following structures:

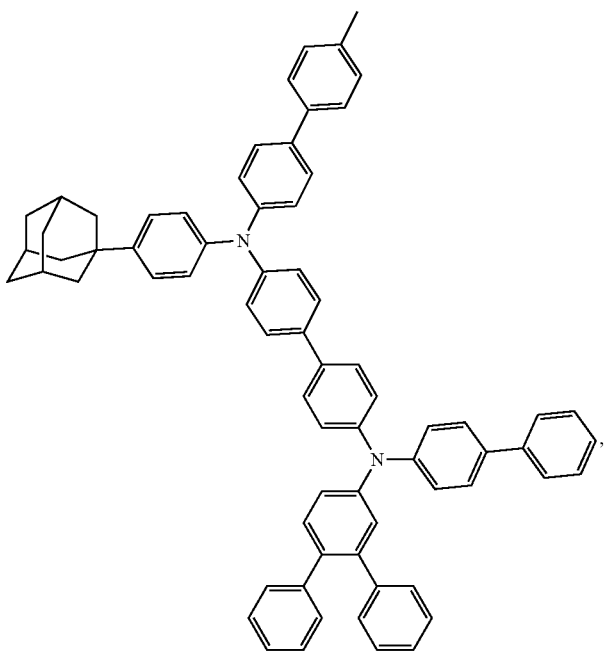

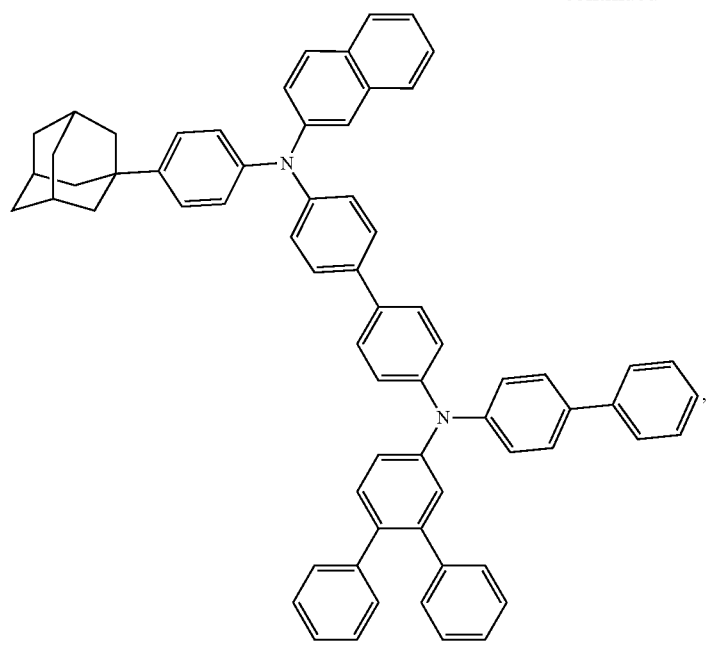
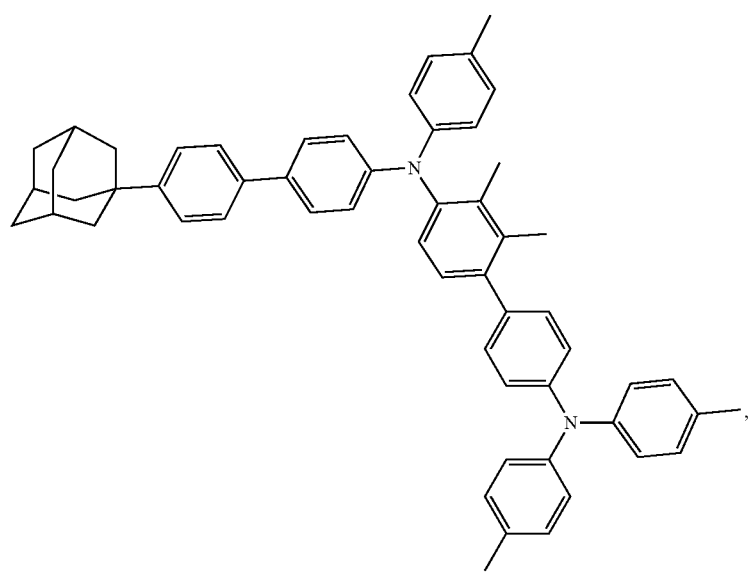

159 160
-continued
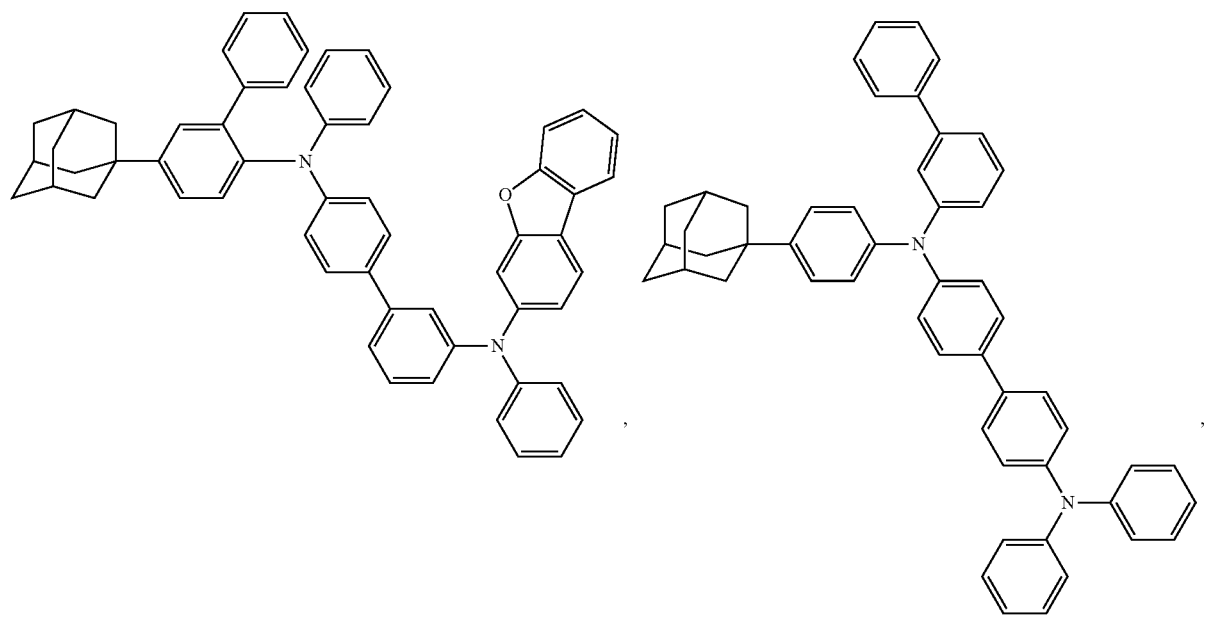
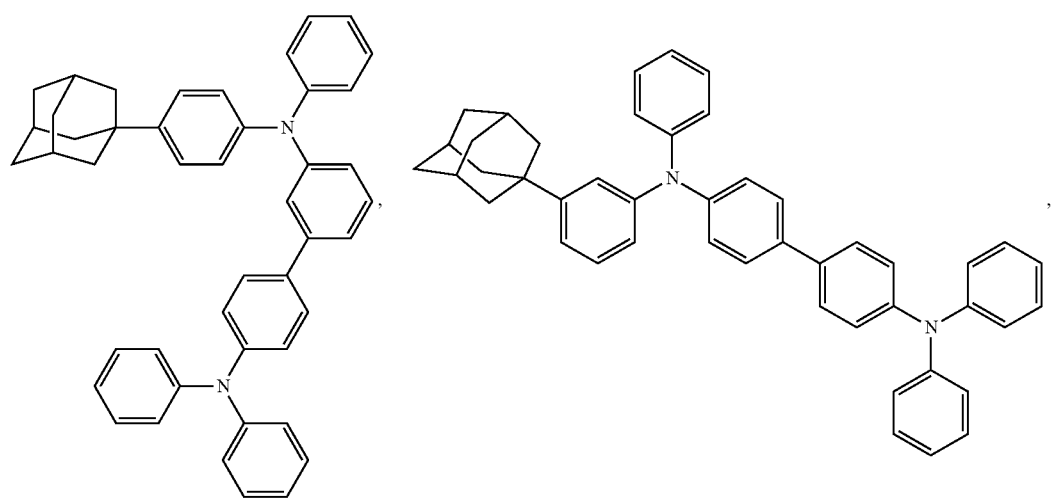

-continued
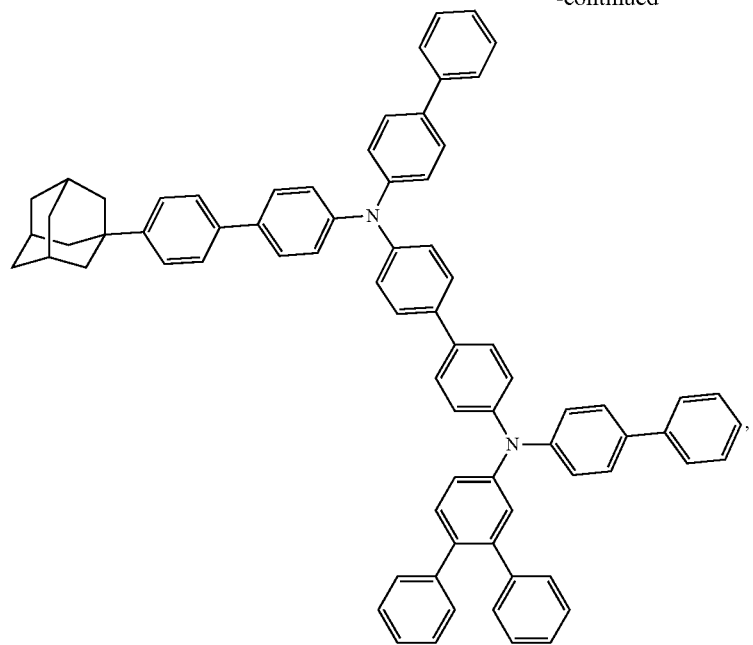
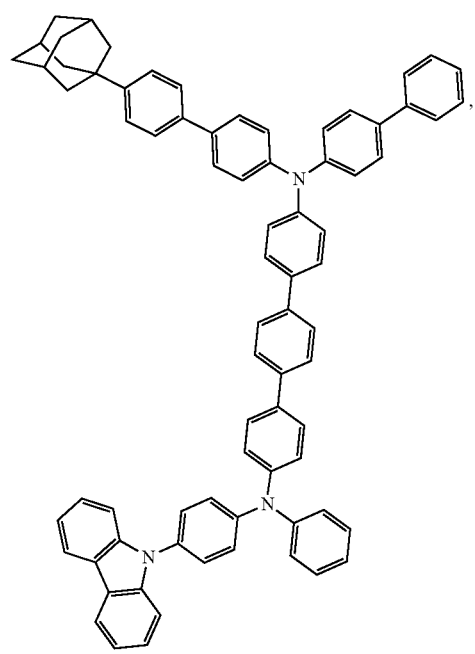

-continued
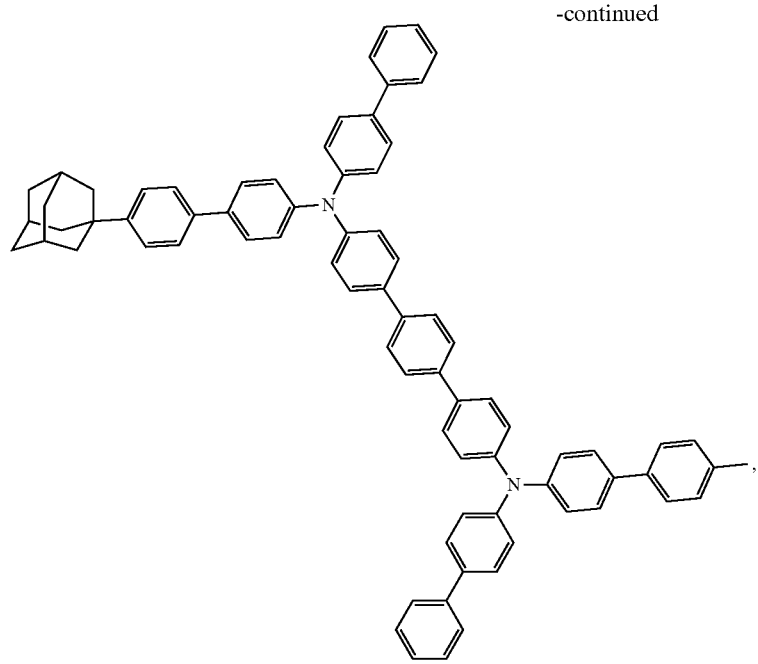
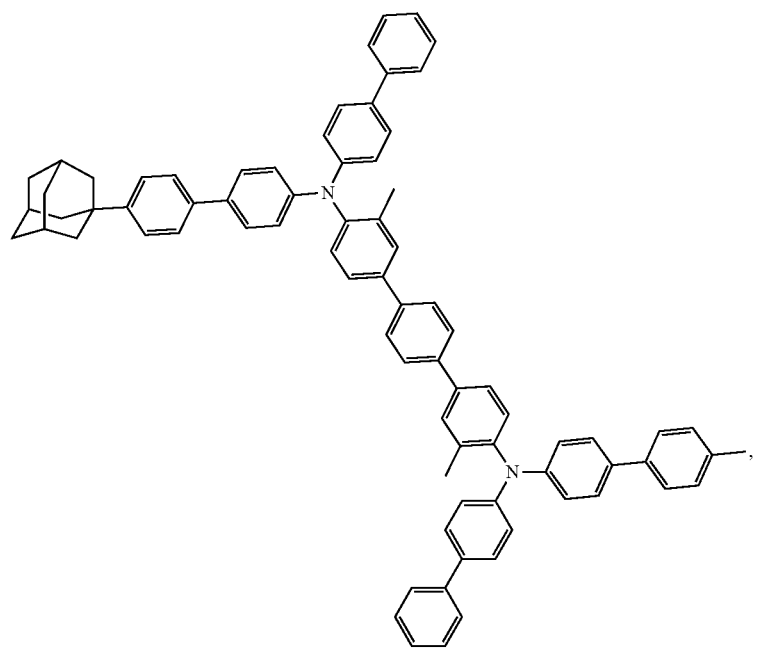

-continued
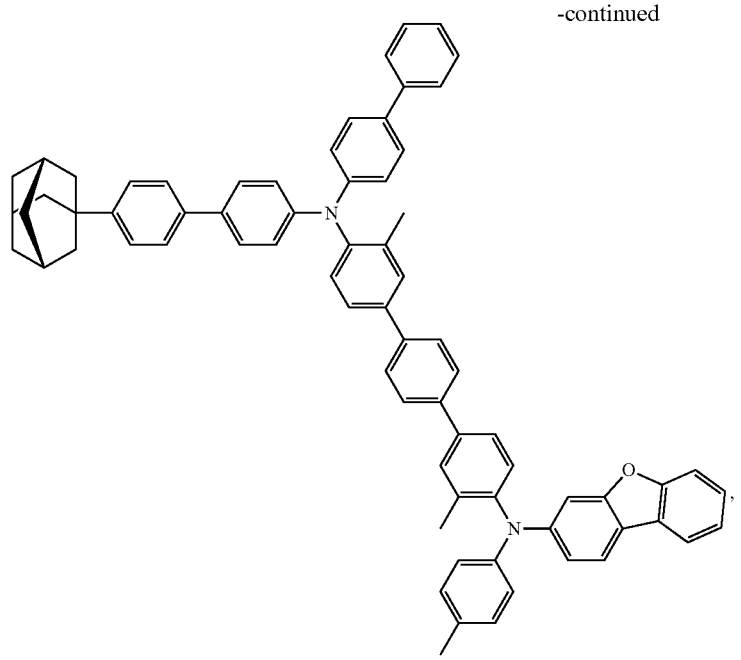
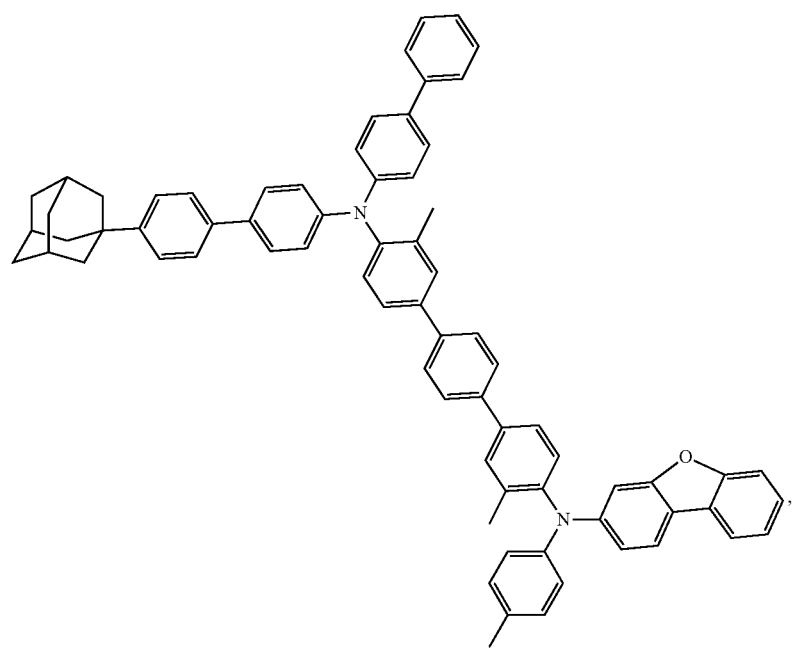

-continued
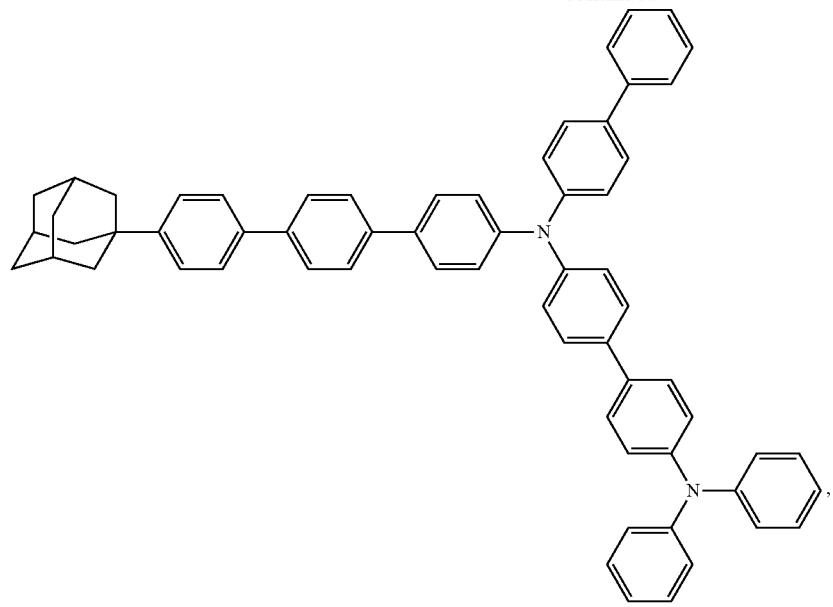
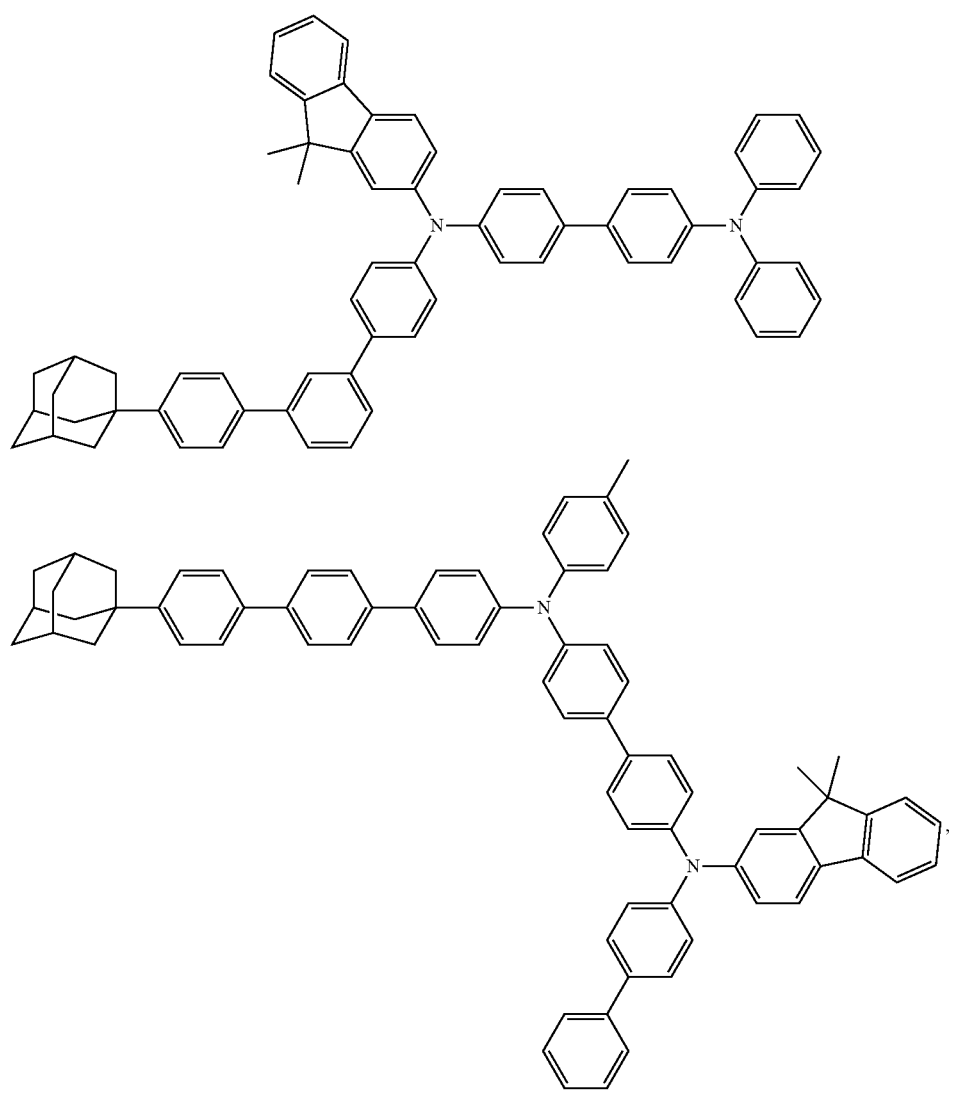

-continued
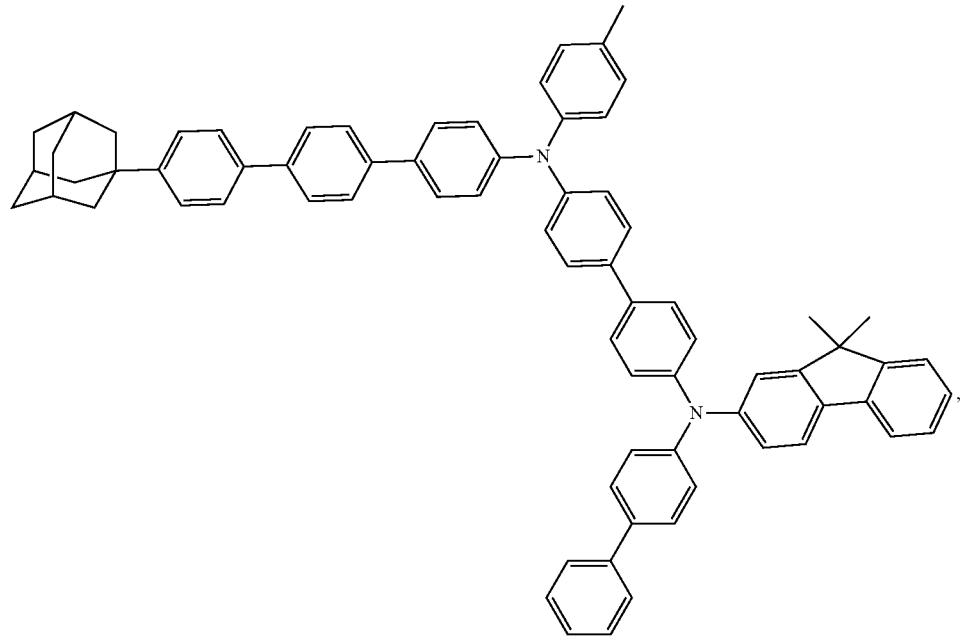
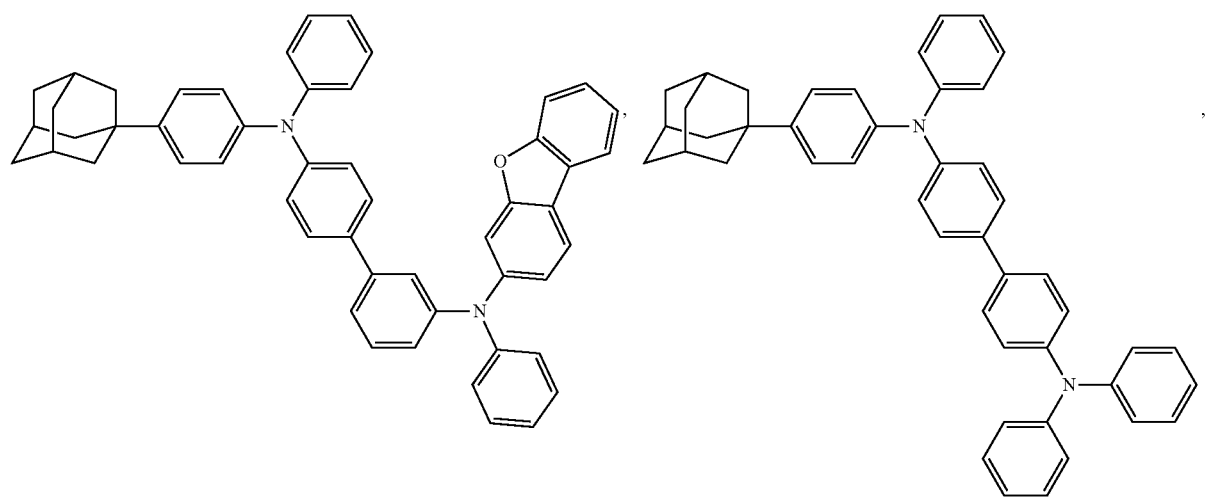
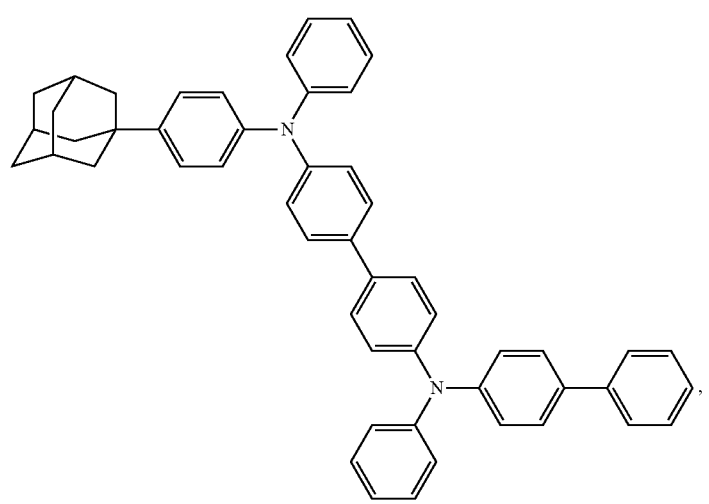

-continued
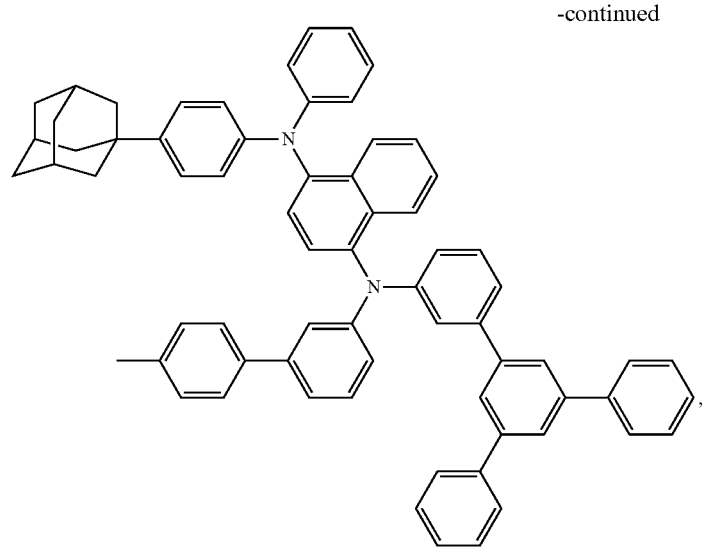
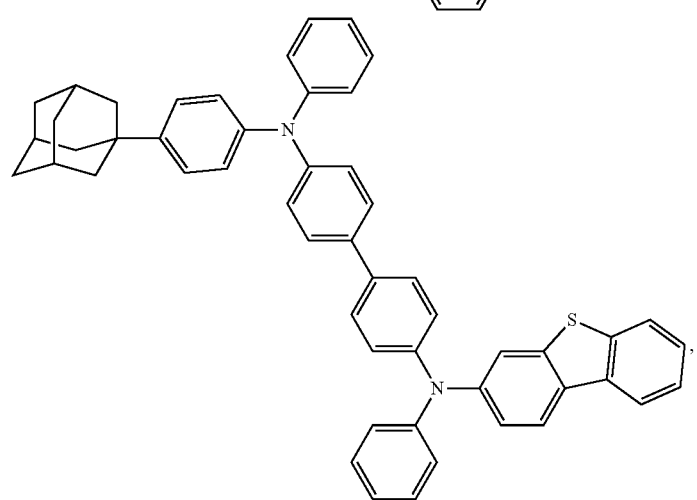
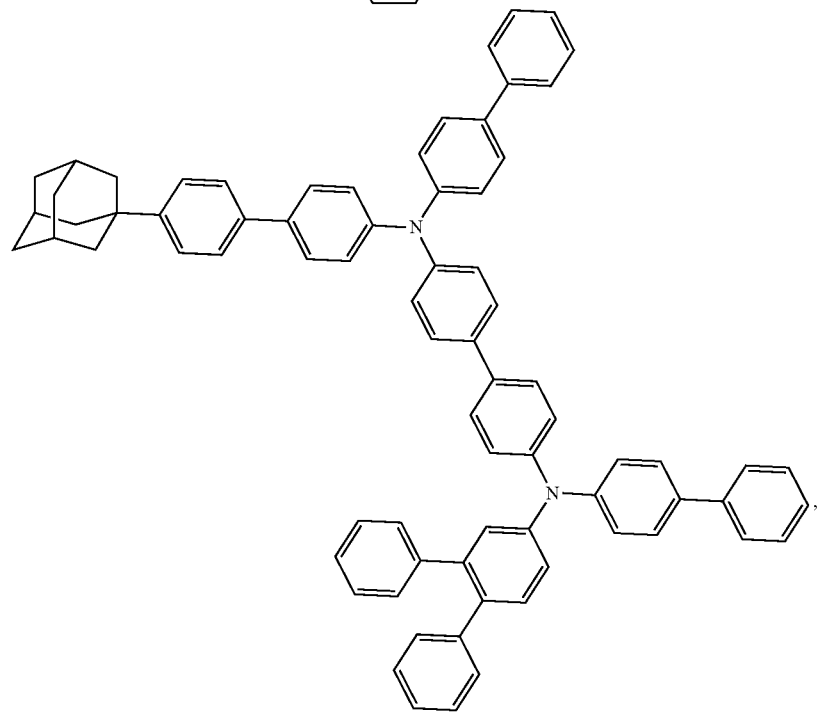

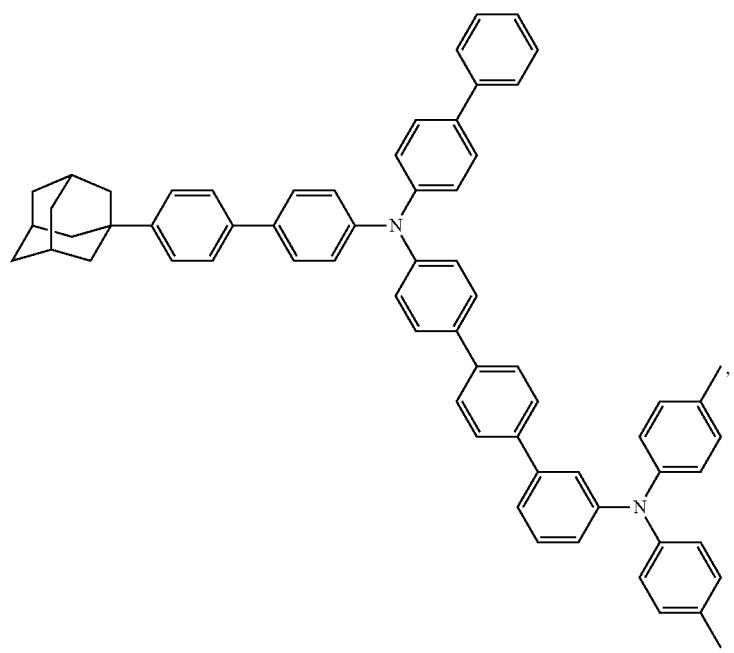
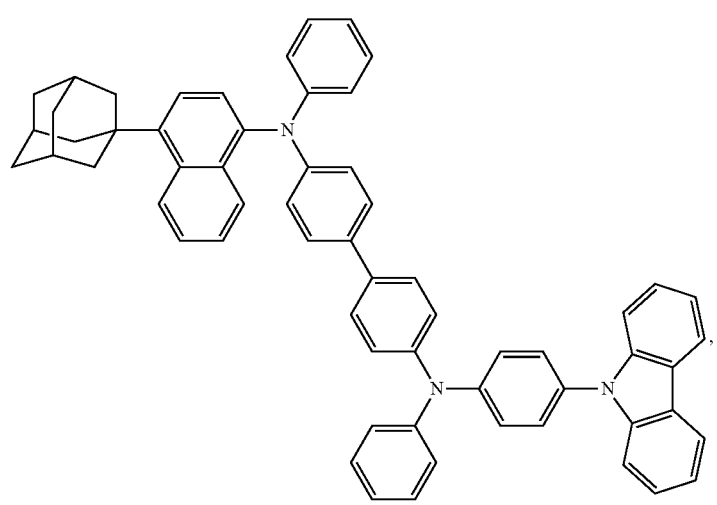

-continued

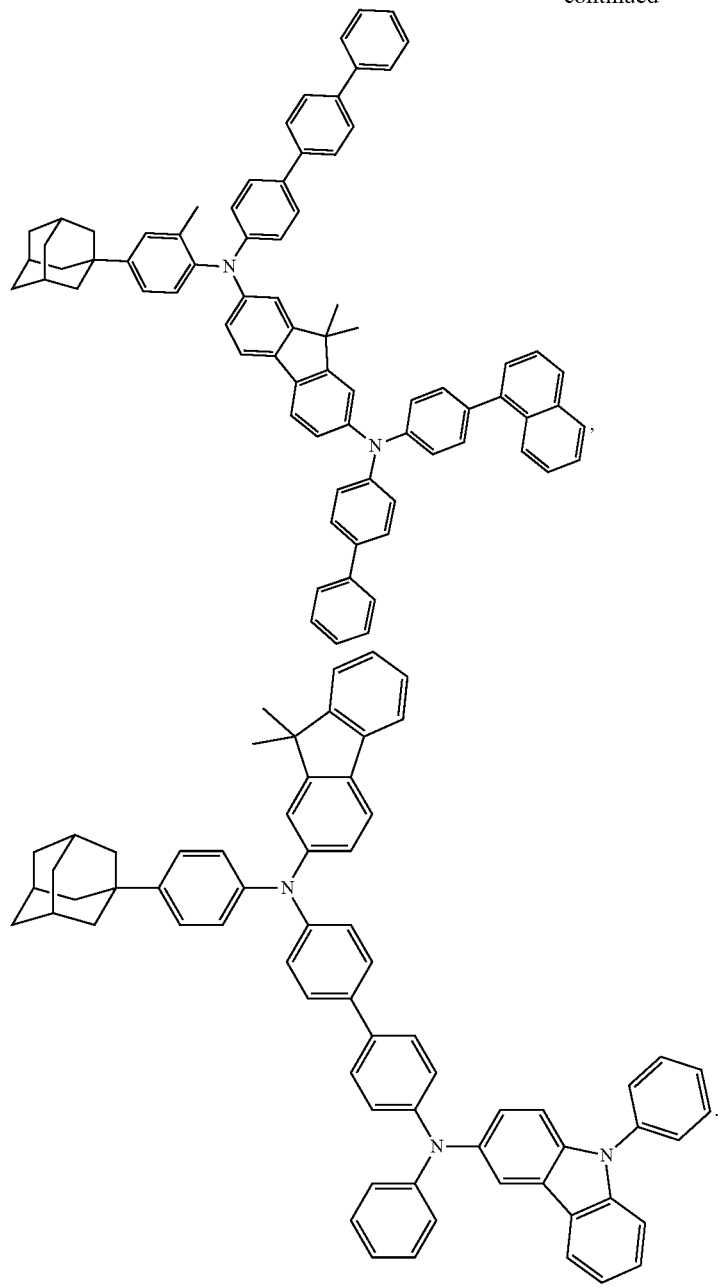

4. An organic electroluminescent device, comprising a cathode, an anode, and one or more organic layers arranged between the cathode and the anode, at least one of the organic layers comprising the electroluminescent material according to claim 1.

5. The organic electroluminescent device according to claim 4, wherein the organic layer comprises a hole injection layer, a hole transport layer, an electron-blocking layer, an emitting layer, a hole blocking layer, an electron transport layer, and an electron injection layer.

6. The organic electroluminescent device according to claim 5, wherein the electroluminescent material is comprised in the hole transport layer.

7. The organic electroluminescent device according to claim 5, wherein the electroluminescent material is comprised in the electron-blocking layer.

8. An organic electroluminescent device, comprising a cathode, an anode, and one or more organic layers arranged between the cathode and the anode, at least one of the organic layers comprising the electroluminescent material according to claim 3.

9. The organic electroluminescent device according to claim 8, wherein the organic layers comprise a hole injection layer, a hole transport layer, an electron-blocking layer, a light emitting layer, a hole blocking layer, an electron transport layer, and an electron injection layer.

10. The organic electroluminescent device according to claim 9, wherein the electroluminescent material is comprised in the hole transport layer.

11. The organic electroluminescent device according to claim 9, wherein the electroluminescent material is comprised in the electron-blocking layer.

* * * * *